United States Patent
Scholz et al.

(10) Patent No.: US 10,471,036 B2
(45) Date of Patent: Nov. 12, 2019

(54) ANTIMICROBIAL COMPOSITIONS AND METHODS

(71) Applicant: 3M INNOVATIVE PROPERTIES COMPANY, St. Paul, MN (US)

(72) Inventors: Matthew T. Scholz, Woodbury, MN (US); Dianne L. Gibbs, St. Paul, MN (US); John T. Capecchi, Oakdale, MN (US); Jeffrey F. Andrews, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 231 days.

(21) Appl. No.: 13/942,122

(22) Filed: Jul. 15, 2013

(65) Prior Publication Data

US 2013/0303615 A1    Nov. 14, 2013

Related U.S. Application Data

(63) Continuation of application No. 10/937,059, filed on Sep. 8, 2004, now Pat. No. 8,512,723, which is a continuation-in-part of application No. 10/659,571, filed on Sep. 9, 2003, now abandoned.

(51) Int. Cl.

| | | |
|---|---|---|
| *A61K 31/23* | (2006.01) | |
| *A61K 9/00* | (2006.01) | |
| *A61K 31/19* | (2006.01) | |
| *A61K 31/231* | (2006.01) | |
| *A61K 31/25* | (2006.01) | |
| *A61K 45/06* | (2006.01) | |
| *A61K 47/06* | (2006.01) | |
| *A61K 47/10* | (2017.01) | |
| *A61K 47/12* | (2006.01) | |
| *A61K 47/14* | (2017.01) | |
| *A61K 47/20* | (2006.01) | |
| *A61K 47/44* | (2017.01) | |

(52) U.S. Cl.
CPC .............. *A61K 31/23* (2013.01); *A61K 9/007* (2013.01); *A61K 9/0014* (2013.01); *A61K 9/0043* (2013.01); *A61K 9/0046* (2013.01); *A61K 9/0053* (2013.01); *A61K 31/19* (2013.01); *A61K 31/231* (2013.01); *A61K 31/25* (2013.01); *A61K 45/06* (2013.01); *A61K 47/06* (2013.01); *A61K 47/10* (2013.01); *A61K 47/12* (2013.01); *A61K 47/14* (2013.01); *A61K 47/20* (2013.01); *A61K 47/44* (2013.01); *Y02A 50/473* (2018.01)

(58) Field of Classification Search
None
See application file for complete search history.

(56) References Cited

U.S. PATENT DOCUMENTS

| | | |
|---|---|---|
| 2,818,390 A | 12/1957 | Beaver |
| 3,048,266 A | 8/1962 | Hackhel et al. |
| 3,489,148 A | 1/1970 | Duncan et al. |
| 3,806,615 A | 4/1974 | Frankenfeld et al. |
| 3,983,214 A | 9/1976 | Misato et al. |
| 3,985,903 A | 10/1976 | Hasegawa |
| 4,002,775 A | 1/1977 | Kabara |
| 4,010,252 A | 3/1977 | Hewitt |
| 4,067,997 A | 1/1978 | Kabara |
| 4,113,854 A | 9/1978 | Andrews et al. |
| 4,160,820 A | 7/1979 | Wagenknecht |
| 4,189,481 A | 2/1980 | Kabara |
| 4,252,834 A | 2/1981 | Inamine et al. |
| 4,284,653 A | 8/1981 | Shigeoka et al. |
| 4,299,852 A | 11/1981 | Ueno et al. |
| 4,338,342 A | 7/1982 | Tan et al. |
| 4,364,929 A | 12/1982 | Sasmor |
| 4,485,029 A | 11/1984 | Kato et al. |
| 4,512,987 A | 4/1985 | Schindlery |
| 4,557,935 A | 12/1985 | af Ekenstam et al. |
| 4,597,975 A | 7/1986 | Woodward |
| 4,599,233 A | 7/1986 | Misato et al. |
| 4,648,876 A | 3/1987 | Becker et al. |
| 4,722,941 A | 2/1988 | Eckert et al. |
| 4,724,149 A | 2/1988 | Gul et al. |
| 4,840,738 A | 6/1989 | Hardy et al. |
| 4,894,220 A | 1/1990 | Nabi |
| 4,931,282 A | 6/1990 | Asmus et al. |
| 4,962,093 A | 10/1990 | Ohkawa et al. |
| 4,963,555 A | 10/1990 | Jones et al. |
| 4,980,163 A | 12/1990 | Blackburn et al. |
| 4,983,394 A | 1/1991 | Hussein et al. |
| 4,983,595 A | 1/1991 | Benjamin |
| 4,985,242 A | 1/1991 | Sekine |
| 4,997,851 A | 3/1991 | Isaacs et al. |
| 5,017,617 A | 5/1991 | Kihara |
| 5,084,096 A | 1/1992 | Stovicek |
| 5,093,140 A | 3/1992 | Watanabe |
| 5,098,694 A | 3/1992 | Komp et al. |
| 5,135,910 A | 8/1992 | Blackburn et al. |
| 5,145,685 A | 9/1992 | Carmody |

(Continued)

FOREIGN PATENT DOCUMENTS

| | | |
|---|---|---|
| AU | 16317/95 | 11/1995 |
| AU | 2000 49587 | 12/2000 |

(Continued)

OTHER PUBLICATIONS https://www.drugs.com/vet/3m-lauricare-moisturizing-teat-dip-concentrate.html referenced on Mar. 2, 2017.*

(Continued)

*Primary Examiner* — Jessica Worsham

(57) ABSTRACT

Antimicrobial compositions, especially those useful when applied topically, particularly to mucosal tissues (i.e., mucous membranes), including, in particular, an antimicrobial lipid component, such as a fatty acid ester, fatty ether, or alkoxide derivative thereof. The compositions can also include an enhancer component, a surfactant, a hydrophobic component, and/or a hydrophilic component. Such compositions provide effective topical antimicrobial activity and are accordingly useful in the treatment and/or prevention of conditions that are caused, or aggravated by, microorganisms (including viruses).

18 Claims, No Drawings

(56) References Cited

U.S. PATENT DOCUMENTS

| | | |
|---|---|---|
| 5,188,822 A | 2/1993 | Viccaro et al. |
| 5,192,802 A | 3/1993 | Rencher |
| 5,208,257 A | 5/1993 | Kabara |
| 5,217,950 A | 6/1993 | Blackburn et al. |
| 5,219,887 A | 6/1993 | Andrews et al. |
| 5,225,473 A | 7/1993 | Duan |
| 5,231,087 A | 7/1993 | Thornfeldt |
| 5,234,719 A | 8/1993 | Richter et al. |
| 5,260,271 A | 11/1993 | Blackburn et al. |
| 5,270,188 A | 12/1993 | Yamaguchi et al. |
| 5,304,540 A | 4/1994 | Blackburn et al. |
| 5,314,915 A | 5/1994 | Rencher |
| 5,318,955 A | 6/1994 | Mueller et al. |
| 5,320,772 A | 6/1994 | Tricca |
| 5,326,567 A | 7/1994 | Capelli |
| 5,334,582 A | 8/1994 | Blackburn et al. |
| 5,346,724 A | 9/1994 | Ohgake et al. |
| 5,362,555 A | 11/1994 | Lal |
| 5,364,650 A | 11/1994 | Guthery |
| 5,378,731 A | 1/1995 | Andrews et al. |
| 5,380,756 A | 1/1995 | Andrews et al. |
| 5,389,374 A | 2/1995 | Brown-Skrobot |
| 5,408,022 A | 4/1995 | Imazato |
| 5,429,819 A | 7/1995 | Oka |
| 5,434,182 A | 7/1995 | Isaacs et al. |
| 5,460,802 A | 10/1995 | Asami et al. |
| 5,460,833 A | 10/1995 | Andrews et al. |
| 5,462,749 A | 10/1995 | Rencher |
| 5,466,685 A | 11/1995 | Brown-Skrobot et al. |
| 5,482,931 A | 1/1996 | Harris |
| 5,490,992 A | 2/1996 | Andrews et al. |
| 5,516,510 A | 5/1996 | Beilfuss et al. |
| 5,516,536 A | 5/1996 | Mikkelsen et al. |
| 5,547,677 A | 8/1996 | Wright |
| 5,549,901 A | 8/1996 | Wright |
| 5,550,145 A | 8/1996 | Olund et al. |
| 5,569,461 A | 10/1996 | Andrews |
| 5,629,019 A | 5/1997 | Lee et al. |
| 5,641,503 A | 6/1997 | Brown-Skrobot |
| 5,656,591 A | 8/1997 | Tomita |
| 5,660,842 A | 8/1997 | Petschow |
| 5,665,776 A | 9/1997 | Yu et al. |
| 5,705,182 A | 1/1998 | Brown-Skrobot |
| 5,708,023 A | 1/1998 | Modak |
| 5,728,756 A | 3/1998 | Gaffar |
| 5,736,178 A | 4/1998 | Cook et al. |
| 5,736,574 A | 4/1998 | Burnier et al. |
| 5,747,069 A | 5/1998 | Asakura et al. |
| 5,753,252 A | 5/1998 | Brown-Skrobot |
| 5,759,584 A | 6/1998 | Traupe et al. |
| 5,762,948 A | 6/1998 | Blackburn |
| 5,804,549 A | 9/1998 | Blackburn et al. |
| 5,817,325 A | 10/1998 | Sawan |
| 5,862,949 A | 1/1999 | Markey et al. |
| 5,906,814 A | 5/1999 | Epstein |
| 5,945,110 A | 8/1999 | Vianen et al. |
| 5,951,993 A | 9/1999 | Scholz et al. |
| 5,955,502 A | 9/1999 | Hansen et al. |
| 5,965,088 A | 10/1999 | Lever et al. |
| 5,965,610 A | 10/1999 | Modak |
| 5,968,498 A | 10/1999 | Beerse et al. |
| 5,968,539 A | 10/1999 | Beerse et al. |
| 6,008,261 A | 12/1999 | Genova |
| 6,022,551 A | 2/2000 | Jampani et al. |
| 6,033,705 A | 3/2000 | Isaacs |
| 6,045,254 A | 4/2000 | Inbar et al. |
| 6,054,139 A | 4/2000 | Lambert et al. |
| 6,054,143 A | 4/2000 | Jones |
| 6,057,274 A | 5/2000 | Bator |
| 6,071,866 A | 6/2000 | Fujiwara |
| 6,089,389 A | 7/2000 | Sharon et al. |
| 6,090,075 A | 7/2000 | House |
| 6,093,417 A | 7/2000 | Petrus |
| 6,094,414 A | 7/2000 | Taira |
| 6,106,851 A | 8/2000 | Beerse et al. |
| 6,110,516 A | 8/2000 | Hoover et al. |
| 6,110,908 A | 8/2000 | Guthery |
| 6,113,933 A | 9/2000 | Beerse et al. |
| 6,121,327 A | 9/2000 | Tsuzuki |
| 6,121,329 A | 9/2000 | Fujii et al. |
| 6,123,933 A | 9/2000 | Hayama et al. |
| 6,165,494 A | 12/2000 | Picciano |
| 6,171,611 B1 | 1/2001 | Picciano |
| 6,177,071 B1 | 1/2001 | Lin et al. |
| 6,183,757 B1 | 2/2001 | Beerse et al. |
| 6,183,763 B1 | 2/2001 | Beerse et al. |
| 6,187,327 B1 | 2/2001 | Stack |
| 6,187,332 B1 | 2/2001 | Gern |
| 6,190,674 B1 | 2/2001 | Beerse et al. |
| 6,190,675 B1 | 2/2001 | Beerse et al. |
| 6,197,315 B1 | 3/2001 | Beerse et al. |
| 6,211,243 B1 | 4/2001 | Johnson |
| 6,214,866 B1 | 4/2001 | Drogemoller |
| 6,217,877 B1 | 4/2001 | Weidner |
| 6,224,898 B1 | 5/2001 | Balogh |
| 6,228,383 B1 | 5/2001 | Hansen et al. |
| 6,238,682 B1 | 5/2001 | Klofta |
| 6,258,368 B1 | 7/2001 | Beerse et al. |
| 6,278,008 B1 | 8/2001 | Endo et al. |
| 6,287,577 B1 | 9/2001 | Beerse |
| 6,294,186 B1 | 9/2001 | Beerse et al. |
| 6,319,895 B1 | 11/2001 | Tomita et al. |
| 6,352,727 B1 | 3/2002 | Takahashi |
| 6,375,984 B1 | 4/2002 | Kim |
| 6,383,523 B1 | 5/2002 | Murad |
| 6,403,069 B1 | 6/2002 | Chopra et al. |
| 6,414,023 B1 | 7/2002 | Brandsborg |
| 6,436,430 B1 | 8/2002 | Mulye |
| 6,440,405 B1 | 8/2002 | Cooper |
| 6,468,521 B1 | 10/2002 | Pedersen |
| 6,494,856 B1 | 12/2002 | Zygmont |
| 6,500,861 B1 | 12/2002 | Wider |
| 6,506,873 B1 | 1/2003 | Ryan et al. |
| 6,534,075 B1 | 3/2003 | Hei |
| 6,548,552 B1 | 4/2003 | Deresiewicz et al. |
| 6,555,566 B2 | 4/2003 | Ponikau |
| 6,559,189 B2 | 5/2003 | Baker, Jr. |
| 6,579,906 B2 | 6/2003 | Cooper |
| 6,590,051 B1 | 7/2003 | Carter et al. |
| 6,596,763 B1 | 7/2003 | Thormar et al. |
| 6,635,676 B2 | 10/2003 | Baker |
| 6,746,635 B2 | 6/2004 | Mathoiwitz et al. |
| 6,846,846 B2 | 1/2005 | Modak |
| 6,943,197 B2 | 9/2005 | Maibach et al. |
| 6,951,642 B2 | 10/2005 | Scholz et al. |
| 7,030,203 B2 | 4/2006 | Mosbey et al. |
| 7,569,530 B1 | 8/2009 | Pan et al. |
| 7,678,389 B1 | 3/2010 | Cordray |
| 7,858,662 B2 | 12/2010 | Chang |
| 2002/0013305 A1 | 1/2002 | Hanna |
| 2002/0025344 A1 | 2/2002 | Newman |
| 2002/0031556 A1 | 3/2002 | Lindahl |
| 2002/0037268 A1 | 3/2002 | Stack |
| 2002/0058010 A1 | 5/2002 | Picard-Lesboueyries |
| 2002/0086039 A1 | 7/2002 | Lee et al. |
| 2002/0193417 A1 | 12/2002 | Seidel |
| 2003/0147925 A1 | 8/2003 | Sawan |
| 2003/0152644 A1 | 8/2003 | Modak |
| 2003/0194447 A1 | 10/2003 | Scholz |
| 2003/0228376 A1 | 12/2003 | Mody |
| 2003/0235626 A1 | 12/2003 | Maibach et al. |
| 2004/0009130 A1 | 1/2004 | Detore |
| 2004/0052834 A1 | 3/2004 | West |
| 2004/0091428 A1 | 5/2004 | Libin |
| 2004/0126414 A1 | 7/2004 | Michaelis |
| 2004/0186183 A1 | 9/2004 | Johnson |
| 2004/0247685 A1 | 12/2004 | Modak et al. |
| 2004/0253139 A1 | 12/2004 | Denton |
| 2004/0265345 A1 | 12/2004 | Perricone |
| 2005/0019355 A1 | 1/2005 | Denton |
| 2005/0020678 A1 | 1/2005 | Denton |
| 2005/0053593 A1 | 3/2005 | Wang et al. |
| 2005/0058673 A1 | 3/2005 | Scholz |
| 2005/0089539 A1 | 4/2005 | Scholz |

(56) References Cited

U.S. PATENT DOCUMENTS

| | | |
|---|---|---|
| 2005/0112188 A1 | 5/2005 | Eliaz et al. |
| 2005/0118124 A1 | 6/2005 | Reinhart |
| 2005/0084471 A1 | 11/2005 | Andrews et al. |
| 2006/0029569 A1 | 2/2006 | Scholz et al. |
| 2006/0034798 A1 | 2/2006 | Mosbey et al. |
| 2006/0051384 A1 | 3/2006 | Scholz et al. |
| 2006/0051385 A1 | 3/2006 | Scholz |
| 2006/0052452 A1 | 3/2006 | Scholz |
| 2006/0099237 A1 | 5/2006 | Modak |
| 2006/0205838 A1 | 9/2006 | Velamakanni |
| 2006/0275349 A1 | 12/2006 | Andrews |
| 2006/0276541 A1 | 12/2006 | Tautvydas et al. |
| 2007/0020029 A1 | 1/2007 | Baumann |
| 2008/0142023 A1 | 6/2008 | Schmid |
| 2008/0287538 A1 | 11/2008 | Scholz |
| 2009/0005339 A1 | 1/2009 | Scholz |
| 2009/0186943 A1 | 7/2009 | Ikeda |
| 2009/0226541 A1 | 9/2009 | Scholz |
| 2010/0022654 A1 | 1/2010 | Asmus |

FOREIGN PATENT DOCUMENTS

| | | |
|---|---|---|
| CH | 634 749 | 2/1983 |
| DE | 43 02 812 | 8/1994 |
| DE | 43 19 546 | 12/1994 |
| DE | 196 42 127 | 4/1998 |
| DE | 10156794 | 6/2003 |
| DE | 101 61 885 | 7/2003 |
| DE | 10 2004 034691 | 2/2005 |
| EP | 0 104 346 | 4/1984 |
| EP | 0 131 393 | 1/1985 |
| EP | 0 156 563 | 10/1985 |
| EP | 0 172 724 | 2/1986 |
| EP | 0 191 217 | 8/1986 |
| EP | 0 243 145 | 10/1987 |
| EP | 0 244 144 | 11/1987 |
| EP | 0 253 535 | 1/1988 |
| EP | 0 272 149 | 6/1988 |
| EP | 0 312 519 | 4/1989 |
| EP | 0 375 827 | 7/1990 |
| EP | 0 455 370 | 11/1991 |
| EP | 0 465 423 | 1/1992 |
| EP | 0 483 835 | 5/1992 |
| EP | 0 489 967 | 6/1992 |
| EP | 0 497 607 | 8/1992 |
| EP | 0 530 861 | 3/1993 |
| EP | 0 547 727 | 6/1993 |
| EP | 0 567 704 | 11/1993 |
| EP | 0 245 928 | 1/1994 |
| EP | 0 608 433 | 8/1994 |
| EP | 0 629 347 | 12/1994 |
| EP | 0 876 768 | 11/1998 |
| EP | 0 937 812 | 8/1999 |
| EP | 1157685 | 11/2001 |
| EP | 1157686 | 11/2001 |
| ES | 2 095 183 | 1/1997 |
| FR | 2 729 050 | 7/1996 |
| GB | 2 053 195 | 2/1981 |
| GB | 2 193 892 | 2/1988 |
| GB | 2 323 784 | 10/1989 |
| GB | 2 338 649 | 12/1999 |
| JP | 72022252 | 9/1968 |
| JP | 51-15669 | 2/1976 |
| JP | 51-139645 | 2/1976 |
| JP | 76-84022 | 9/1976 |
| JP | 51106731 | 9/1976 |
| JP | 52-07428 | 1/1977 |
| JP | 52003859 | 1/1977 |
| JP | 77-22781 | 2/1977 |
| JP | 52-33181 | 8/1977 |
| JP | 77-73621 | 9/1977 |
| JP | 53-091126 | 8/1978 |
| JP | 79032058 | 10/1979 |
| JP | 56-43211 | 4/1981 |
| JP | 83018050 | 11/1981 |
| JP | 57176903 | 10/1982 |
| JP | 59-163477 | 9/1984 |
| JP | 60044539 | 3/1985 |
| JP | 85043111 | 9/1985 |
| JP | 61-152269 | 10/1986 |
| JP | 62-48612 | 3/1987 |
| JP | 63-130541 | 6/1988 |
| JP | 63-166837 | 7/1988 |
| JP | 1-256343 | 10/1989 |
| JP | 2-46255 | 2/1990 |
| JP | 02-116302 | 5/1990 |
| JP | 3067573 | 3/1991 |
| JP | 4016173 | 1/1992 |
| JP | 4018003 | 1/1992 |
| JP | 05 229915 | 9/1993 |
| JP | 05-320067 | 12/1993 |
| JP | 6022730 | 1/1994 |
| JP | 07-039356 | 2/1995 |
| JP | 8-40861 | 2/1996 |
| JP | 08-056631 | 3/1996 |
| JP | 8099878 | 4/1996 |
| JP | 8099887 | 4/1996 |
| JP | 08-175989 | 7/1996 |
| JP | 8-187070 | 7/1996 |
| JP | 8205771 | 8/1996 |
| JP | 9067593 | 3/1997 |
| JP | 10508337 | 8/1998 |
| JP | 11-113779 | 4/1999 |
| JP | 11113780 | 4/1999 |
| JP | 11302462 | 11/1999 |
| JP | 11-349418 | 12/1999 |
| JP | 3040282 | 5/2000 |
| JP | 2000-295976 | 10/2000 |
| JP | 2001 226205 | 8/2001 |
| JP | 2001 323298 | 11/2001 |
| JP | 2002-145736 | 5/2002 |
| JP | 2001-53564 | 9/2002 |
| JP | 2002-25571 | 9/2002 |
| JP | 2002-322090 | 11/2002 |
| KR | 9105620 | 8/1991 |
| WO | WO 82/03173 | 9/1982 |
| WO | WO 89/02754 | 4/1989 |
| WO | WO 89/12399 | 12/1989 |
| WO | WO 92/21320 | 12/1992 |
| WO | WO 93/15018 | 8/1993 |
| WO | WO 93/20812 | 10/1993 |
| WO | WO 93/21906 | 11/1993 |
| WO | WO 94/18943 | 9/1994 |
| WO | WO 94/27440 | 12/1994 |
| WO | WO 95/07616 | 3/1995 |
| WO | WO 95/24179 | 9/1995 |
| WO | WO 95-26134 | 10/1995 |
| WO | WO 95/31956 | 11/1995 |
| WO | WO 96/02228 | 2/1996 |
| WO | WO 96/25469 | 8/1996 |
| WO | WO 96/29867 | 10/1996 |
| WO | WO 97/00076 | 1/1997 |
| WO | WO 97/00163 | 1/1997 |
| WO | WO 97/11912 | 4/1997 |
| WO | WO 97/16168 | 5/1997 |
| WO | WO 97/23577 | 7/1997 |
| WO | WO 97/25032 | 7/1997 |
| WO | WO 98/09520 | 3/1998 |
| WO | WO 98/14189 | 4/1998 |
| WO | WO 99/11237 | 3/1999 |
| WO | WO 99/22703 | 5/1999 |
| WO | WO 99/37172 | 7/1999 |
| WO | WO 99/44444 | 9/1999 |
| WO | WO 99/45771 | 9/1999 |
| WO | WO 99/59538 | 11/1999 |
| WO | WO 99/60998 | 12/1999 |
| WO | WO 99/66793 | 12/1999 |
| WO | WO 00/01351 | 1/2000 |
| WO | WO 00/03612 | 1/2000 |
| WO | WO 00/04118 | 1/2000 |
| WO | WO 00/45771 | 8/2000 |
| WO | WO 00/69267 | 11/2000 |
| WO | WO 00/71183 | 11/2000 |
| WO | WO 00/71789 | 11/2000 |

(56) References Cited

FOREIGN PATENT DOCUMENTS

| WO | WO 00/78141 | 12/2000 |
|---|---|---|
| WO | WO2001/12155 | 2/2001 |
| WO | WO 01/24839 | 4/2001 |
| WO | WO 01/28552 | 4/2001 |
| WO | WO 01/43549 | 6/2001 |
| WO | WO 02/26261 | 4/2002 |
| WO | WO 02/47637 | 6/2002 |
| WO | WO2002/089849 | 11/2002 |
| WO | WO 02/100244 | 12/2002 |
| WO | WO 02/102244 A1 | 12/2002 |
| WO | WO 03/022211 | 3/2003 |
| WO | WO 03/028767 | 4/2003 |
| WO | WO 03-032948 | 4/2003 |
| WO | WO2003/037293 | 5/2003 |
| WO | WO03/047636 | 6/2003 |
| WO | WO2004/032927 | 4/2004 |
| WO | WO 04-052308 | 6/2004 |
| WO | WO2004/062643 | 7/2004 |
| WO | WO 2005-002482 | 1/2005 |
| WO | WO 2005/009353 | 2/2005 |
| WO | WO2005/022998 | 3/2005 |
| WO | WO2005/023233 | 3/2005 |
| WO | WO2005/102287 | 11/2005 |
| WO | WO 2006/026876 | 3/2006 |
| WO | WO 2006/029351 | 3/2006 |
| WO | WO 2007-094332 | 8/2007 |
| WO | WO 2008-057773 | 5/2008 |

OTHER PUBLICATIONS

Ahvenainen, "New approaches in improving the shelf life of minimally processed fruit and vegetables," *Trends in Food Science & Technology*, vol. 7, pp. 179-187 (Jun. 1996).
Baker et al., "Antimicrobial Properties of Lauricidin in Mechanically Deboned Chicken, Minced Fish and Chicken Sausage" *J. of Food Safety*, vol. 4, pp. 177-184 (1982).
Bell et al., "The Efficacy of Nisin, Sorbic Acid and Monolaurin as Perservatives in Pasteurized Cured Meat Products" *Food Microbiology*, vol. 4, pp. 277-283 (1987).
Block, S., "Acid-Anionic Surfactant Sanitizers", Disinfection, Sterilization and Preservation, Chapter 16, Lea & Febiger, Philidelphia PA, pp. 319-323 (1977).
Branen, J.K., et al., "Enhancement of nisin, lysozyme, and monolaurin antimicrobial activities by ethylenediaminetetraacetic acid and lactoferrin", *Intl Journal of Food & Microbiology*, vol. 90, No. 1, (Jan. 1, 2004) pp. 63-74 XP002316393.
Boddie, "Evaluation of postmilking teat germicides containing Lauricidin, saturated fatty acids and lactic acid", Journal of Dairy Science, Jun. 1992, vol. 75, No. 6, pp. 1725-1730. (XP002030991).
Berkow, The Merck Manual of Diagnosis and Therapy, 16th Edition, May 1, 1995, vol. 3, pp. 2228-2231.
Chavigny, "The Use of polymixin B as a urethral lubricant to reduce the post-instrumental incidence of bacteiuria in females. An exploratory sudy", Int. J. Nurs. Stud., 1975, vol. 12, pp. 33-42.
Clemons, "Evaluation of a Subcutaneously Implanted Chamber for Antibody Production in Rabbits", Laboratory Animal Science, Jun. 1992, vol. 42, No. 3, pp. 307-311.
Elliott, "Bladder Irrigation or Irritation?",British Journal of Urology, Oct. 1989, vol. 64, pp. 391-394.
European Search Report for Application No. Patent No. 11158066. 8-1219/2353587 (3M Ref. 58707EP016), dated Mar. 1, 2012.
Federal Register, 21 CFR Parts 333 and 369, Tentative Final Monograph for Healthcare Antiseptic Drug Products; Proposed Rule (1994).
Flournoy, et al., "The Role of Lauricidin as an Antimicrobil Agent" *Drugs of Today*, vol. 21 No. 8, pp. 373-377 (1985).
Gillespie, W.A., et al., "Prevention of Catheter Infection of Urine in Female Patients", *British Medical Journal*, pp. 13-16 (1962).
Gloor,"Triclosan, ein dermatologishes Lokaltherapeutikum", Hautarzt, Nov. 1, 2002,vol. 53, pp. 724-729. (XP002391035).

Gokalp,"Antimicrobial Screening of Mentha piperita Essential Oils", J. Agric Food Chem., 2002, vol. 50, pp. 3943-3946.
Hall et al., "Spice Extracts, Lauricidin, and Propylene Glycol as Inhibitors of Clostridium Botulinum in Turkey Frankfurter Slurries", *Poultry Science*, vol. 65, No. 6, pp. 1167-1171 (1986).
Hill,"The in-vitro activity of povidone-iodine cream against *Staphylococus aureas* and its bioavailability in nasal secretions", Journal of Hospital Infection,2000,vol. 45, pp. 198-205.
Izat et al., "The Use of Propylene Glycol and/or Lactic Acid in Chill Water for Reducing Salmoneallae on Broilers" *J. of Food Processing and Preservation*, vol. 14, pp. 369-374 (1990).
Kabara, "GRAS Antimicrobial Agents for Cosmetic Products", *J. Soc. Cosmet. Chem.* vol. 31, pp. 1-10 (1980).
Kabara, "Food-Grade Chemicals for Use in Designing Food Preservative Systems", *J. of Food Protection*, vol. 44, pp. 633-647 (1981).
Kabara, A New Preservative System for Food, *J. of Food Safety*, vol. 4, pp. 13-25 (1982).
Kabara, "Medium-Chain Fatty Acids and Esters as Antimicrobial Agents" *Cosmetic and Drug Preservation*, vol. 16, pp. 275-304 (1984).
Kabara, J.J., et al. "Antimicrobial Lipids: Natural and Synthetic Fatty Acids and Monoglycerides", Lipids, Champaign, IL, vol. 12, No. 9, (Sep. 1, 1977) pp. 753-759 XP000563038.
Kato et al., "Combined Effect on Different Drugs on the Antibacterial Activity of Fatty Acids and their Esters", vol. 4, pp. 355-363 (1975).
Kato, et al., "Combined Effect of Citric and Polyphosphoric Acid on the Antibacterial Activity of Monoglycerides", vol. 4, No. 6 pp. 254-261 (1976).
Keresteci, "Indwelling catheter infection", Canadian Medical Association Journal, Oct. 20, 1973, vol. 109, pp. 711-713.
Kida, "Effect of pH on preferential Antibacterial-activity of Ethylenediaminetetraacetic acid (EDTA)", Japanese Journal of Bacteriology, Jul. 1992, vol. 47, No. 4, pp. 625-629.
Kiser, K. et al., "Development and Characterization of *Staphylococcus aureus* Nasal Colonization Model in Mice," *Infect and Immunity*, vol. 67, No. 10, pp. 5001-5006 (1999).
Kostiala, A.A.I., et al., "Effect of nitrofurantoin and methenamine hippurate prophylaxis on bacteria and yeasts in the urine of patients with an indwelling catheter", *J. of Hospital Infection*, vol. 3, pp. 357-364 (1982).
Macfarlane, D.E., "Prevention and treatment of catheter-associated urinary tract invections", *J. of Infection*, vol. 10, pp. 96-106 (1985).
"Mannose may be useful for treating uterine infections" [retrieved from the internet on Apr. 9, 2003], URL http://www.equinescienceupdate.co.uk/mannos.htm, 2 pages.
Mannose may be useful for treating uterine infections [retrieved from the internet on Nov. 18, 2008], URL http://www.equinescienceupdate.co.uk/mannos.htm.
May,"Time-kill studies of tea tree oils on clinical isolates", Journal of Antimicrobial Chemotherapy, 2000,vol. 45, pp. 639-643.
Mead et al., "Food-Related Illness and Death in the United States", *Emerg. Infect. Dis.*, vol. 5, No. 5, pp. 607-625 (1999).
Medical Digest, May 1991, vol. 40, No. 3, pp. 2-6.
Merianos, Disinfection, Sterilization, and Preservation, "Quaternary Ammonium Antimicrobial Compounds", 4th Ed. Chapter 13, pp. 225-255 (1991).
Merriam-Webster's Collegiate Dictionary, 924 (1998).
Morgan, D. M., "Urinary tract infection in hospitalized patients", *Canadian Hospital*, pp. 27-30 (1973).
Morizono, Safety of Antimicrobials Applied in the Middle Ear Cavity, Aurinasal Clinic, Practica. Oto.rhino.laryngologica. Suppl., 2002, vol. 95, No. 7, pp. 663-669.
Nakagaki, et al., "Solubility & Hydrolysis Rate of I-Monolaurin in Aqueous Solutions", *Yakugaku Zasshi*, vol. 90, No. 10, pp. 1310-1315 (1970).
Nicoletti, G. et al., The Antimicrobial Activity in vitro of chlorhexidine, a mixture of isothiazolinones (Kathon CG) and cetyl trimethyl ammonium bromide (CTAB), *Journal of Hospital Infection*, vol. 23, pp. 87-111 (1993).

(56) References Cited

OTHER PUBLICATIONS

NutritionalTest.com, 10105 E Via Linda #103-192, Scottsdale, AZ 85258. Take the guess work out of taking nutrients, D. Mannose [retrieved from the internet on Nov. 18, 2008], URL <http://www.nutritionaltest.com/dmannose.html>.

Oh, et al., "Enhanced Inhibition of *Listeria monocytogenes* by Glycerol Monolaurate with Organic Acids", *Journal of Food Science*, vol. 59, No. 6, pp. 1258-1261 (1994).

Osborne, "Skin Penetration Enhancers, cited in Technical literature", Pharmaceutical Technology, Nov. 1997, pp. 58-66.

Perez-Roth, E. et al. "Mupirocin resistance in methicillin-resistant *Staphylococcus aureus* clinical isolates in a Spanish hospital. Co-application of multiplex PCR assay and conventional microbiology methods", *Diag. Micro. Infect. Dis.*, vol. 43, pp. 123-128 (2002).

Perl, T. et al., "New Approaches to Reduce *Staphylococcus aureua* Nosocomial Infection Rates: Treating *S. aureus* Nasal Carriage", *Ann. Pharmacother.*, vol. 32, pp. S7-S16 (1998).

Physicians' Desk Reference, To Pharmaceutical Specialties and Biologicals, 26th Edition, 628 (1972).

Physician's Desk Reference, definition of the composition of Aquaphor, p. 685, 1993 Edition.

Product Information Brochure, Sensive SC 50 a multifunctional additive, Schuelke & Mayer (16 pgs.).

Projan, et al., "Glycerol Monolaurate Inhibits the Production of β-Lactamase, Toxic Shock Syndrom Toxin-1, and Other Staphylococal Exoproteins by Interfering with Signal Transduction" *Journal of Bacteriology*, vol. 176, No. 14, pp. 4204-4209 (Jul. 1994).

"Propylene Glycol" Technical Data [online], Lyondell Chemical Company, Houston, TX, 2006 <http://www.lyondell.com/Lyondell/techlit/techlit/2514.pdf>, 1 pg. (Exhibit A).

Remington's Pharmaceutical Services, definition of absorption base, 14th Ed., p. 1600 (1970).

Respiratory mucosa: the core of infection and inflammation, Title page, Editorial page, pp. 1-32, Product information page, and Publication page (36 pgs. Total).

"Rezepturhinweise: Triclosan in Dermatika", NRF—Neues Rezeptur Formularium, ABDA, Apr. 16, 2004, pp. 1-4. ( XP002391034).

Rice, J. "Organic acid sprays," *Food Processing*, pp. 45, 47-48, 50 (Apr. 1994).

Rutala et al, "Susceptibility of Antibiotic-Auaceptibke and Antibiotic-Resistant Hospital Bacteria to Disinfectants", Infection Control and Hospital Epidemiology Jun. 1997, vol. 18, No. 6, pp. 417-421.

Sawhney, A.S. et al., "Bioerodible Hydrogels Based on Photopolymerized Poly(ethylene glycol)-co-poly(a-hydroxy acid) Diacrylate Macromers", *Macromolecules*, vol. 26, pp. 581-587 (1993).

Schemmel et al., "Monolaurin as an Anticaries Agent", Chapter 4, *Symposium on the Pharmacological Effect of Lipds*, pp. 37-43 (1983).

Schlievert, "Effect of glycerol monolaurate on bacterial growth and toxin production",Antimicrobial Agents Chemotherapy, Mar. 1992, vol. 36, No. 3, pp. 626-631.

Schneeberger, "A randomized study on the effect of bladder irrigation with povidone-iodine before removal of an indwelling catheter", Journal of Hospital Infection, Jul. 1992, vol. 21, No. 3, pp. 223-229.

Sciarra and Cutie, "Aersols," *Chapter 92 in Remington's Pharmaceutical Sciences*, 18th edition, pp. 1694-1712 (1990).

Silverman, Disinfection, Sterilization, and Preservation, "The Destruction of Microorganisma by Ionizing Irradiation" First Edition, pp. 742-760 (1968).

Stecker, Disinfection, Sterilization, and Preservation,"The Salicylanilides and Carbanilides", 2nd Edition, Chapter 14, pp. 282-300 (1977).

Stillman,"Relative irritancy of free fatty acids of different chain length," Contact Dermatitis, 1975, vol. 1, No. 2, pp. 65-69.

Tanaka, "Antibacterial Compounds From Nutmeg Against Upper Airway Respiratory Tract Bacteris", ITE Letters on Batteries, New Technologies and Medicine, 2000, vol. 1, No. 3, pp. 412-417.

The Merck Manual of Diagnosis and Therapy, Seventeenth Edition, 673-677 (1999).

Vadehra et al., "Comparison of Antibacterial Properties of Lauricidin® and BHA against Antibotic Resistant and Sensitive Strains of *Staphylococcus aureus* and *Pseudomonos aeruginosa" AOCS Monograph* vol. 13, No. 2, pp. 77-87, XP000560207 (1985).

Van Putten,"Mandelic acid and urinary tract infections"; Antonie van Leeuwenhoek, International Journal of General and Molecular Microbiology,1979,vol. 45, No. 4, pp. 622.

VanDen Broek et al., "Bladder Irrigation with Povidone-Iodine in Prevention of Urinary-Tract Infections associated with Intermittent Urethral Catheterisation," The Lancet, Mar. 9, 1985;563-565.

Venkitanarayanan et al., "Inactivation of *Escherichia coli* 0157:H7 by combinations of GRAS chemicals and temperature", *Food Microbiology*, vol. 16, pp. 75-82 (1999).

"Viscosity of Aqueous Glycerine Solutions in Centipoises/mPa s, " [online]. Dow Chemical Company, Midland, MI, Nov. 1999, http://www.dow.com/PublishedLiterature/dh_0032/0901b80380322bd.pdf?filepath=glycerine/pdfs/noreg/115-00678.pdf&fromPage=GetDoc.)>. 1 pg. (Exhibit B).

Vorum, H. et al., "Solubility of Long-Chain Fatty Acids in Phosphate Buffer at pH 7.4," *Biochimica et. Biophysica Acta*, vol. 1126, pp. 135-142 (1992).

Wakabayashi, et al., Increased *Staphylococcus*-killing Activity of an Antimicrobial Peptide, Lactoferricin B, with Minocycline and Monoacylglyserol, *Bioscience Biotechnology and Biochemistry* vol. 66, No. 10, pp. 2161-2167 (Oct. 2002).

Wang et al., "Inhibition of *Listeria monocytogenes* by Monoacylglycerols Synthesized from Coconut Oil and Milkfat by Lipase-Catalzed Glycerolysis" *J. of Agric. Food Chem.*, vol. 41, pp. 1000-1005 (1993).

Watanabe, H. et al., "Low Concentrations of Mupirocin in the Pharynx following Intranasal Application May Conrtibute to Mupirocin Resistance in Methicillin-Resistant *Staphylococcus aureus*," J. Clin. Micro., vol. 39, No. 10 pp. 3775-3777 (2001).

Whitley, et al., "Herpes zoster: focus on treatment in older adults", *Antiviral Research* vol. 44, pp. 145-154 (1999).

Williams, "Trials of Five Antibacterial Creams in the Control of Nasal Carriage of *Staphylococcus aureus*", The Lancet, Aug. 19, 1967, vol. 290, No. 7512, pp. 390-392.

Williamson et al., "A New Method for the Quantitative Investigation of Cutaneous Bacteria," *J. Invest. Derm.*, vol. 45, pp. 498-503 (1965).

Wooley, "EDTA-tris Potentiation of Antimicrobial Agents", *Modern Veterinary Practice*, pp. 113-116 (1983).

Wright,,"Middle Ear Effects of Ototopical Agents", Ototoxicity,107-113 (2004).

http://www.lungusa.org/site/pp.asp?c=dvLUK9O0E&b=35873.

http://www.merck.com/mmhe/sec06/ch089/ch089d.html.

\* cited by examiner

ANTIMICROBIAL COMPOSITIONS AND METHODS

CROSS REFERENCE TO RELATED APPLICATIONS

This application is a continuation of U.S. application Ser. No. 10/937,059, filed Sep. 8, 2004, now pending, which is a continuation-in-part of U.S. application Ser. No. 10/659,571, filed Sep. 9, 2003, which is now abandoned, the disclosure of which is incorporated by reference in their entirety herein.

BACKGROUND

The use of antimicrobial agents (e.g., antibiotics, antiseptics) plays an important part in current medical therapy. This is particularly true in the fields of dermatology as well as skin and wound antisepsis, where the most effective course of treatment for skin or mucous membranes (e.g., as in the nasal cavities and in particular the anterior nares), which are afflicted with bacterial, fungal, or viral infections or lesions, frequently includes the use of a topical antimicrobial agent. For decades medicine has relied primarily upon antibiotics to fight systemic as well as topical infections. For example, bacitracin, neomycin sulfate, polymyxin B sulfate, gentamicin, framycetin-gramicidin, lysostaphin, methicillin, rifampin, tobramycin, nystatin, mupirocin, and combinations thereof, as well as many others, have been used with varying success.

Antibiotics are generally effective at very low levels and are often safe with very few, if any, side effects. Often antibiotics have little or no toxicity to mammalian cells. Thus, they may not retard, and can even enhance, wound healing. Antibiotics are generally of a narrow spectrum of antimicrobial activity. Furthermore, they often act on very specific sites in cell membranes or on very specific metabolic pathways. This can tend to make it relatively easy for bacteria to develop resistance to the antibiotic(s) (i.e., the genetically acquired ability to tolerate much higher concentrations of antibiotic) either through natural selection, transmission of plasmids encoding resistance, mutation, or by other means.

For example, there are multiple reports of resistance to mupirocin when used as a nasal decolonizing agent. Resistance rates have been reported as high as 25% and even as high as 50% (see, for example, E. Perez-Roth et al., *Diag. Micro. Infect. Dis.*, 43:123-128 (2002) and H. Watanabe et al., *J. Clin. Micro.*, 39(10): 3775-3777 (2001)). Even though presurgical decolonization of the anterior nares using mupirocin has been shown to decrease the risk of surgical site infection by as much as 2 to 10 times (T. Perl et al., *Ann. Pharmacother.*, 32:S7-S16 (1998)), the high resistance rates to this antibiotic make it unsuitable for routine use. Not only does resistance eliminate the ability of a medication to treat an affliction, but it can also put the patient at further risk, especially if the antibiotic is one that is routinely used systemically.

Antiseptics, on the other hand, tend to have broader spectrum of antimicrobial activity and often act by nonspecific means such as disruption of cell membranes, oxidation of cellular components, denaturation of proteins, etc. This nonspecific activity makes it difficult for resistance to develop to antiseptics. For example, there are very few reports of true resistance to antiseptics such as iodine, lower alcohols (ethanol, propanol, etc.), chlorhexidine, quaternary amine surfactants, chlorinated phenols, and the like. These compounds, however, need to be used at concentrations that often result in irritation or tissue damage, especially if applied repeatedly. Furthermore, unlike antibiotics, many antiseptics are not active in the presence of high levels of organic compounds. For example, formulations containing iodine or quaternary ammonium compounds have been reported to be inactivated by the presence of organic matter such as that in nasal or vaginal secretions, and perhaps even on skin.

Many antiseptic compounds are viewed as irritants. For example, compositions containing iodine and/or chlorhexidine have been reported to cause skin irritation. Mucosal tissues, such as the anterior nares, nasal, and esophageal cavities, which can have a high level of microbial colonization in certain otherwise healthy individuals, as well as individuals with infectious diseases such as chronic sinusitis, may be particularly sensitive to irritation. Additionally, due to the irritating nature many of these compounds may be unsuitable for application to irritated or infected dermal tissue to treat skin conditions, such as lesions from impetigo and shingles.

Also, for certain applications, especially in the nose and mouth, it is particularly desirable for the compositions to have little or no color, little or no odor, and an acceptable taste. This is not the case for many antiseptics such as iodine and iodophors, which have an orange to brown color and a definite odor.

Some conventional antimicrobial compositions have used various carboxylic acids or fatty acids for the suppression of fungi, bacteria, molds, and the like. These compositions vary widely in their efficacy, stability, and levels of persistence. Plus, they possess an even wider variety of side effects. For example, many of these materials are viewed as irritants, particularly the C8-C12 fatty acids. This is particularly true for sensitive mucosal tissues, such as the anterior nares and nasal cavities, which can have a generally high level of microbial colonization in certain otherwise healthy individuals, as well as individuals with infectious diseases such as chronic siniusitis. Additionally, due to the irritating nature many of these agents would be unsuitable for application to irritated or infected dermal tissue such as lesions from impetigo and shingles or sensitive tissues such as the nasal cavities and especially the anterior nares.

Also, many conventional antimicrobial compositions are too low in viscosity and/or too hydrophilic in nature to maintain sufficient substantivity and persistence to provide sufficient antimicrobial activity on moist tissue, such as the anterior nares or open, exuding, or infected lesions, and the like.

Thus, there is still a need for additional antimicrobial compositions.

SUMMARY OF THE INVENTION

The present invention provides antimicrobial compositions and methods of using and making the compositions. Such compositions are typically useful when applied topically, particularly to mucosal tissues (i.e., mucous membranes), although a wide variety of surfaces can be treated. They can provide effective reduction, prevention, or elimination of microbes, particularly bacteria, fungi, and viruses. Preferably, the microbes are of a relatively wide variety such that the compositions of the present invention have a broad spectrum of activity.

Compositions of the present invention provide effective topical antimicrobial activity and are accordingly useful in the local treatment and/or prevention of conditions that are caused, or aggravated by, microorganisms (including viruses, bacteria, fungi, mycoplasma, and protozoa) on various mammalian tissues, particularly skin, wounds, and/or mucous membranes.

Significantly, certain embodiments of the present invention have a very low potential for generating microbial resistance. Thus, such compositions can be applied multiple times over one or more days to treat topical infections or to eradicate unwanted bacteria (such as nasal colonization of *Staphylococcus aureus*). Furthermore, compositions of the present invention can be used for multiple treatment regimens on the same patient without the fear of generating antimicrobial resistance. This can be particularly important for chronically ill patients who are in need of decolonization of the anterior nares before hemodialysis, for example, or for antiseptic treatment of chronic wounds such as diabetic foot ulcers.

Also, preferred compositions of the present invention have a generally low irritation level for skin, skin lesions, and mucosal membranes (including the anterior nares, nasal cavities, and nasopharangyl cavity). Also, certain preferred compositions of the present invention are substantive for relatively long periods of time to ensure adequate efficacy.

Compositions of the present invention include an antimicrobial lipid component. In certain embodiments, the antimicrobial lipid (i.e., antimicrobial lipid component) preferably has a solubility in water of at least 100 micrograms (μg) per 100 grams (g) deionized water and at most 1 g/100 g deionized water. In certain embodiments, the antimicrobial lipid component includes a fatty acid ester of a polyhydric alcohol, a fatty ether of a polyhydric alcohol, alkoxylated derivatives thereof (of either the ester or ether), or combinations thereof.

Certain compositions further include an enhancer component (i.e., an enhancer). Other components that can be included as well are surfactants, hydrophilic components, and hydrophobic components. Compositions with hydrophobic components are typically used on mammalian tissues (particularly, skin, mucosal tissue, wounds and medical devices that come in contact with such surfaces, whereas compositions with hydrophilic components are typically used on these surfaces as well as other hard surfaces (e.g., floor tiles).

Importantly, compositions of the present invention are capable of destroying microorganisms on or in mammalian tissue. Therefore, concentrations of components employed are generally greater than those that have been used to simply preserve certain topically applied compositions, i.e., prevent the growth of microorganism in topical compositions for purposes other than antisepsis. Depending on the application, many of these compounds at these concentrations can be irritating if delivered in simple aqueous or hydrophilic vehicle formulations. Many of the compositions of the present invention incorporate a substantial amount of a lipophilic or hydrophobic phase. The lipophilic phase is comprised of one or more water insoluble components. If delivered in a lipophilic phase, the irritation can be significantly reduced. The incorporation of the lipophilic phase may significantly reduce the irritation potential of the present compositions. Preferred lipophilic phase components have a solubility in water of less than 0.5% by weight and often less than 0.1% by weight. In addition, the antimicrobial lipid is preferably present at a concentration approaching or preferably exceeding the solubility limit of the lipophilic phase.

Importantly, certain compositions of the present invention have sufficient viscosity to prevent inhalation into the lungs if used in the nose for applications such as nasal decolonization. The relatively high viscosity of certain compositions of the present invention also reduces migration that can be associated with other compositions, thus reducing irritation and mess. Despite the presence of the hydrophobic phase, compositions of the present invention exhibit very effective and rapid antimicrobial activity.

In addition, antimicrobial compositions that include hydrophilic components such as polyols (e.g., glycerin and polyethylene glycols) that themselves have little or no antimicrobial activity can considerably enhance the antimicrobial activity of the compositions.

In one embodiment, the present invention provides an antimicrobial composition that includes: an effective amount of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12) aralkyl carboxylic acid, a (C6-C12)alkaryl carboxylic acid, a phenolic compound, a (C1-C10)alkyl alcohol, an ether glycol, or combinations thereof; a surfactant distinct from the antimicrobial lipid component; a hydrophilic component; and a hydrophobic component; wherein the hydrophobic component forms the greatest portion of the composition. Preferably, water is present in less than 10 percent by weight (wt-%).

In one embodiment, the present invention provides an antimicrobial composition that includes: 0.01 wt-% to 20 wt-% of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; 0.01 wt-% to 20 wt-% of an enhancer component that includes an alpha-hydroxy acid, a beta-hydroxy acid, a chelating agent, a (C1-C4)alkyl carboxylic acid, a (C6-C12)aryl carboxylic acid, (C6-C12) aralkyl carboxylic acid, a (C6-C12)alkaryl carboxylic acid, a phenolic compound, a (C1-C10)alkyl alcohol, an ether glycol, or combinations thereof; 0.1 wt-% to 10 wt-% of a surfactant distinct from the antimicrobial lipid component; 1 wt-% to 40 wt-% of a hydrophilic component; 50 wt-% to 95 wt-% of a hydrophobic component; and less than 10 wt-% water.

In one embodiment, the present invention provides an antimicrobial composition that includes: an effective amount of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof; a surfactant distinct from the antimicrobial lipid component; and a hydrophilic component; wherein the viscosity of the composition is at least 500 Centipoise (cps).

In one embodiment, the present invention provides an antimicrobial composition that includes: an effective amount of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof; a surfactant distinct from the antimicrobial lipid component; a hydrophilic component; a hydrophobic component; and less than 10 wt-% water; wherein the hydrophilic component forms the greatest portion of the composition by weight.

In one embodiment, the present invention provides an antimicrobial composition that includes: an effective amount of an antimicrobial lipid component that includes a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the ethers include monoethers, and for sucrose the ethers include monoethers, diethers, or combinations thereof; an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof; and a hydrophobic component which forms the greatest portion of the composition by weight.

In one embodiment, the present invention provides an antimicrobial composition that includes: an effective amount of an antimicrobial lipid component that includes a (C7-C12)saturated fatty ether of a polyhydric alcohol, a (C8-C22)unsaturated fatty ether of a polyhydric alcohol, an alkoxylated derivative thereof, and combinations thereof, wherein the alkoxylated derivative has less than 5 moles of alkoxide per mole of polyhydric alcohol; with the proviso that for polyhydric alcohols other than sucrose, the ethers include monoethers, and for sucrose the ethers include monoethers, diethers, or combinations thereof; an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof; and a hydrophilic component which forms the greatest portion of the composition; wherein the viscosity of the composition is at least 500 cps.

In one embodiment, the present invention provides an antimicrobial composition that includes: an effective amount of an antimicrobial lipid having a solubility in water of at least 100 μg/100 g deionized water and at most 1 g/100 g deionized water; an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof; a surfactant distinct from the antimicrobial lipid component; a hydrophilic component; and a hydrophobic component which forms the greatest portion of the composition.

In one embodiment, the present invention provides an antimicrobial composition that includes: an effective amount of an antimicrobial lipid component having a solubility in water of at least 100 μg/100 g deionized water and at most 1 g/100 g deionized water; an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof; and a hydrophilic component which forms the greatest portion of the composition; wherein the viscosity of the composition is at least 500 cps.

In one embodiment, the present invention provides a delivery system for an antimicrobial component (e.g., antiseptic component) including a hydrophobic component and a hydrophilic component, wherein the composition has a viscosity of at least 500 cps, and further wherein the hydrophobic component forms the greatest portion of the composition by weight. In an additional embodiment, the present invention provides a delivery system for an antimicrobial component (e.g., antiseptic component) including a hydrophobic component, a hydrophilic component, and a surfactant, wherein the hydrophobic component forms the greatest portion of the composition by weight. In certain embodiments, such delivery systems can include an antimicrobial lipid component (and/or other antiseptics).

In another embodiment, the present invention provides a method for delivering an antimicrobial component (e.g., antiseptic component), the method includes applying to a surface a composition that includes a hydrophobic component and a hydrophilic component, wherein the composition has a viscosity of at least 500 cps, and further wherein the hydrophobic component forms the greatest portion of the composition by weight. In an additional embodiment, the present invention provides a method for delivering an antimicrobial component (e.g., antiseptic component), the method includes applying to a surface a composition that includes a hydrophobic component, a hydrophilic component, and a surfactant, wherein the hydrophobic component forms the greatest portion of the composition by weight. In certain embodiments, such delivery systems can include an antimicrobial lipid component (and/or other antiseptics).

Preferably, the antimicrobial lipid component is present in an amount of at least 0.1 wt-%. Unless otherwise specified, all weight percents are based on the total weight of a "ready to use" or "as used" composition. Preferably, if the antimicrobial lipid component includes a monoester of a polyhydric alcohol, a monoether of a polyhydric alcohol, or an alkoxylated derivative thereof, then there is no more than 50 wt-%, more preferably no more than 40 wt-%, even more preferably no more than 25 wt-%, and even more preferably no more than 15 wt-% of a diester, diether, triester, triether, or alkoxylated derivative thereof present, based on the total weight of the antimicrobial lipid component.

Preferably, the antimicrobial lipid component includes glycerol monolaurate, glycerol monocaprate, glycerol monocaprylate, propylene glycol monolaurate, propylene glycol monocaprate, propylene glycol monocaprylate, and combinations thereof.

In certain embodiments, the enhancer component preferably includes a carboxylic acid. In certain embodiments, the enhancer component preferably includes an alpha-hydroxy acid. In certain embodiments, the enhancer component preferably includes benzoic acid. In certain embodiments, the enhancer component preferably includes a chelator. In certain embodiments, the enhancer component preferably includes EDTA and its salts.

Preferably, the surfactant includes a sulfonate, a sulfate, a phosphonate, a phosphate, a poloxamer, a cationic surfactant, or mixtures thereof.

Preferably, the hydrophilic component includes a glycol, a lower alcohol ether, a short chain ester, and combinations thereof, wherein the hydrophilic component is soluble in water in an amount of at least 20 wt-% at 23° C.

The present invention also provides various methods of use of compositions of the present invention. In one embodiment, the present invention provides a method of preventing and/or treating an affliction caused, or aggravated by, a microorganism on mammalian tissue, particularly skin and/or a mucous membrane. The method includes contacting the mammalian tissue, particularly skin and/or mucous membrane, with an antimicrobial composition of the present invention.

In one embodiment, the present invention provides a method of decolonizing at least a portion of the nasal cavities, anterior nares, and/or nasopharynx of a subject of microorganisms. The method includes contacting the nasal cavities, anterior nares, and/or nasopharynx with an antimicrobial composition of the present invention in an amount effective to kill one or more microorganisms.

In one embodiment, the present invention provides a method of decolonizing at least a portion of the nasal cavities, anterior nares, and/or nasopharynx of a subject of microorganisms. The method includes contacting the nasal cavities, anterior nares, and/or nasopharynx with an antimicrobial composition in an amount effective to kill one or more microorganisms, wherein the antimicrobial composition includes: an effective amount of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; optionally, an effective amount of an enhancer component that includes an alpha-hydroxy acid, a beta-hydroxy acid, a chelating agent, a (C1-C4)alkyl carboxylic acid, a (C6-C12) aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof; a hydrophobic component which forms the greatest portion of the composition by weight; and optionally, a hydrophilic component.

In one embodiment, the present invention provides a method of decolonizing at least a portion of the nasal cavities, anterior nares, and/or nasopharynx of a subject of microorganisms, the method including contacting the nasal cavities, anterior nares, and/or nasopharynx with an antimicrobial composition in an amount effective to kill one or more microorganisms, wherein the antimicrobial composition includes: an effective amount of an antimicrobial lipid component having a solubility in water of at least 100 µg/100 g deionized water and at most 1 g/100 g deionized water; and a hydrophobic component which forms the greatest portion of the composition by weight.

In one embodiment, the present invention provides a method of decolonizing at least a portion of the throat/esophagus of a subject of microorganisms. The method includes contacting the esophageal cavity with an antimicrobial composition of the present invention in an amount effective to kill one or more microorganisms in or on the tissue in the throat.

In one embodiment, the present invention provides a method of decolonizing at least a portion of the throat/esophagus of a subject of microorganisms. The method includes contacting the oral cavity, nasal cavity, or both with an antimicrobial composition of the present invention in an amount effective to allow a sufficient quantity of the composition to pass down the throat to reduce or eliminate bacterial colonization in or on the tissue in the throat.

In one embodiment, the present invention provides a method of decolonizing at least a portion of the oral cavity of a subject of microorganisms. The method includes contacting the oral cavity with an antimicrobial composition of the present invention in an amount effective to kill one or more microorganisms in or on the soft tissue in the oral cavity.

In one embodiment, the present invention provides a method of treating a middle ear infection in a subject. The method includes contacting the middle ear, Eustachian tube, and/or tympanic membrane with an antimicrobial composition that includes: an effective amount of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; and an effective amount of an enhancer component that includes an alpha-hydroxy acid, a beta-hydroxy acid, a chelating agent, a (C1-C4)alkyl carboxylic acid, a (C6-C12) aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof. An alternative composition for treating a middle ear infection includes an effective amount of an antimicrobial lipid component, optionally an effective amount of an enhancer component, and a hydrophobic component which forms the greatest portion of the composition by weight (i.e., the hydrophobic component forms a vehicle for the active agent(s)). In certain embodiments, the hydrophobic component can be the same as the antimicrobial lipid.

In one embodiment, the present invention provides a method of treating a middle ear infection in a subject, the method including contacting the middle ear, tympanic membrane, and/or Eustachian tube with an antimicrobial composition that includes: an effective amount of an antimicrobial lipid component having a solubility in water of at least 100 µg/100 g deionized water and at most 1 g/100 g deionized water; and an effective amount of an enhancer component comprising an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof.

In one embodiment, the present invention provides a method of treating chronic sinusitis in a subject. The method includes contacting at least a portion of the respiratory system (particularly the upper respiratory system including the nasal cavities, anterior nares, and/or nasopharynx) with an antimicrobial composition that includes: an effective amount of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; and an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12) aralkyl carboxylic acid, a (C6-C12)alkaryl carboxylic acid, a phenolic compound, a (C1-C10)alkyl alcohol, an ether glycol, or combinations thereof. Preferably, the composition includes less than 0.50 percent by weight (C6-C18)fatty acid. An alternative composition for treating chronic sinusitis includes an effective amount of an antimicrobial lipid component, optionally an effective amount of an enhancer component, and a hydrophobic component, which forms the greatest portion of the composition by weight. Yet another composition includes: an effective amount of an antimicrobial lipid component having a solubility in water of at least 100 µg/100 g deionized water and at most 1 g/100 g deionized water; and a hydrophobic component which forms the greatest portion of the composition by weight.

In one embodiment, the present invention provides a method of treating impetigo on the skin of a subject. The method includes contacting the affected area with an antimicrobial composition that includes: an effective amount of an antimicrobial lipid component that includes a (C7-C12) saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12) aralkyl carboxylic acid, a (C6-C12)alkaryl carboxylic acid, a phenolic compound, a (C1-C10)alkyl alcohol, an ether glycol, or combinations thereof. Preferably, the composition includes a hydrophilic component and the viscosity of the composition is less than 500 cps. An alternative composition for treating impetigo includes an effective amount of an antimicrobial lipid component, optionally an effective amount of an enhancer component, and a hydrophobic component, which forms the greatest portion of the composition by weight. Yet another composition for treating impetigo includes: an effective amount of an antimicrobial lipid component having a solubility in water of at least 100 µg/100 g deionized water and at most 1 g/100 g deionized water; and an effective amount of an enhancer component comprising an alpha-hydroxy acid, a beta-hydroxy acid, a chelating agent, a (C1-C4)alkyl carboxylic acid, a (C6-C12) aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof.

In one embodiment, the present invention provides a method of treating and/or preventing an infection on mammalian tissue (particularly, the skin, mucosal tissue, and/or wound) of a subject. The method includes contacting the mammalian tissue (particularly, skin, mucosal tissue, and/or wound) with an antimicrobial composition in an amount effective to kill or inactivate one or more microorganisms, wherein the antimicrobial composition includes: an effective amount of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12) aralkyl carboxylic acid, a (C6-C12)alkaryl carboxylic acid, a phenolic compound, a (C1-C10)alkyl alcohol, an ether glycol, or combinations thereof; a hydrophilic component or a surfactant or both; and a hydrophobic component which forms the greatest portion of the composition by weight. An alternative composition for treating and/or preventing an infection on mammalian tissue (particularly, the skin, mucosal tissue, and/or wound) of a subject includes an effective amount of an antimicrobial lipid component, optionally an effective amount of an enhancer component, and a hydrophobic component which forms the greatest portion of the composition by weight.

In one embodiment, the present invention provides a method of treating a burn. The method includes contacting the burned area of a subject with an antimicrobial composition in an amount effective to kill or inactivate one or more microorganisms, wherein the antimicrobial composition includes: an effective amount of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; and an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof. An alternative composition for treating burns includes an effective amount of an antimicrobial lipid component, optionally an effective amount of an enhancer component, and a hydrophobic component which forms the greatest portion of the composition by weight.

In other embodiments, the present invention provides methods for killing or inactivating microorganisms. Herein, to "kill or inactivate" means to render the microorganism ineffective by killing them (e.g., bacteria and fungi) or otherwise rendering them inactive (e.g., viruses). The present invention provides methods for killing bacteria such as *Staphylococcus* spp., *Streptococcus* spp., *Escherichia* spp., *Enterococcus* spp., *Pseudamonas* spp. bacteria and combinations thereof, and more particularly *Staphylococcus aureus* (including antibiotic resistant strains such as methicillin resistant *Staphylococcus aureus*), *Staphylococcus epidermidis*, *Escherichia coli* (*E. coli*), *Pseudomonas aeruginosa* (*Pseudomonas* ae.), *Streptococcus pyogenes*, and combinations thereof which often are on or in the skin or mucosal tissue of a subject. The method includes contacting the microorganism with an antimicrobial composition of the present invention in an amount effective to kill one or more microorganisms (e.g., bacteria and fungi) or inactivate one or more microorganisms (e.g., viruses, particularly herpes virus).

For example, in one embodiment, the present invention provides a method of killing or inactivating microorganisms on mammalian tissue (particularly, the skin, mucosal tissue, and/or in a wound) of a subject. The method includes contacting the affected area with an antimicrobial composition that includes: an effective amount of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; and an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof; and optionally a hydrophilic component, wherein the viscosity of the composition is at least 500 cps. An alternative composition for killing or inactivating microorganisms on mammalian tissue (particularly, the skin, mucosal tissue, and/or in a wound) of a subject includes an effective amount of an antimicrobial lipid component, optionally, an effective amount of an enhancer component, and a hydrophobic component which forms the greatest portion of the composition by weight.

The compositions of the present invention can also be used for providing residual antimicrobial efficacy on a surface that results from leaving a residue or imparting a condition to the surface (e.g., skin, anterior nares, mucosal tissue, wound, or medical device that comes in contact with such tissues (i.e., mammalian tissues), but particularly skin, mucosal tissue, and/or wound) that remains effective and provides significant antimicrobial activity.

For example, in one embodiment, the present invention provides a method of providing residual antimicrobial efficacy on mammalian tissue (particularly, the skin, mucosal tissue, anterior nares, and/or in a wound) of a subject, the method includes contacting the mammalian tissue (typically, skin, mucosal tissue, and/or wound) with an antimicrobial composition that includes: an effective amount of an antimicrobial lipid component that includes a (C7-C12)saturated fatty acid ester of a polyhydric alcohol, a (C8-C22)unsaturated fatty acid ester of a polyhydric alcohol, a (C7-C12)saturated fatty ether of a polyhydric alcohol, a (C8-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters include monoesters and the ethers include monoethers, and for sucrose the esters include monoesters, diesters, or combinations thereof, and the ethers include monoethers, diethers, or combinations thereof; and an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof; and a surfactant and/or a hydrophilic component. An alternative composition for providing residual antimicrobial efficacy includes an effective amount of an antimicrobial lipid component, an effective amount of an enhancer component, and a hydrophobic component which forms the greatest portion of the composition by weight.

In another embodiment, the present invention provides methods of preventing and/or treating a subject for a common cold and/or respiratory affliction caused by a microbial infection. The method includes contacting the subject with a composition of the present invention in at least a portion of the subject's respiratory system (such as but not limited to, at least a portion of the nasal cavities, etc.) in an amount effective to kill or inactivate one or more microorganisms that cause a common cold and/or respiratory affliction. An exemplary antimicrobial composition for use in this method includes an effective amount of an antimicrobial lipid component and an effective amount of an enhancer component.

Methods of manufacture are also provided.

Definitions

The following terms are used herein according to the following definitions.

"Effective amount" means the amount of the antimicrobial lipid component and/or the enhancer component when in a composition, as a whole, provides an antimicrobial (including, for example, antiviral, antibacterial, or antifungal) activity that reduces, prevents, or eliminates one or more species of microbes such that an acceptable level of the microbe results. Typically, this is a level low enough not to cause clinical symptoms, and is desirably a non-detectable level. It should be understood that in the compositions of the present invention, the concentrations or amounts of the components, when considered separately, may not kill to an acceptable level, or may not kill as broad a spectrum of undesired microorganisms, or may not kill as fast; however, when used together such components provide an enhanced (preferably synergistic) antimicrobial activity (as compared to the same components used alone under the same conditions).

It should be understood that (unless otherwise specified) the listed concentrations of all components are for "ready to use" or "as used" compositions. The compositions can be in a concentrated form. That is, certain embodiments of the compositions can be in the form of concentrates that would be diluted by the user with an appropriate vehicle.

"Hydrophilic" refers to a material that will dissolve or disperse in water (or other aqueous solution as specified) at a temperature of 23° C. in an amount of at least 7% by weight, preferably at least 10% by weight, more preferably at least 20% by weight, even more preferably at least 25% by weight, even more preferably at least 30% by weight, and most preferably at least 40% by weight, based on the total weight of the hydrophilic material and the water. The component is considered dissolved if after thoroughly mixing the compound with water at 60° C. for at least 4 hours and allowing this to cool to 23-25° C. for 24 hours, and mixing the composition thoroughly it appears uniform clear solution without visible cloudiness, phase separation, or precipitate in a jar having a path length of 4 cm. Typically, when placed in 1×1 cm cell, the sample exhibits greater than 70% transmission measured in a suitable spectrophotometer at a wavelength of 655 nm. Water dispersible hydrophilic materials disperse in water to form uniform cloudy dispersions after vigorous shaking of a 5% by weight mixture of the hydrophilic component in water. Preferred hydrophilic components are water-soluble.

"Hydrophobic" or "water-insoluble" refers to a material that will not significantly dissolve in water at 23° C. No significant amount means less than 5% by weight, preferably less than 1% by weight, more preferably less than 0.5% by weight, and even more preferably less than 0.1% by weight, based on the total weight of the hydrophobic material and the water. Solubility can be determined by thoroughly mixing the compound with water at the appropriate concentration at 23° C. for at least 24 hours (or at elevated temperature if that is necessary to dissolve the compound), allowing this to sit at 23-25° C. for 24 hours, and observing the sample. In a glass jar with a 4-cm path length the sample should have evidence of a second phase, which can be liquid or solid and may be separated on the top, bottom, or distributed throughout the sample. For crystalline compounds care should be taken to avoid producing a supersaturated solution. The components should be mixed and observed. Cloudiness or presence of a visible precipitate or separate phase indicates that the solubility limit has been exceeded. Typically, when placed in 1×1 cm cell the sample has less than 70% transmission measured in a suitable spectrophotometer at a wavelength of 655 nm. For solubility determinations less than that which can be observed with the naked eye the solubility is determined using radiolabeled compounds as described under "Conventional Solubility Estimations in Solubility of Long-Chain Fatty Acids in Phosphate Buffer at pH 7.4," Henrik Vorum, et al. in *Biochimica et. Biophysica Acta*, 1126, 135-142 (1992).

"Stable" means physically stable or chemically stable, which are both defined in greater detail below.

"Enhancer" means a component that enhances the effectiveness of the antimicrobial lipid component such that when the composition less the antimicrobial lipid component and the composition less the enhancer component are used separately, they do not provide the same level of antimicrobial activity as the composition as a whole. For example, an enhancer component in the absence of the antimicrobial lipid component may not provide any appreciable antimicrobial activity. The enhancing effect can be with respect to the level of kill, the speed of kill, and/or the spectrum of microorganisms killed, and may not be seen for all microorganisms. In fact, an enhanced level of kill is most often seen in Gram negative bacteria such as *Escherichia coli*. An enhancer may be a synergist such that when combined with the remainder of the composition, the composition as a whole displays an activity that is greater than the sum of the activity of the composition less the enhancer component and the composition less the antimicrobial lipid component.

"Microorganism" or "microbe" or "microorganism" refers to bacteria, yeast, mold, fungi, protozoa, mycoplasma, as well as viruses (including lipid enveloped RNA and DNA viruses).

"Antibiotic" means an organic chemical produced by microorganisms that has the ability in dilute concentrations to destroy or inhibit microorganisms and is used to treat infectious disease. This may also encompass semi-synthetic compounds that are chemical derivatives of the compound produced by microorganisms or synthetic compounds that act on very specific biochemical pathways necessary for the cell's survival.

"Antiseptic" means a chemical agent that kills pathogenic and non-pathogenic microorganisms. Preferred antiseptics exhibit at least a 4 log reduction of both *P. aeruginosa* and *S. aureus* in 60 minutes from an initial inoculum of 1-3×10$^7$ cfu/ml when tested in Mueller Hinton broth at 35° C. at a concentration of 0.25 wt-% in a Rate of Kill assay using an appropriate neutralizer as described in "The Antimicrobial Activity in vitro of chlorhexidine, a mixture of isothiazolinones (Kathon CG) and cetyl trimethyl ammonium bromide (CTAB)," G. Nicoletti et al., *Journal of Hospital Infection*, 23, 87-111 (1993). Antiseptics generally interfere more broadly with the cellular metabolism and/or the cell envelope.

"Mucous membranes," "mucosal membranes," and "mucosal tissue" are used interchangeably and refer to the surfaces of the nasal (including anterior nares, nasoparangyl cavity, etc.), oral (e.g., mouth), outer ear, middle ear, vaginal cavities, and other similar tissues. Examples include mucosal membranes such as buccal, gingival, nasal, ocular, tracheal, bronchial, gastrointestinal, rectal, urethral, ureteral, vaginal, cervical, and uterine mucosal membranes.

"Antimicrobial lipid" means an antiseptic that preferably has a solubility in water of no greater than 1.0 gram per 100 grams (1.0 g/100 g) deionized water. Preferred antimicrobial lipids have a solubility in water of no greater than 0.5 g/100 g deionized water, more preferably, no greater than 0.25 g/100 g deionized water, and even more preferably, no greater than 0.10 g/100 g deionized water. Solubilities are determined using radiolabeled compounds as described under "Conventional Solubility Estimations" in Solubility of Long-Chain Fatty Acids in Phosphate Buffer at pH 7.4, Henrik Vorum et al., in *Biochimica et. Biophysica Acta.*, 1126, 135-142 (1992). Preferred antimicrobial lipids have a solubility in deionized water of at least 100 micrograms (μg) per 100 grams deionized water, more preferably, at least 500 μg/100 g deionized water, and even more preferably, at least 1000 μg/100 g deionized water. The antimicrobial lipids preferably have a hydrophile/lipophile balance (HLB) of at most 6.2, more preferably at most 5.8, and even more preferably at most 5.5. The antimicrobial lipids preferably have an HLB of at least 3, preferably at least 3.2, and even more preferably at least 3.4.

"Fatty" as used herein refers to a straight or branched chain alkyl or alkylene moiety having 6 to 14 (odd or even number) carbon atoms, unless otherwise specified.

"Affliction" means a condition to a body resulting from sickness, disease, injury, bacterial colonization, etc.

"Treat" or "treatment" means to improve the condition of a subject relative to the affliction, typically in terms of clinical symptoms of the condition.

"Decolonization" refers to a reduction in the number of microorganisms (e.g., bacteria and fungi) present in or on tissue that do not necessarily cause immediate clinical symptoms. Examples of decolonization include, but are not limited to, decolonization of the nasal cavity and wounds. Ordinarily fewer microorganisms are present in colonized tissue than in infected tissue. When the tissue is completely deconolonized the microorganisms have been "eradicated."

"Subject" and "patient" includes humans, sheep, horses, cattle, pigs, dogs, cats, rats, mice, or other mammal "Wound" refers to an injury to a subject which involves a break in the normal skin barrier exposing tissue below, which is caused by, for example, lacerations, surgery, burns, damage to underlying tissue such as pressure sores, poor circulation, and the like. Wounds are understood to include both acute and chronic wounds.

The terms "comprises" and variations thereof do not have a limiting meaning where these terms appear in the description and claims.

As used herein, "a," "an," "the," "at least one," and "one or more" are used interchangeably. The term "and/or" means one or all of the listed elements (e.g., preventing and/or treating an affliction means preventing, treating, or both treating and preventing further afflications).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention provides antimicrobial (including, e.g., antiviral, antibacterial, and antifungal) compositions. These compositions include one or more antimicrobial lipids, such as, for example, a fatty acid ester of a polyhydric alcohol, a fatty ether of a polyhydric alcohol, or alkoxylated derivatives thereof (of either the ester or ether). In certain embodiments the compositions also include one or more enhancers. Certain compositions also include one or more surfactants, one or more hydrophilic compounds, and/or one or more hydrophobic compounds. In certain embodiments, the hydrophobic component can be the same as the antimicrobial lipid component.

Such compositions adhere well to bodily tissues (i.e., mammalian tissues such as skin, mucosal tissue, and wounds) and thus are very effective topically. Thus, the present invention provides a wide variety of uses of the compositions. Particularly preferred methods involve topical application, particularly to mucosal tissues (i.e., mucous membranes including the anterior nares and other tissues of the upper respiratory tract), as well as skin (e.g., skin lesions) and wounds. Herein, such tissues are preferred examples of mammalian tissues.

For certain applications in which limited antimicrobial activity is desired, compositions containing an antimicrobial lipid component can be used, whereas in other applications in which more broad antimicrobial activity is desired, compositions containing both an antimicrobial lipid component and an enhancer component are used. For example, in certain situations it may be desirable to kill or inactivate only one type or class of microorganism (e.g., Gram positive) as opposed to all the microorganisms present. In such situations, compositions of the present invention that contain an antimicrobial lipid component without an enhancer component may be suitable.

Compositions of the present invention can be used to provide effective topical antimicrobial activity. For example, they can be used for hand disinfection, particularly in presurgical scrubs. They can be used to disinfect various body parts, particularly in patient presurgical skin antiseptics.

Compositions of the present invention can be used to provide effective topical antimicrobial activity and thereby treat and/or prevent a wide variety of afflications. For example, they can be used in the treatment and/or prevention of afflictions that are caused, or aggravated by, microorganisms (e.g., Gram positive bacteria, Gram negative bacteria, fungi, protozoa, mycoplasma, yeast, viruses, and even lipid-enveloped viruses) on skin and/or mucous membranes, such as those in the nose (anterial nares, nasopharangyl cavity, nasal cavities, etc.), outer ear, and middle ear, mouth, rectum, vagina, or other similar tissues. Particularly relevant organisms that cause or aggravate such afflications include *Staphylococcus* spp., *Streptococcus* spp., *Pseudomonas* spp., *Enterococcus* spp., and *Esherichia* spp., bacteria, as well as herpes virus, *Aspergillus* spp., *Fusarium* spp. *Candida* spp. as well as combinations thereof. Particularly virulent organisms include *Staphylococcus aureus* (including resistant strains such as Methicillin Resistant *Staphylococcus Aureus* (MRSA), *Staphylococcus epidermidis, Streptococcus pneumoniae, Enterococcus faecalis*, Vancomycin Resistant *Enterococcus* (VRE), *Pseudomonas auerginosa*,

*Escherichia coli, Aspergillus niger, Aspergillus fumigatus, Aspergillus clavatus, Fusarium solani, Fusarium oxysporum, Fusarium chlamydosporum, Candida albicans, Candida glabrata, Candida krusei*, and combinations thereof.

Compositions of the present invention can be used for the prevention and/or treatment of one or more microorganism-caused infections or other afflictions. In particular, compositions of the present invention can be used for preventing and/or treating one or more of the following: skin lesions, conditions of the skin such as impetigo, eczema, diaper rash in infants as well as incontinent adults, inflammation around ostomy devices, shingles, and bacterial infections in open wounds (e.g., cuts, scrapes, burns, lacerations, chronic wounds); necrotizing faciitis; infections of the outer ear; acute or chronic otitis media (middle ear infection) caused by bacterial, viral, or fungal contamination; fungal and bacterial infections of the vagina or rectum; vaginal yeast infections; bacterial rhinitis; ocular infections; cold sores; genital herpes; colonization by *Staphylococcus aureus* in the anterior nares (e.g. prior to surgery or hemodialysis); mucositis (i.e., inflammation as opposed to infection of a mucous membrane typically induced by non-invasive fungus); chronic sinusitis (e.g., that caused by bacterial or viral contamination); non-invasive fungus-induced rhinosinusitis; chronic colitis; Crohn's disease; burns; napkin rash; tinea pedis (i.e., athlete's foot); tinea curis (i.e., jock itch); tinea corporis (i.e., ringworm); candidiasis; strep throat, strep pharyngitis, and other Group A *Streptococci* infections; rosacea (often called adult acne); psoriasis; common cold; and respiratory afflictions (e.g., asthma). In sum, compositions of the present invention can be used for preventing and/or treating a wide variety of topical afflictions caused by microbial infection (e.g., yeast, viral, bacterial infections).

Compositions of the present invention can be used on a wide variety of surfaces. For example, they can be used on mammalian tissues (particularly, skin, mucosal tissue, chronic wounds, acute wounds, burns, and the like) and hard surfaces such as medical (e.g., surgical) devices, floor tiles, countertops, tubs, dishes, as well as on gloves (e.g., surgical gloves). They can also be delivered from swabs, cloth, sponges, foams, nonwovens, and paper products (e.g., paper towels and wipes), for example. Typically, compositions with hydrophobic components are used on mammalian tissues (particularly, skin, mucosal tissue, wounds) and medical devices that come in contact with such surfaces, whereas compositions with hydrophilic components are used on these surfaces as well as other hard surfaces (e.g., floor tiles).

Thus, the present invention also provides various methods of use of compositions of the present invention. Various embodiments of the present invention include: a method of preventing an affliction caused, or aggravated by, a microorganism on mammalian tissue (particularly, skin and/or a mucous membrane); a method of decolonizing at least a portion of the nasal cavities, anterior nares, and/or nasopharynx of a subject of microorganisms; a method of treating a middle ear infection in a subject (through the middle ear, the Eustachian tube, and/or the tympanic membrane); a method of treating chronic sinusitis in a subject (by treating at least a portion of the respiratory system, particularly the upper respiratory system, including the nasal cavities, anterior nares, and/or nasopharynx); a method of treating impetigo on the skin of a subject; a method of treating and/or preventing an infection on mammalian tissue (particularly, the skin, mucosal tissue, and/or wound) of a subject; a method of treating a burn; a method of killing or inactivating microorganisms (e.g., killing bacteria and/or fungi, or inactivating viruses); a method for providing residual antimicrobial efficacy (e.g., antibacterial, antifungal, and/or antiviral efficacy) that results from leaving a residue or imparting a condition on a surface (such as skin, mucosal tissue, wound, and/or medical device that contacts such surfaces) that remains effective and provides significant antimicrobial activity; a method of preventing and/or treating a subject for a common cold and/or respiratory affliction caused by a microbial infection; a method of decolonizing at least a portion of the throat/esophagus of a subject of microorganisms; and a method of decolonizing at least a portion of the oral cavity of a subject of microorganisms.

It should be understood that compositions of the present invention can be used in situations in which there are no clinical indications of an affliction. For example, compositions of the present invention can be used in methods of decolonizing at least a portion of the nasal cavities (i.e., space behind the vestibule of the nose), anterior nares (i.e., the opening in the nose to the nasal cavities, also referred to as the external nares), and/or nasopharynx (i.e., the portion of the pharynx, i.e., throat, that lies above the point of food entry into the pharynx) of a subject of microorganisms. A suitable model to test for the effectiveness of compositions to decolonize the anterior nares has been established and is described by K. Kiser et al., *Infect and Immunity*, 67(10), 5001-5006 (1999). Compositions of the present invention can also be used to decolonize microorganisms from wounds.

Decolonization methods using compositions of the present invention are particularly useful in immunocompromised patients (including oncology patients, diabetics, HIV patients, transplant patients an the like), particularly for fungi such as *Aspergillus* spp. and *Fusarium* spp.

In particular, compositions of the present invention can be used in chronic wounds to eliminate methicillin-resistant *Staphylococcus aureus*, which may or may not show clinical signs of infection such as inflammation, pus, exudate, etc. Also, it is of significance to note that certain compositions of the present invention can kill lipid-enveloped viruses, which can be very difficult to kill and can cause shingles (Herpes), chronic sinusitis, otitis media, and other local diseases.

Those of ordinary skill in the art will readily determine when a composition of the present invention provides antimicrobial activity using assay and bacterial screening methods well known in the art. One readily performed assay involves exposing selected known or readily available viable microorganism strains, such as *Enterococcus* spp., *Aspergillus* spp., *Escherichia* spp., *Staphylococcus* spp., *Streptococcus* spp., *Pseudomonas* spp., or *Salmonella* spp., to a test composition at a predetermined bacterial burden level in a culture media at an appropriate temperature. For the preferred compositions of the present invention this is most conveniently done by the Antimicrobial Kill Rate Test described in the Examples Section. Briefly, after a sufficient contact time, an aliquot of a sample containing the exposed bacteria is collected, diluted, and plated out on agar. The plated sample of bacteria is incubated for forty-eight hours and the number of viable bacterial colonies growing on the plate is counted. Once colonies have been counted the reduction in the number of bacteria caused by the test composition is readily determined Bacterial reduction is generally reported as $\log_{10}$ reduction determined by the difference between the $\log_{10}$ of the initial inoculum count and the $\log_{10}$ of the inoculum count after exposure. Preferred compositions of the present invention have an average of at least a 4 log reduction in test bacteria in 10 minutes.

Many of the preferred compositions were tested as described in the Examples Section for antimicrobial activity against MRSA (Gram positive, ATCC Number 16266), *E. coli* (Gram negative, ATCC Number 11229), and *Pseudomonas aeruginosa* (Gram negative, ATCC Number 15442). In general, the *Pseudomonas aeruginosa* is often the most difficult to kill. Preferred compositions of the present invention also exhibit very rapid antimicrobial activity. As shown in the Examples Section, preferred formulations are able to achieve an average log reduction of at least 4 log against these three organisms after a 10 minute exposure and preferably after a 5 minute exposure. More preferred compositions are able to achieve an average log reduction of at least 5 log and even more preferred at least 6 log against these three organisms after a 10 minute exposure and preferably after a 5 minute exposure.

For residual antimicrobial efficacy, compositions of the present invention preferably maintain an average log reduction of at least 1 log, more preferably at least 1.5 log, and even more preferably at least 2 log, for at least 0.5 hour, more preferably at least 1 hour, and even more preferably at least 3 hours after application to an affected site or after testing the composition on the forearm of a subject. To test this, a composition was applied to the forearm of a subject as a uniform wet coating in an amount of approximately 4 milligrams per square centimeter (mg/cm$^2$) to the forearm of a healthy subject and allowed to thoroughly dry (typically a minimum of 10 minutes) over an area of approximately 5×5 cm. The dried composition was gently washed with 23° C. normal saline (0.9% by weight sodium chloride). The saline washed site was exposed to a known quantity of bacteria in an innoculum of 10$^6$ bacteria/ml (typically *Staphylococcus epidermidis* or *E. coli*) for 30 minutes. The bacteria were recovered and treated with an effective neutralizer and incubated to quantify the bacteria remaining. Particularly preferred compositions retain at least 1 log reduction and preferably at least 2 log reduction of bacteria after a gentle rinse with 500 ml saline poured over the site by placing the saline containiner as close to the site as possible so as to not have the saline fall onto the site.

Significantly, certain embodiments of the present invention have a very low potential for generating microbial resistance. For example, preferred compositions of the present invention have an increase in the ratio of final to initial MIC levels (i.e., minimum inhibitory concentration) of less than 16, more preferably less than 8, and even more preferably less than 4. Such an emergence of resistance assay should be carried out such that the microorganisms are subjected initially to sub MIC levels (e.g., ½ the MIC) of antimicrobial lipid and after 24 hours the microorganisms passed into broth containing twice the concentration of antimicrobial lipid. This is repeated for 8 days and each day microorganisms are removed to determine the new MIC. Thus, such compositions can be applied multiple times over one or more days to treat topical infections or to eradicate unwanted bacteria (such as nasal colonization of *Staphylococcus aureus*).

Preferred compositions of the present invention contain an effective amount of antimicrobial lipid component to rapidly kill or inactivate microorganisms on skin, skin lesions, and mucosal membranes. In certain embodiments, essentially all the microorganisms are eradicated or inactivated within five days, preferably within three days, more preferably two days, and most preferably within 24 hours using one or more doses.

Preferred compositions of the present invention have a generally low irritation level for skin, skin lesions, and mucosal membranes (including the anterior nares, nasal cavities, nasopharangyl cavity and other portions of the upper respiratory tract). For example, certain preferred compositions of the present invention are no more irritating than BACTROBAN ointment (on skin) or BACTROBAN NASAL (in the anterior nares) products available from Glaxo Smith Kline.

Preferred compositions of the present invention are substantive for relatively long periods of time to ensure adequate efficacy. For example, certain compositions of the present invention remain at the site of application with antimicrobial activity for at least 4 hours and more preferably at least 8 hours.

Preferred compositions of the present invention are physically stable. As defined herein "physically stable" compositions are those that do not significantly change due to substantial precipitation, crystallization, phase separation, and the like, from their original condition during storage at 23° C. for at least 3 months, and preferably for at least 6 months. Particularly preferred compositions are physically stable if a 10-milliliter (10-ml) sample of the composition when placed in a 15-ml conical-shaped graduated plastic centrifuge tube (Corning) and centrifuged at 3,000 revolutions per minute (rpm) for 10 minutes using a Labofuge B, model 2650 manufactured by Heraeus Sepatech GmbH, Osterode, West Germany (or similar centrifuge at 2275×g) has no visible phase separation in the bottom or top of the tube.

Preferred compositions of the present invention exhibit good chemical stability. This can be especially a concern with the antimicrobial fatty acid esters, which can often undergo transesterification, for example. Preferred compositions retain at least 85%, more preferably at least 90%, even more preferably at least 92%, and even more preferably at least 95%, of the antimicrobial lipid component after aging for 4 weeks at 40° C. (an average of three samples) beyond the initial 5-day equilibration period at 23° C. The most preferred compositions retain an average of at least 97% of the antimicrobial lipid component after aging for 4 weeks at 40° C. in a sealed container beyond the initial 5-day equilibration period at 23° C. The percent retention is understood to mean the weight percent of antimicrobial lipid component retained. This is determined by comparing the amount remaining in a sample aged (i.e., aged beyond the initial 5-day equilibration period) in a sealed container that does not cause degradation, to the actual measured level in an identically prepared sample (preferably from the same batch) and allowed to sit at 23° C. for five days. The level of antimicrobial lipid component is preferably determined using gas chromatography as described in the Aging Study Using Gas Chromatography test method included in the Examples Section.

Generally, the compositions of this invention may be in one of the following forms:

A hydrophobic ointment: The compositions are formulated with a hydrophobic base (e.g., petrolatum, thickened or gelled water insoluble oils, and the like) and optionally having a minor amount of a water soluble phase.

An oil-in-water emulsion: The compositions may be formulations in which the antimicrobial lipid component is emulsified into an emulsion comprising a discrete phase of a hydrophobic component and a continuous aqueous phase that includes water and optionally one or more polar hydrophilic carrier(s) as well as salts, surfactants, emulsifiers, and other components. These emulsions may include water-soluble or water-swellable polymers as well as one or more emulsifier(s) that help to stabilize the emulsion. These emulsions generally have higher conductivity values, as described in U.S. patent application Ser. No. 09/966,511, filed on Sep. 28, 2001.

A water-in-oil emulsion: The compositions may be formulations in which the antimicrobial lipid component is incorporated into an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) that help to stabilize the emulsion.

Thickened Aqueous gels: These systems include an aqueous phase which has been thickened to achieve a viscosity of at least 500 centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity is determined using the Viscosity Test described herein. These systems can be thickened by suitable natural, modified natural, or synthetic polymers as described below. Alternatively, the thickened aqueous gels can be thickened using suitable polyethoxylated alkyl chain surfactants that effectively thicken the composition as well as other nonionic, cationic, or anionic emulsifier systems. Preferably, cationic or anionic emulsifier systems are chosen since some polyethoxylated emulsifiers can inactivate the antimicrobial lipids especially at higher concentrations. For certain embodiments, anionic emulsifier systems are used. Examples include the nonioinic systems such as Polawax, Cosmowax, and Crothix systems as well as cationic (Behenyl TMS) and anionic (Crodaphos CES) systems from Croda Inc.

Hydrophilic gels: These are systems in which the continuous phase includes at least one water soluble hydrophilic component other than water. The formulations may optionally also contain water up to 20% by weight. Higher levels may be suitable in some compositions. Suitable hydrophilic components include one or more glycols such as glycerin, propylene glycol, butylene glycols, etc., polyethylene glycols (PEG), random or block copolymers of ethylene oxide, propylene oxide, and/or butylene oxide, polyalkoxylated surfactants having one or more hydrophobic moieties per molecule, silicone copolyols, as well as combinations thereof, and the like. One skilled in the art will recognize that the level of ethoxylation should be sufficient to render the hydrophilic component water soluble or water dispersible at 23° C. In most embodiments, the water content is less than 20%, preferably less than 10%, and more preferably less than 5% by weight of the composition.

Antimicrobial Lipid Component

The antimicrobial lipid component is that component of the composition that provides at least part of the antimicrobial activity. That is, the antimicrobial lipid component has at least some antimicrobial activity for at least one microorganism. It is generally considered the main active component of the compositions of the present invention.

In certain embodiments, the antimicrobial lipid preferably has a solubility in water of no greater than 1.0 gram per 100 grams (1.0 g/100 g) deionized water. More preferred antimicrobial lipids have a solubility in water of no greater than 0.5 g/100 g deionized water, even more preferably, no greater than 0.25 g/100 g deionized water, and even more preferably, no greater than 0.10 g/100 g deionized water. Preferred antimicrobial lipids have a solubility in deionized water of at least 100 micrograms (µg) per 100 grams deionized water, more preferably, at least 500 µg/100 g deionized water, and even more preferably, at least 1000 µg/100 g deionized water.

The antimicrobial lipids preferably have a hydrophile/lipophile balance (HLB) of at most 6.2, more preferably at most 5.8, and even more preferably at most 5.5. The antimicrobial lipids preferably have an HLB of at least 3, preferably at least 3.2, and even more preferably at least 3.4.

Preferred antimicrobial lipids are uncharged and have an alkyl or ankenyl hydrocarbon chain containing at least 7 carbon atoms.

In certain embodiments, the antimicrobial lipid component preferably includes one or more fatty acid esters of a polyhydric alcohol, fatty ethers of a polyhydric alcohol, or alkoxylated derivatives thereof (of either or both of the ester and ether), or combinations thereof. More specifically and preferably, the antimicrobial component is selected from the group consisting of a (C7-C12)saturated fatty acid ester of a polyhydric alcohol (preferably, a (C8-C12)saturated fatty acid ester of a polyhydric alcohol), a (C8-C22)unsaturated fatty acid ester of a polyhydric alcohol (preferably, a (C12-C22)unsaturated fatty acid ester of a polyhydric alcohol), a (C7-C12)saturated fatty ether of a polyhydric alcohol (preferably, a (C8-C12)saturated fatty ether of a polyhydric alcohol), a (C8-C22)unsaturated fatty ether of a polyhydric alcohol (preferably, a (C12-C22)unsaturated fatty ether of a polyhydric alcohol), an alkoxylated derivative thereof, and combinations thereof. Preferably, the esters and ethers are monoesters and monoethers, unless they are esters and ethers of sucrose in which case they can be monoesters, diesters, monoethers, or monoethers. Various combinations of monoesters, diesters, monoethers, and diethers can be used in a composition of the present invention.

A fatty acid ester of a polyhydric alcohol is preferably of the formula $(R^1—C(O)—O)_n—R^2$, wherein $R^1$ is the residue of a (C7-C12)saturated fatty acid (preferably, a (C8-C12) saturated fatty acid), or a (C8-C22)unsaturated (preferably, a C12-C22)unsaturated, including polyunsaturated) fatty acid, $R^2$ is the residue of a polyhydric alcohol (typically and preferably, glycerin, propylene glycol, and sucrose, although a wide variety of others can be used including pentaerythritol, sorbitol, mannitol, xylitol, etc.), and n=1 or 2. The $R^2$ group includes at least one free hydroxyl group (preferably, residues of glycerin, propylene glycol, or sucrose). Preferred fatty acid esters of polyhydric alcohols are esters derived from C7, C8, C9, C10, C11, and C12 saturated fatty acids. For embodiments in which the polyhydric alcohol is glycerin or propylene glycol, n=1, although when it is sucrose, n=1 or 2.

Exemplary fatty acid monoesters include, but are not limited to, glycerol monoesters of lauric (monolaurin), caprylic (monocaprylin), and capric (monocaprin) acid, and propylene glycol monoesters of lauric, caprylic, and capric acid, as well as lauric, caprylic, and capric acid monoesters of sucrose. Other fatty acid monoesters include glycerin and propylene glycol monoesters of oleic (18:1), linoleic (18:2), linolenic (18:3), and arachonic (20:4) unsaturated (including polyunsaturated) fatty acids. As is generally know, 18:1, for example, means the compound has 18 carbon atoms and 1 carbon-carbon double bond. Preferred unsaturated chains have at least one unsaturated group in the cis isomer form. In certain preferred embodiments, the fatty acid monoesters that are suitable for use in the present composition include known monoesters of lauric, caprylic, and capric acid, such as that known as GML or the trade designation LAURICIDIN (the glycerol monoester of lauric acid commonly referred to as monolaurin or glycerol monolaurate), glycerol monocaprate, glycerol monocaprylate, propylene glycol monolaurate, propylene glycol monocaprate, propylene glycol monocaprylate, and combinations thereof.

Exemplary fatty acid diesters of sucrose include, but are not limited to, lauric, caprylic, and capric diesters of sucrose as well as combinations thereof.

A fatty ether of a polyhydric alcohol is preferably of the formula $(R^3—O)_n—R^4$, wherein $R^3$ is a (C7-C12)saturated aliphatic group (preferably, a (C8-C12)saturated aliphatic group), or a (C8-C22)unsaturated (preferably, (C12-C22) unsaturated, including polyunsaturated) aliphatic group, $R^4$ is the residue of glycerin, sucrose, or propylene glycol, and n=1 or 2. For glycerin and propylene glycol n=1, and for sucrose n=1 or 2. Preferred fatty ethers are monoethers of (C7-C12)alkyl groups (more preferably, (C8-C12)alkyl groups).

Exemplary fatty monoethers include, but are not limited to, laurylglyceryl ether, caprylglycerylether, caprylylglyceryl ether, laurylpropylene glycol ether, caprylpropyleneglycol ether, and caprylylpropyleneglycol ether. Other fatty monoethers include glycerin and propylene glycol monoethers of oleyl (18:1), linoleyl (18:2), linolenyl (18:3), and arachonyl (20:4) unsaturated and polyunsaturated fatty alcohols. In certain preferred embodiments, the fatty monoethers that are suitable for use in the present composition include laurylglyceryl ether, caprylglycerylether, caprylyl glyceryl ether, laurylpropylene glycol ether, caprylpropyleneglycol ether, caprylylpropyleneglycol ether, and combinations thereof. Unsaturated chains preferably have at least one unsaturated bond in the cis isomer form.

The alkoxylated derivatives of the aforementioned fatty acid esters and fatty ethers (e.g., one which is ethoxylated and/or propoxylated on the remaining alcohol group(s)) also have antimicrobial activity as long as the total alkoxylate is kept relatively low. Preferred alkoxylation levels are disclosed in U.S. Pat. No. 5,208,257 (Kabara). In the case where the esters and ethers are ethoxylated, the total moles of ethylene oxide is preferably less than 5, and more preferably less than 2.

The fatty acid esters or fatty ethers of polyhydric alcohols can be alkoxylated, preferably ethoxylated and/or propoxylated, by conventional techniques. Alkoxylating compounds are preferably selected from the group consisting of ethylene oxide, propylene oxide, and mixtures thereof, and similar oxirane compounds.

The compositions of the present invention include one or more fatty acid esters, fatty ethers, alkoxylated fatty acid esters, or alkoxylated fatty ethers at a suitable level to produce the desired result. Such compositions preferably include a total amount of such material of at least 0.01 percent by weight (wt-%), more preferably at least 0.1 wt-%, even more preferably at least 0.25 wt-%, even more preferably at least 0.5 wt-%, and even more preferably at least 1 wt-%, based on the total weight of the "ready to use" or "as used" composition. In a preferred embodiment, they are present in a total amount of no greater than 20 wt-%, more preferably no greater than 15 wt-%, even more preferably no greater than 10 wt-%, and even more preferably no greater than 5 wt-%, based on the "ready to use" or "as used" composition. Certain compositions may be higher in concentration if they are intended to be diluted prior to use.

Preferred compositions of the present invention that include one or more fatty acid monoesters, fatty monoethers, or alkoxylated derivatives thereof can also include a small amount of a di- or tri-fatty acid ester (i.e., a fatty acid di- or tri-ester), a di- or tri-fatty ether (i.e., a fatty di- or tri-ether), or alkoxylated derivative thereof. Preferably, such components are present in an amount of no more than 50 wt-%, more preferably no more than 40 wt-%, even more preferably no more than 25 wt-%, even more preferably no more than 15 wt-%, even more preferably no more than 10 wt-%, even more preferably no more than 7 wt-%, even more preferably no more than 6 wt-%, and even more preferably no more than 5 wt-%, based on the total weight of the antimicrobial lipid component. For example, for monoesters, monoethers, or alkoxylated derivatives of glycerin, preferably there is no more than 15 wt-%, more preferably no more than 10 wt-%, even more preferably no more than 7 wt-%, even more preferably no more than 6 wt-%, and even more preferably no more than 5 wt-% of a diester, diether, triester, triether, or alkoxylated derivatives thereof present, based on the total weight of the antimicrobial lipid components present in the composition. However, as will be explained in greater detail below, higher concentrations of di- and tri-esters may be tolerated in the raw material if the formulation initially includes free glycerin because of transesterification reactions.

Although in some situations it is desirable to avoid di- or tri-esters as a component of the starting materials, it is possible to use relatively pure tri-esters in the preparation of certain compositions of the present invention (for example, as a hydrophobic component) and have effective antimicrobial activity.

To achieve rapid antimicrobial activity, formulations may incorporate one or more antimicrobial lipids in the composition approaching, or preferably exceeding, the solubility limit in the hydrophobic phase. While not intended to be bound by theory, it appears that antimicrobial lipids that preferably partition into the hydrophobic component are not readily available to kill microorganisms which are in or associated with an aqueous phase in or on the tissue. In most compositions, the antimicrobial lipid is preferably incorporated in at least 60%, preferably, at least 75%, more preferably, at least 100%, and most preferably, at least 120%, of the solubility limit of the hydrophobic component at 23° C. This in conveniently determined by making the formulation without the antimicrobial lipid, separating the phases (e.g., by centrifugation or other suitable separation technique) and determining the solubility limit by addition of progressively greater levels of the antimicrobial lipid until precipitation occurs. One skilled in the art will realize that creation of supersaturated solutions must be avoided for an accurate determination.

Enhancer Component

Compositions of the present invention include an enhancer (preferably a synergist) to enhance the antimicrobial activity especially against Gram negative bacteria, such as *E. coli* and *Psuedomonas* sp. The chosen enhancer preferably affects the cell envelope of the bacteria. While not bound by theory, it is presently believed that the enhancer functions by allowing the antimicrobial lipid to more easily enter the cell cytoplasm and/or by facilitating disruption of the cell envelope. The enhancer component may include an alpha-hydroxy acid, a beta-hydroxy acid, other carboxylic acids, a (C1-C4)alkyl carboxylic acid, a (C6-C12)aryl carboxylic acid, a (C6-C12)aralkyl carboxylic acid, a (C6-C12) alkaryl carboxylic acid, a phenolic compound (such as certain antioxidants and parabens), a (C1-C10)monohydroxy alcohol, a chelating agent, or a glycol ether (i.e., ether glycol). Various combinations of enhancers can be used if desired.

The alpha-hydroxy acid, beta-hydroxy acid, and other carboxylic acid enhancers are preferably present in their protonated, free acid form. It is not necessary for all of the acidic enhancers to be present in the free acid form; however, the preferred concentrations listed below refer to the amount present in the free acid form. Additional, non-alpha hydroxy acid, betahydroxy acid or other carboxylic acid enhancers, may be added in order to acidify the formulation or buffer it at a pH to maintain antimicrobial activity. Furthermore, the chelator enhancers that include carboxylic acid groups are preferably present with at least one, and more preferably at least two, carboxylic acid groups in their free acid form. The concentrations given below assume this to be the case.

One or more enhancers may be used in the compositions of the present invention at a suitable level to produce the desired result. In a preferred embodiment, they are present in a total amount greater than 0.01 wt-%, more preferably in an amount greater than 0.1 wt-%, even more preferably in an amount greater than 0.2 wt-%, even more preferably in an amount greater than 0.25 wt-%, and most preferably in an amount greater than 0.4 wt-% based on the total weight of the ready to use composition. In a preferred embodiment, they are present in a total amount of no greater than 20 wt-%, based on the total weight of the ready to use composition. Such concentrations typically apply to alpha-hydroxy acids, beta-hydroxy acids, other carboxylic acids, chelating agents, phenolics, ether glycols, (C5-C10)monohydroxy alcohols. Generally, higher concentrations are needed for (C1-C4) monohydroxy alcohols, as described in greater detail below.

The alpha-hydroxy acid, beta-hydroxy acid, and other carboxylic acid enhancers, as well as chelators that include carboxylic acid groups, are preferably present in a concentration of no greater than 100 milliMoles per 100 grams of formulated composition. In most embodiments, alpha-hydroxy acid, beta-hydroxy acid, and other carboxylic acid enhancers, as well as chelators that include carboxylic acid groups, are preferably present in a concentration of no greater than 75 milliMoles per 100 grams, more preferably no greater than 50 milliMoles per 100 grams, and most preferably no greater than 25 milliMoles per 100 grams of formulated composition.

The total concentration of the enhancer component relative to the total concentration of the antimicrobial lipid component is preferably within a range of 10:1 to 1:300, and more preferably 5:1 and 1:10, on a weight basis.

An additional consideration when using an enhancer is the solubility and physical stability in the compositions. Many of the enhancers discussed herein are insoluble in preferred hydrophobic components such as petrolatum. It has been found that the addition of a minor amount (typically less than 30 wt-%, preferably less than 20 wt-%, and more preferably less than 12 wt-%) of a hydrophilic component not only helps dissolve and physically stabilize the composition but improves the antimicrobial activity as well. These hydrophilic components are described below.

Alternatively, the enhancer may be present in excess of the solubility limit provided that the composition is physically stable. This may be achieved by utilizing a sufficiently viscous composition that stratification (e.g., settling or creaming) of the antimicrobial lipid does not appreciably occur.

Alpha-hydroxy Acids. An alpha-hydroxy acid is typically a compound represented by the formula:

$R^5(CR^6OH)_n COOH$ wherein: $R^5$ and $R^6$ are each independently H or a (C1-C8) alkyl group (straight, branched, or cyclic), a (C6-C12)aryl, or a (C6-C12)aralkyl or alkaryl group (wherein the alkyl group is straight, branched, or cyclic), wherein $R^5$ and $R^6$ may be optionally substituted with one or more carboxylic acid groups; and n=1-3, preferably, n=1-2.

Exemplary alpha-hydroxy acids include, but are not limited to, lactic acid, malic acid, citric acid, 2-hydroxybutanoic acid, 3-hydroxybutanoic acid, mandelic acid, gluconic acid, glycolic acid, tartaric acid, alpha-hydroxyethanoic acid, ascorbic acid, alpha-hydroxyoctanoic acid, hydroxycaprylic acid, and salicylic acid, as well as derivatives thereof (e.g., compounds substituted with hydroxyls, phenyl groups, hydroxyphenyl groups, alkyl groups, halogens, as well as combinations thereof). Preferred alpha-hydroxy acids include lactic acid, malic acid, and mandelic acid. These acids may be in D, L, or DL form and may be present as free acid, lactone, or partial salts thereof. All such forms are encompassed by the term "acid." Preferably, the acids are present in the free acid form. In certain preferred embodiments, the alpha-hydroxy acids useful in the compositions of the present invention are selected from the group consisting of lactic acid, mandelic acid, and malic acid, and mixtures thereof. Other suitable alpha-hydroxy acids are described in U.S. Pat. No. 5,665,776 (Yu).

One or more alpha-hydroxy acids may be used in the compositions of the present invention at a suitable level to produce the desired result. In a preferred embodiment, they are present in a total amount of at least 0.25 wt-%, more preferably, at least 0.5 wt-%, and even more preferably, at least 1 wt-%, based on the total weight of the ready to use composition. In a preferred embodiment, they are present in a total amount of no greater than 10 wt-%, more preferably, no greater than 5 wt-%, and even more preferably, no greater than 3 wt-%, based on the total weight of the ready to use composition. Higher concentrations may become irritating.

The ratio of alpha-hydroxy acid enhancer to total antimicrobial lipid component is preferably at most 10:1, more preferably at most 5:1, and even more preferably at most 1:1. The ratio of alpha-hydroxy acid enhancer to total antimicrobial lipid component is preferably at least 1:20, more preferably at least 1:12, and even more preferably at least 1:5. Preferably the ratio of alpha-hydroxy acid enhancer to total antimicrobial lipid component is within a range of 1:12 to 1:1.

Beta-hydroxy Acids. A beta-hydroxy acid is typically a compound represented by the formula:

$R^7(CR^8OH)_n(CHR^9)_m COOH$ or 

wherein: $R^7$, $R^8$, and $R^9$ are each independently H or a (C1-C8)alkyl group (saturated straight, branched, or cyclic group), a (C6-C12)aryl, or a (C6-C12)aralkyl or alkaryl group (wherein the alkyl group is straight, branched, or cyclic), wherein $R^7$ and $R^8$ may be optionally substituted with one or more carboxylic acid groups; m=0 or 1; n=1-3 (preferably, n=1-2); and $R^{21}$ is H, (C1-C4)alkyl or a halogen.

Exemplary beta-hydroxy acids include, but are not limited to, salicylic acid, beta-hydroxybutanoic acid, tropic acid, and trethocanic acid. In certain preferred embodiments, the beta-hydroxy acids useful in the compositions of the present invention are selected from the group consisting of salicylic acid, beta-hydroxybutanoic acid, and mixtures thereof. Other suitable beta-hydroxy acids are described in U.S. Pat. No. 5,665,776 (Yu).

One or more beta-hydroxy acids may be used in the compositions of the present invention at a suitable level to produce the desired result. In a preferred embodiment, they are present in a total amount of at least 0.1 wt-%, more preferably at least 0.25 wt-%, and even more preferably at least 0.5 wt-%, based on the total weight of the ready to use composition. In a preferred embodiment, they are present in a total amount of no greater than 10 wt-%, more preferably no greater than 5 wt-%, and even more preferably no greater than 3 wt-%, based on the total weight of the ready to use composition. Higher concentrations may become irritating.

The ratio of beta-hydroxy acid enhancer to total antimicrobial lipid component is preferably at most 10:1, more preferably at most 5:1, and even more preferably at most 1:1. The ratio of beta-hydroxy acid enhancer to total antimicrobial lipid component is preferably at least 1:20, more preferably at least 1:15, and even more preferably at least 1:10. Preferably the ratio of beta-hydroxy acid enhancer to total antimicrobial lipid component is within a range of 1:15 to 1:1.

In systems with low concentrations of water, or that are essentially free of water, transesterification may be the principle route of loss of the fatty acid monoester and alkoxylated derivatives of these active ingredients and loss of carboxylic acid containing enhancers may occur due to esterification. Thus, certain alpha-hydroxy acids (AHA) and beta-hydroxy acids (BHA) are particularly preferred since these are believed to be less likely to transesterify the ester antimicrobial lipid or other ester by reaction of the hydroxyl group of the AHA or BHA. For example, salicylic acid may be particularly preferred in certain formulations since the phenolic hydroxyl group is a much more acidic alcohol and thus much less likely to react. Other particularly preferred compounds in anhydrous or low-water content formulations include lactic, mandelic, malic, citric, tartaric, and glycolic acid. Benzoic acid and substituted benzoic acids that do not include a hydroxyl group, while not hydroxyl acids, are also preferred due to a reduced tendency to form ester groups.

Other Carboxylic Acids. Carboxylic acids other than alpha- and beta-carboxylic acids are suitable for use in the enhancer component. These include alkyl, aryl, aralkyl, or alkaryl carboxylic acids typically having equal to or less than 12 carbon atoms. A preferred class of these can be represented by the following formula:

$$R^{10}(CR^{11}{}_2)_n COOH$$

wherein: $R^{10}$ and $R^{11}$ are each independently H or a (C1-C4)alkyl group (which can be a straight, branched, or cyclic group), a (C6-C12)aryl group, a (C6-C12) group containing both aryl groups and alkyl groups (which can be a straight, branched, or cyclic group), wherein $R^{10}$ and $R^{11}$ may be optionally substituted with one or more carboxylic acid groups; and n=0-3, preferably, n=0-2. Preferably, the carboxylic acid is a (C1-C4)alkyl carboxylic acid, a (C6-C12) aralkyl carboxylic acid, or a (C6-C12)alkaryl carboxylic acid. Exemplary acids include, but are not limited to, acetic acid, propionic acid, benzoic acid, benzylic acid, nonylbenzoic acid, and the like. Particularly preferred is benzoic acid.

One or more carboxylic acids may be used in the compositions of the present invention at a suitable level to produce the desired result. In a preferred embodiment, they are present in a total amount of at least 0.1 wt-%, more preferably at least 0.25 wt-%, even more preferably at least 0.5 wt-%, and most preferably at least 1 wt-%, based on the ready to use concentration composition. In a preferred embodiment, they are present in a total amount of no greater than 10 wt-%, more preferably no greater than 5 wt-%, and even more preferably no greater than 3 wt-%, based on the ready to use composition.

The ratio of the total concentration of carboxylic acids (other than alpha- or beta-hydroxy acids) to the total concentration of the antimicrobial lipid component is preferably within a range of 10:1 to 1:100, and more preferably 2:1 to 1:10, on a weight basis.

Chelators. A chelating agent (i.e., chelator) is typically an organic compound capable of multiple coordination sites with a metal ion in solution. Typically these chelating agents are polyanionic compounds and coordinate best with polyvalent metal ions. Exemplary chelating agents include, but are not limited to, ethylene diamine tetraacetic acid (EDTA) and salts thereof (e.g., EDTA(Na)$_2$, EDTA(Na)$_4$, EDTA(Ca), EDTA(K)$_2$), sodium acid pyrophosphate, acidic sodium hexametaphosphate, adipic acid, succinic acid, polyphosphoric acid, sodium acid pyrophosphate, sodium hexametaphosphate, acidified sodium hexametaphosphate, nitrilotris (methylenephosphonic acid), diethylenetriaminepentaacetic acid, 1-hydroxyethylene, 1,1-diphosphonic acid, and diethylenetriaminepenta-(methylenephosphonic acid). Certain carboxylic acids, particularly the alpha-hydroxy acids and beta-hydroxy acids, can also function as chelators, e.g., malic acid and tartaric acid.

Also included as chelators are compounds highly specific for binding ferrous and/or ferric ion such as siderophores, and iron binding proteins. Iron binding protein include, for example, lactoferrin, and transferrin. Siderophores include, for example, enterochlin, enterobactin, vibriobactin, anguibactin, pyochelin, pyoverdin, and aerobactin.

In certain preferred embodiments, the chelating agents useful in the compositions of the present invention include those selected from the group consisting of ethylenediaminetetraacetic acid and salts thereof, succinic acid, and mixtures thereof. Preferably, either the free acid or the mono- or di-salt form of EDTA is used.

One or more chelating agents may be used in the compositions of the present invention at a suitable level to produce the desired result. In a preferred embodiment, they are present in a total amount of at least 0.01 wt-%, more preferably at least 0.05-wt-%, even more preferably at least 0.1 wt-%, and even more preferably at least 1 wt-%, based on the weight of the ready to use composition. In a preferred embodiment, they are present in a total amount of no greater than 10 wt-%, more preferably no greater than 5 wt-%, and even more preferably no greater than 1 wt-%, based on the weight of the ready to use composition.

The ratio of the total concentration of chelating agents (other than alpha- or beta-hydroxy acids) to the total concentration of the antimicrobial lipid component is preferably within a range of 10:1 to 1:100, and more preferably 1:1 to 1:10, on a weight basis.

Phenolic Compounds. A phenolic compound enhancer is typically a compound having the following general structure:

wherein: m is 0 to 3 (especially 1 to 3), n is 1 to 3 (especially 1 to 2), each $R^{12}$ independently is alkyl or alkenyl of up to 12 carbon atoms (especially up to 8 carbon atoms) optionally substituted with 0 in or on the chain (e.g., as a carbonyl group) or OH on the chain, and each $R^{13}$ independently is H or alkyl or alkenyl of up to 8 carbon atoms (especially up to 6 carbon atoms) optionally substituted with 0 in or on the chain (e.g., as a carbonyl group) or OH on the chain, but where $R^{13}$ is H, n preferably is 1 or 2.

Examples of phenolic enhancers include, but are not limited to, butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, 4,6-di-tert-butyl-resorcinol, methyl paraben (4-hydroxybenzoic acid methyl ester), ethyl paraben, propyl paraben, butyl paraben, 2-phenoxyethanol, as well as combinations thereof. A preferred group of the phenolic compounds is the phenol species having the general structure shown above where $R^{13}$=H and where $R^{12}$ is alkyl or alkenyl of up to 8 carbon atoms, and n is 0, 1, 2, or 3, especially where at least one $R^{12}$ is butyl and particularly tert-butyl, and especially the non-toxic members thereof. Some of the preferred phenolic synergists are BHA, BHT, methyl paraben, ethyl paraben, propyl paraben, and butyl paraben as well as combinations of these.

One or more phenolic compounds may be used in the compositions of the present invention at a suitable level to produce the desired result. The concentrations of the phenolic compounds in medical-grade compositions may vary widely, but as little as 0.001 wt-%, based on the total weight of the composition, can be effective when the above-described esters are present within the above-noted ranges. In a preferred embodiment, they are present in a total amount of at least 0.01 wt-%, more preferably at least 0.10 wt-%, and even more preferably at least 0.25 wt-%, based on the ready to use composition. In a preferred embodiment, they are present in a total amount of no greater than 8 wt-%, more preferably no greater than 4 wt-%, and even more preferably no greater than 2 wt-%, based on the ready to use composition.

It is preferred that the ratio of the total phenolic concentration to the total concentration of the antimicrobial lipid component be within a range of 10:1 to 1:300, and more preferably within a range of 1:1 to 1:10, on a weight basis.

The above-noted concentrations of the phenolics are normally observed unless concentrated formulations for subsequent dilution are intended. On the other hand, the minimum concentration of the phenolics and the antimicrobial lipid components to provide an antimicrobial effect will vary with the particular application.

Monohydroxy Alcohols. An additional enhancer is a monohydroxy alcohol having 1-10 carbon atoms. This includes the lower (i.e., C1-C4) monohydroxy alcohols (e.g., methanol, ethanol, isopropanol, and butanol) as well as longer chain (i.e., C5-C10) monohydroxy alcohols (e.g., iosbutanol, t-butanol, octanol, and decanol). In certain preferred embodiments, the alcohols useful in the compositions of the present invention are selected from the group consisting of methanol, ethanol, isopropyl alcohol, and mixtures thereof.

One or more alcohols may be used in the compositions of the present invention at a suitable level to produce the desired result. In a preferred embodiment, the short chain (i.e., C1-C4) alcohols are present in a total amount of at least 10 wt-%, even more preferably at least 15 wt-%, even more preferably at least 20 wt-%, and even more preferably at least 25 wt-%, based on the total weight of the ready to use composition.

In a preferred embodiment, the (C1-C4)alcohols are present in a total amount of no greater than 90 wt-%, more preferably no greater than 70 wt-%, even more preferably no greater than 60 wt-%, and even more preferably no greater than 50 wt-%, based on the total weight of the ready to use composition.

For certain applications, lower alcohols may not be preferred due to the strong odor and potential for stinging and irritation. This can occur especially at higher levels. In applications where stinging or burning is a concern, the concentration of (C1-C4)alcohols is preferably less than 20 wt-%, more preferably less than 15 wt-%.

In another preferred embodiment longer chain (i.e., C5-C10)alcohols are present in a total amount of at least 0.1 wt-%, more preferably at least 0.25 wt-%, and even more preferably at least 0.5 wt-%, and most preferably at least 1.0%, based on the ready to use composition. In a preferred embodiment, the (C6-C10)alcohols are present in a total amount of no greater than 10 wt-%, more preferably no greater than 5 wt-%, and even more preferably no greater than 2 wt-%, based on the total weight of the ready to use composition.

Ether glycols. An additional enhancer is an ether glycol. Exemplary ether glycols include those of the formula:

wherein R'=H, a (C1-C8)alkyl, or a (C6-C12)aralkyl or alkaryl; and each R" is independently =H, methyl, or ethyl; and n=0-5, preferably 1-3. Examples include 2-phenoxyethanol, dipropylene glycol, triethylene glycol, the line of products available under the trade designation DOWANOL DB (di(ethylene glycol) butyl ether), DOWANOL DPM (di(propylene glycol)monomethyl ether), and DOWANOL TPnB (tri(propylene glycol) monobutyl ether), as well as many others available from Dow Chemical, Midland Mich.

One or more ether glycols may be used in the compositions of the present invention at a suitable level to produce the desired result. In a preferred embodiment, they are present in a total amount of at least 0.01 wt-%, based on the total weight of the ready to use composition. In a preferred embodiment, they are present in a total amount of no greater than 20 wt-%, based on the total weight of the ready to use composition.

Surfactants

Compositions of the present invention can include one or more surfactants to emulsify the composition and to help wet the surface and/or to aid in contacting the microorganisms. As used herein the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like. The surfactant can be cationic, anionic, nonionic, or amphoteric. This includes a wide variety of conventional surfactants; however, certain ethoxylated surfactants can reduce or eliminate the antimicrobial efficacy of the antimicrobial lipid component.

The exact mechanism of this is not known and not all ethoxylated surfactants display this negative effect. For example, poloxamer (polyethylene oxide/polypropylene oxide) surfactants have been shown to be compatible with the antimicrobial lipid component, but ethoxylated sorbitan fatty acid esters such as those sold under the trade name TWEEN by ICI have not been compatible. It should be noted that these are broad generalizations and the activity could be formulation dependent. One skilled in the art can easily determine compatibility of a surfactant by making the formulation and testing for antimicrobial activity as described in the Examples Section. Combinations of various surfactants can be used if desired.

It should be noted that certain antimicrobial lipds are amphiphiles and may be surface active. For example, certain antimicrobial alkyl monoglycerides described herein are surface active. For certain embodiments of the invention, the antimicrobial lipid component is considered distinct from a "surfactant" component.

Preferred surfactants are those that have an HLB (i.e., hydrophile to lipophile balance) of at least 4 and more preferably at least 8. Even more preferred surfactants have an HLB of at least 12. Most preferred surfactants have an HLB of at least 15.

Examples of the various classes of surfactants are described below. In certain preferred embodiments, the surfactants useful in the compositions of the present invention are selected from the group consisting of sulfonates, sulfates, phosphonates, phosphates, poloxamer (polyethylene oxide/polypropylene oxide block copolymers), cationic surfactants, and mixtures thereof. In certain more preferred embodiments, the surfactants useful in the compositions of the present invention are selected from the group consisting of sulfonates, sulfates, phosphates, and mixtures thereof.

One or more surfactants may be used in the compositions of the present invention at a suitable level to produce the desired result. In a preferred embodiment, they are present in a total amount of at least 0.1 wt-%, more preferably at least 0.5 wt-%, and even more preferably at least 1.0 wt-%, based on the total weight of the ready to use composition. Many of the compositions of the present invention are intended to be left on tissue for the desired indication, e.g., decolonizing nasal tissue or treating impetigo. Therefore, in order to avoid irritation in a preferred embodiment, they are present in a total amount of no greater than 10 wt-%, more preferably no greater than 5 wt-%, even more preferably no greater than 3 wt-%, and even more preferably no greater than 2 wt-%, based on the total weight of the ready to use composition. The ratio of the total concentration of surfactant to the total concentration of the antimicrobial lipid component is preferably within a range of 5:1 to 1:100, more preferably 3:1 to 1:10, and most preferably 2:1 to 1:3, on a weight basis.

Cationic Surfactants. Exemplary cationic surfactants include, but are not limited to, salts of optionally polyoxyalkylenated primary, secondary, or tertiary fatty amines; quaternary ammonium salts such as tetraalkylammonium, alkylamidoalkyltrialkylammonium, trialkylbenzylammonium, trialkylhydroxyalkylammonium, or alkylpyridinium halides (preferably chlorides or bromides) as well as other anionic counterions, such as but not limited to, alkyl sulfates, such as but not limited to, methosulfate and ethosulfate; imidazoline derivatives; amine oxides of a cationic nature (e.g., at an acidic pH).

In certain preferred embodiments, the cationic surfactants useful in the compositions of the present invention are selected from the group consisting of tetralkyl ammonium, trialkylbenzylammonium, and alkylpyridinium halides as well as other anionic counterions, such as but not limited to, C1-C4 alkyl sulfates, such as but not limited to, methosulfate and ethosulfate, and mixtures thereof.

Also particularly preferred are amine oxide surfactants including alkyl and alkylamidoalkyldialkylamine oxides of the following formula:

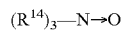

wherein $R^{14}$ is a (C1-C30)alkyl group (preferably a (C1-C14)alkyl group) or a (C6-C18)aralklyl or alkaryl group, wherein any of these groups can be optionally substituted in or on the chain by N-, O-, or S-containing groups such as amide, ester, hydroxyl, and the like. Each $R^{14}$ may be the same or different provided at least one $R^{14}$ group includes at least eight carbons. Optionally, the $R^{14}$ groups can be joined to form a heterocyclic ring with the nitrogen to form surfactants such as amine oxides of alkyl morpholine, alkyl piperazine, and the like. Preferably two $R^{14}$ groups are methyl and one $R^{14}$ group is a (C12-C16)alkyl or alkylamidopropyl group. Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Company.

Anionic Surfactants. Exemplary anionic surfactants include, but are not limited to, sarcosinates, glutamates, alkyl sulfates, sodium or potassium alkyleth sulfates, ammonium alkyleth sulfates, ammonium laureth-n-sulfates, laureth-n-sulfates, isethionates, glycerylether sulfonates, sulfosuccinates, alkylglyceryl ether sulfonates, alkyl phosphates, aralkyl phosphates, alkylphosphonates, and aralkylphosphonates. These anionic surfactants may have a metal or organic ammonium counterion. In certain preferred embodiments, the anionic surfactants useful in the compositions of the present invention are selected from the group consisting of:

1. Sultanates and Sulfates.

Suitable anionic surfactants include sulfonates and sulfates such as alkyl sulfates, alkylether sulfates, alkyl sulfonates, alkylether sulfonates, alkylbenzene sulfonates, alkylbenzene ether sulfates, alkylsulfoacetates, secondary alkane sulfonates, secondary alkylsulfates, and the like. Many of these can be represented by the formulas:

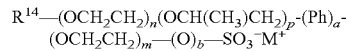

and

wherein: a and b=0 or 1; n, p, and m=0-100 (preferably 0-20, and more preferably 0-10); $R^{14}$ is defined as above provided at least one $R^{14}$ or $R^{15}$ is at least C8; $R^{15}$ is a (C1-C12)alkyl group (saturated straight, branched, or cyclic group) that may be optionally substituted by N, O, or S atoms or hydroxyl, carboxyl, amide, or amine groups; Ph=phenyl; and M is a cationic counterion such as H, Na, K, Li, ammonium, or a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. Preferably for this class, $R^{14}$ includes an alkylamide group such as $R^{16}$—C(O)N(CH$_3$)CH$_2$CH$_2$— as well as ester groups such as —OC(O)—CH$_2$— wherein $R^{16}$ is a (C8-C22)alkyl group (branched, straight, or cyclic group). Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14-C17)secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16)fatty acid available from Stepan Company under the trade designation ALPHASTEP PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company; dialkylsulfosuccinates such as dioctylsodiumsulfosuccinate available as Aerosol OT from Cytec Industries.

2. Phosphates and Phosphonates.

Suitable anionic surfactants also include phosphates such as alkyl phosphates, alkylether phosphates, aralkylphosphates, and aralkylether phosphates. Many may be represented by the formula:

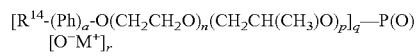

wherein: Ph, $R^{14}$, a, n, p, and M are defined above; r is 0-2; and q=1-3; with the proviso that when q=1, r=2, and q=2, r=1, and when q=3, r=0. As above, the ethylene oxide groups (i.e., the "n" groups) and propylene oxide groups (i.e., the "p" groups) can occur in reverse order as well as in a random, sequential, or block arrangement. Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J., and mixtures thereof.

Amphoteric Surfactants. Surfactants of the amphoteric type include surfactants having tertiary amine groups, which may be protonated, as well as quaternary amine containing zwitterionic surfactants. Those that have been particularly useful include:

1. Ammonium Carboxylate Amphoterics.

This class of surfactants can be represented by the following formula:

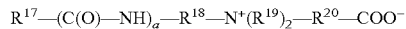

wherein: a=0 or 1; $R^{17}$ is a (C7-C21)alkyl group (saturated straight, branched, or cyclic group), a (C6-C22)aryl group, or a (C6-C22)aralkyl or alkaryl group (saturated straight, branched, or cyclic alkyl group), wherein $R^{17}$ may be optionally substituted with one or more N, O, or S atoms, or one or more hydroxyl, carboxyl, amide, or amine groups; $R^{19}$ is H or a (C1-C8)alkyl group (saturated straight, branched, or cyclic group), wherein $R^{19}$ may be optionally substituted with one or more N, O, or S atoms, or one or more hydroxyl, carboxyl, amine groups, a (C6-C9)aryl group, or a (C6-C9)aralkyl or alkaryl group; and $R^{18}$ and $R^{20}$ are each independently a (C1-C10)alkylene group that may be the same or different and may be optionally substituted with one or more N, O, or S atoms, or one or more hydroxyl or amine groups.

More preferably, in the formula above, $R^{17}$ is a (C1-C18) alkyl group, $R^{19}$ is a (C1-C2)alkyl group preferably substituted with a methyl or benzyl group and most preferably with a methyl group. When $R^{19}$ is H it is understood that the surfactant at higher pH values could exist as a tertiary amine with a cationic counterion such as Na, K, Li, or a quaternary amine group.

Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1L, MACKAM 2L, and MACKAM 151L, respectively, from McIntyre Group Ltd.).

2. Ammonium Sulfonate Amphoterics.

This class of amphoteric surfactants are often referred to as "sultaines" or "sulfobetaines" and can be represented by the following formula

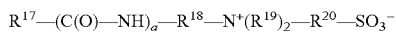

wherein $R^{17}$-$R^{20}$ and "a" are defined above. Examples include cocamidopropylhydroxysultaine (commercially available as MACKAM 50-SB from McIntyre Group Ltd.). The sulfoamphoterics may be preferred over the carboxylate amphoterics since the sulfonate group will remain ionized at much lower pH values.

Nonionic Surfactants. Exemplary nonionic surfactants include, but are not limited to, alkyl glucosides, alkyl polyglucosides, polyhydroxy fatty acid amides, sucrose esters, esters of fatty acids and polyhydric alcohols, fatty acid alkanolamides, ethoxylated fatty acids, ethoxylated aliphatic acids, ethoxylated fatty alcohols (e.g., octyl phenoxy polyethoxyethanol available under the trade name TRITON X-100 and nonyl phenoxy poly(ethyleneoxy) ethanol available under the trade name NONIDET P-40, both from Sigma, St. Louis, Mo.), ethoxylated and/or propoxylated aliphatic alcohols (e.g., that available under the trade name BRIJ from ICI, Wilmington, Del.), ethoxylated glycerides, ethoxylated/propoxylated block copolymers such as PLURONIC and TETRONIC surfactants available from BASF, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants (e.g., those available under the trade names FLUORAD-FS 300 from Minnesota Mining and Manufacturing Co., St. Paul, Minn., and ZONYL from Dupont de Nemours Co., Wilmington, Del.), and polymerizable (reactive) surfactants (e.g., SAM 211 (alkylene polyalkoxy sulfate) surfactant available under the trade name MAZON from PPG Industries, Inc., Pittsburgh, Pa.). In certain preferred embodiments, the nonionic surfactants useful in the compositions of the present invention are selected from the group consisting of Poloxamers such as PLURONIC from BASF, sorbitan fatty acid esters, and mixtures thereof Hydrophilic Component Compositions of the present invention can include a hydrophilic or water-soluble component to help solubilize and/or physically stabilize the enhancer component in the composition and/or to enhance the antimicrobial efficacy and/or the speed of antmicrobial efficacy. Incorporation of a sufficient amount of hydrophilic component in hydrophobic ointments can increase the antimicrobial activity both in terms of speed of kill and extent of kill. While not intended to be bound by theory, the incorporation of the hydrophilic component may allow more of the antimicrobial lipid component to be available at the surface or to more rapidly diffuse to the surface of the ointment during use.

In general, the ratio of total hydrophilic component to total hydrophobic component (water insoluble ingredients)

is at least 5:95 weight ratio (wt/wt), preferably at least 10:90 wt/wt, more preferably at least 15:85 wt/wt, and even more preferably at least 20:80 wt/wt. Levels as high as 30:70, 40:60, and 50:50 wt/wt of total hydrophilic component to total hydrophobic component (water insoluble ingredients) or higher may be appropriate for certain compositions.

Certain compositions may be solutions, emulsions (one liquid/gel/paste dispersed in another liquid/gel/paste), dispersions (solid in liquid/paste/gel), or combinations thereof.

A hydrophilic material is typically a compound that has a solubility in water of at least 7 wt-%, preferably at least 10 wt-%, more preferably at least 20 wt-%, even more preferably at least 25 wt-%, and even more preferably at least 40 wt-%, at 23° C. Most preferably, a hydrophilic component is infinitely miscible with water at 23° C.

Exemplary hydrophilic components include, but are not limited to, water, polyhydric alcohols, lower alkyl ethers (i.e., having a sufficiently small number of carbon atoms to meet the solubility limit above), N-methylpyrrolidone, alkyl esters (i.e., having a sufficiently small number of carbon atoms to meet the solubility limit above), and the lower monohydroxy alcohols discussed above as enhancers, as well as combinations thereof. Thus, a lower monohydroxy alcohol can function as both a hydrophilic compound and an enhancer. Preferably, the hydrophilic components include polyhydric alcohols, lower alkyl ethers, and short chain esters. More preferably, the hydrophilic components include polyhydric alcohols.

Suitable polyhydric alcohols (i.e., organic compounds having more than one hydroxyl group) have a molecular weight of less than 500, preferably less than 400, and more preferably less than 200. Examples of polyhydric alcohols include, but are not limited to, glycerol, propylene glycol, dipropylene glycol, tripropylene glycol, polypropylene glycol, polyethylene glycol, diethylene glycol, pentaerythritol, trimethylolpropane, trimethylolethane, trimethylolbutane, sorbitol, mannitol, xylitol, pantothenol, ethylene glycol adducts of polyhydric alcohol, propylene oxide adducts of polyhydric alcohol, 1,3-butanediol, dipropylene glycol, diglycerine, polyglycerine, erythritol, sorbitan, sugars (e.g., sucrose, glucose, fructose, mannose, xylose, saccharose, trehalose), sugar alcohols, and the like. Certain preferred polyhydric alcohols include glycols (i.e., those containing two hydroxyl groups) including glycerin and propylene glycol. Certain other preferred polyhydric alcohols include sucrose, xylitol, mannitol, and sorbitol.

Ethers include materials such as dimethylisosorbide, polyethylene glycol and methoxypolyethylene glycols, block and random copolymers of ethylene oxide and propylene oxide, and laureth-4. Alkyl esters include triacetin, methyl acetate, methyl lactate, ethyl lactate esters, esters of polyethoxylated glycols, and combinations thereof.

In certain preferred embodiments, the hydrophilic components useful in the compositions of the present invention include those selected from the group consisting of glycols, and in particular glycerin and propylene glycol, and mixtures thereof. Most preferably, the hydrophilic component is selected to match the polyhydric alcohol portion of any fatty acid monoester of a polyhydric alcohol antimicrobial present. For example, if the antimicrobial agent was glycerolmonolaurate (monolaurin) the most preferred hydrophilic component is glycerin. In this manner, any transesterification reaction that may occur with the carrier solvent does not produce an undesirable by-product. If there are other components in the composition that may esterify with hydroxylfunctional hydrophilic components, conditions are selected to minimize this occurrence. For example, the components are not heated together for extended periods of time, and/or the pH is close to neutral if possible, etc.

One or more hydrophilic materials may be used in the compositions of the present invention at a suitable level to produce the desired result. In certain preferred embodiments that also include the hydrophobic component as the primary component (i.e., the component used in the greatest amount and referred to as a "vehicle"), the hydrophilic component is present in a total amount of at least 0.1%, preferably at least 1 wt-%, more preferably at least 4 wt-%, and even more preferably at least 8 wt-%, based on the weight of the ready to use composition. In certain embodiments, for example, when faster rate of kill is desired, higher levels of hydrophilic component may be employed. In these cases the hydrophilic component is present in a total amount of at least 10 wt-%, more preferably at least 20 wt-%, and even more preferably at least 25 wt-%.

In a preferred embodiment, the hydrophilic component is present in a total amount of no greater than 70 wt-%, preferably no greater than 60 wt-%, more preferably no greater than 40 wt-%, even more preferably no greater than 30 wt-%, based on the ready to use composition. When the hydrophilic component is present in the greatest amount it is referred to as a "vehicle."

For certain applications, it may be desirable to formulate the antimicrobial lipid in compositions including a hydrophilic component vehicle that is thickened with soluble, swellable, or insoluble (e.g. insoluble) organic polymeric thickeners or inorganic thickeners such as silica, fumed silica, precipitated silica, silica aerogel and carbon black, and the like; other particle fillers such as calcium carbonate, magnesium carbonate, kaolin, talc, titanium dioxide, aluminum silicate, diatomaceous earth, ferric oxide and zinc oxide, clays, and the like; ceramic microspheres or glass microbubbles; ceramic microspheres suc as those available under the tradenames "ZEOSPHERES" or "Z-LIGHT" from 3M Company, St. Paul, Minn. The above fillers can be used alone or in combination.

If water is used in certain embodiments, it is preferably present in an amount of less than 20%, preferably less than 10 wt-%, more preferably less than 5 wt-%, and even more preferably less than 2 wt-%, based on the ready to use composition. This helps the chemical stability of the compositions and may reduce irritation. For certain other embodiments, water can be used in a much greater amount, and can even be the primary component, as long as the composition is highly viscous. Preferably, such highly viscous compositions have a viscosity of at least 500 centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Most preferred compositions meet these viscosity values even after heating to 32° C. or even 35° C. or as high as 37° C. to ensure when in contact with mammalian tissue the compositions remain substantive.

In some embodiments of the present invention, the compositions have a viscosity of at least 20 cps, preferably at least 100 cps, when measured by the Viscosity Test described herein. Higher viscosities are preferred to reduce migration as well as to provide substantivity (resistance to removal by fluids) to ensure long-term antimicrobial activity.

Hydrophobic Component

Certain preferred compositions of the present invention also include one or more hydrophobic materials. In certain embodiments, the hydrophobic component can be the same as the antimicrobial lipid component. A hydrophobic material is typically an organic compound, which at 23° C. is a liquid, gelatinous, semisolid or solid and has a solubility in water of less than 5% by weight, preferably less than 1% by weight, more preferably less than 0.5% by weight, and even more preferably less than 0.1% by weight. These materials include compounds typically considered emollients in the cosmetic art.

Examples of general emollients include, but are not limited to, short chain (i.e., C1-C6) alkyl or (C6-C12)aryl esters of long (i.e., C8-C36) straight or branched chain alkyl or alkenyl alcohols or acids and polyethoxylated derivatives of the alcohols; short chain (i.e., C1-C6) alkyl or (C6-C12) aryl esters of (C4-C12)diacids or (C4-C12)diols optionally substituted in available positions by —OH; (C2-C18)alkyl or (C6-C12)aryl esters of glycerol, pentaerythritol, ethylene glycol, propylene glycol, as well as polyethoxylated derivatives of these; (C12-C22)alkyl esters or (C12-C22)ethers of polypropylene glycol; (C12-C22)alkyl esters or (C12-C22) ethers of polypropylene glycol/polyethylene glycol copolymer; and polyether polysiloxane copolymers. Additional examples of hydrophobic components include cyclic dimethicones, including volatile cyclic silicones such as D3 and D4, polydialkylsiloxanes, polyaryl/alkylsiloxanes, silicone copolyols, long chain (i.e., C8-C36) alkyl and alkenyl esters of long (i.e., C8-C18) straight or branched chain alkyl or alkenyl alcohols or acids, long chain (i.e., C8-C36) alkyl and alkenyl amides of long straight or branched chain (i.e., C8-C36) alkyl or alkenyl amines or acids; hydrocarbons including straight and branched chain alkanes and alkenes such as isoparafins (e.g., isooctane, isododecane, isooctadecane, etc.), squalene, and mineral oil, polysiloxane polyalkylene copolymers, dialkoxy dimethyl polysiloxanes; (C12-C22)alkyl and (C12-C22)alkenyl alcohols, and petroleum derived alkanes such as isoparafins, petrolatum, petrolatum USP, as well as refined natural oils (especially NF or USP grades) such as olive oil NF, cotton seed oil, peanut oil, corn oil, seasame oil, safflower oil, soybean oil, and the like, and blends thereof. In certain preferred embodiments, the hydrophobic components useful in the compositions of the present invention include those selected from the group consisting of petrolatum USP and short chain (i.e., C1-C6) alkyl or (C6-C12)aryl esters of long (i.e., C8-C36) straight or branched chain alkyl or alkenyl alcohols or acids and polyethoxylated derivatives of the alcohols; short chain (i.e., C1-C6) alkyl or (C6-C12)aryl esters of (C4-C12)diacids or (C4-C12)diols optionally substituted in available positions by —OH (such as diisopropyladipate, diisopropylsebacate); (C1-C9)alkyl or (C6-C12)aryl esters of glycerol, pentaerythritol, ethylene glycol, propylene glycol (such as glyceryl tricaprylate/caprate); and mixtures thereof. For certain particularly preferred embodiments, the hydrophobic component is petrolatum.

One or more hydrophobic materials may be used in the compositions of the present invention at a suitable level to produce the desired result. In a preferred embodiment (in which the compositions include very little or no water), the hydrophobic component is present in a total amount of at least 50 wt-%, more preferably at least 70 wt-%, and even more preferably at least 80 wt-%, based on the ready to use composition. In a preferred embodiment, the hydrophobic component is present in a total amount of no greater than 99 wt-%, more preferably no greater than 95 wt-%, and even more preferably no greater than 92 wt-%, based on the ready to use composition. When the hydrophobic component is present in the greatest amount it is referred to as a "vehicle." In those formulations where the hydrophobic component(s) and the hydrophilic component(s) are present at the same concentrations, the continuous phase is considered the "vehicle."

Optional Additives

Compositions of the present invention may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, anti-parasitic agents, antipruritics, astringents, local anaesthetics, steroids, non-steroidal anti-imflammatory agents, or other anti-inflammatory agents), or may contain materials useful in physically formulating various dosage forms of the present invention, such as excipients, dyes, perfumes, lubricants, thickening agents, stabilizers, skin penetration enhancers, preservatives, or antioxidants.

It will be appreciated by the skilled artisan that the levels or ranges selected for the required or optional components described herein will depend upon whether one is formulating a composition for direct use, or a concentrate for dilution prior to use, as well as the specific component selected, the ultimate end-use of the composition, and other factors well known to the skilled artisan.

It will also be appreciated that additional antiseptics, disinfectants, or antibiotics may be included and are contemplated. These include, for example, addition of metals such as silver, copper, zinc; iodine and iodophors; chlorhexidine and its various salts such as chlorhexidine digluconate; polyhexamethylenebiguanide, parachlorometaxylenol, triclosan, antimicrobial quaternarly amines including polymeric quaternary amines, "azole" antifungal agents including clortrimazole, miconazole, econazole, ketoconazole, and salts thereof; and the like. Antibiotics such as neomycin sulfate, bacitracin, mupirocin, polymyxin, rifampin, tetracycline, and the like, also may be included. Preferred compositions, however, are free of antibiotics due to the chance of resistance formation.

Formulations and Methods of Preparation

Many of the compositions of the present invention have exceptional broad spectrum antimicrobial activity and thus are generally not terminally sterilized but if necessary may be sterilized by a variety of industry standard techniques. For example, it may be preferred to sterilize the compositions in their final packaged form using electron beam. It may also be possible to sterilize the sample by gamma radiation or heat. Other forms of sterilization may be acceptable. It may also be suitable to include preservatives in the formulation to prevent growth of certain organisms. Suitable preservatives include industry standard compounds such as Parabens (methyl, ethyl, propyl, isopropyl, isobutyl, etc), 2 bromo-2 nitro-1,3 diol; 5 bromo-5-nitro-1,3 dioxane, chlorbutanol, diazolidinyl urea; iodopropylnyl butylcarbamate, phenoxyethanol, halogenated cresols, methylchloroisothiazolinone and the like, as well as combinations of these compounds.

The compositions of the present invention preferably adhere well to mammalian tissues (particularly, skin, mucosal tissue, and wounds), in order to deliver the antimicrobial to the intended site over a prolonged period even in the presence of perspiration, drainage (e.g., mucosal secretions), or mild lavage. The compositions are typically non-aqueous, although high viscosity compositions can include a large amount of water. The component in the greatest amount (i.e., the vehicle) in the formulations of the invention may be any conventional vehicle commonly used for topical treatment of human or animal skin. The formulations are typically selected from one of the following three types: (1) anhydrous or nearly anhydrous formulations with a hydrophobic vehicle (i.e., the hydrophobic component, which can include one or more hydrophobic compounds, is present in the greatest amount); (2) anhydrous or nearly anhydrous formulations with a hydrophilic vehicle (i.e., the hydrophilic component, which can include one or more hydrophilic compounds, is present in the greatest amount); and (3) highly viscous water-based formulations. These are discussed below.

(1) Anhydrous or Nearly Anhydrous Formulations with a Hydrophobic Vehicle. In certain preferred embodiments of the present invention, the compositions include an antimicrobial lipid component in a hydrophobic vehicle in combination with surfactant(s), an enhancer component, and a small amount of a hydrophilic component. In most instances the enhancers are not soluble in the hydrophobic component at room temperature although they may be at elevated temperatures. The hydrophilic component is generally present in a sufficient amount to stabilize (preferably to solubilize) the enhancer(s) in the composition. For example, when formulating with organic acid enhancers or certain solid surfactants in petrolatum many enhancers and surfactants will dissolve into the petrolatum at temperatures above 85° C.; however, upon cooling, the enhancer and/or surfactant crystals or precipitates back out of solution making it difficult to produce a uniform formulation. If at least 0.1%, and preferably at least 1.0%, more preferably at least 5%, and most preferably at least 10 wt-%, of a hydrophilic compound (e.g., a glycol) is added, a stable formulation can be obtained. It is believed that these formulations produce an emulsion in which the enhancer and/or surfactant is dissolved, emulsified, or dispersed in the hydrophilic component which is emulsified into the hydrophobic component(s). These compositions are stable upon cooling and centrifuging.

The hydrophilic component also helps to stabilize many of the surfactants used in preferred formulations. For example, dioctylsulfosuccinate sodium salt (DOSS) dissolves in glycerin at elevated temperatures and helps keep the DOSS physically stable in the composition. Furthermore, it is believed that incorporation of the hydrophilic component in the formulation improves the antimicrobial activity. The mechanism for this is unknown; however, it may speed the release of the enhancer component and/or the antimicrobial lipid component.

The water content of these formulations is preferably less than 20%, preferably less than 10 wt-%, more preferably less than 5 wt-%, and even more preferably less than 2 wt-%, in order to minimize hydrolysis of any ester based antimicrobial lipid present.

Furthermore, it has been found that it is particularly desirable where the antimicrobial lipid component includes an ester to use either glycerin or propylene glycol in the hydrophilic component. It is most preferred to use a hydrophilic compound that is identical to the glycol portion of the antimicrobial lipid, e.g., propylene glycol with the propylene glycol esters and glycerin with the glycerin esters. In this manner, transesterification of the antimicrobial lipid ester with the hydrophilic compound will not result in additional chemical species present. In fact, there is some evidence to show that use of glycerolmonolaurate, which is 95% pure, when formulated with glycerin as a hydrophilic compound results in formation of additional glycerol monolaurate due to transesterification of the diester with the glycerin to produce two moles of the monoester. For this reason, it may be possible to initially formulate with lower grade glycerin ester that contains considerable levels of diester present, as long as it transesterifies during manufacture and/or storage to produce a formulation that includes less than 15% diester and preferably less than 5% diester based on the total weight of antimicrobial lipid present.

These formulations can be relatively easily manufactured by first heating the hydrophobic component to 85° C., adding in the surfactant, hydrophilic component, and enhancer component, cooling to 65° C., and adding the antimicrobial lipid component above its melting point. Alternatively, the enhancer component can be predissolved in the hydrophilic component (optionally along with the surfactant) and added to the hydrophobic component either before or after addition of the antimicrobial lipid component. If either the antimicrobial lipid component or the hydrophobic component are solids at room temperature this is done at the minimum temperature necessary to melt all components. Exposure of ester containing antimicrobial lipids to enhancers that include either acid or ether groups to elevated temperatures for extended periods of time should be avoided to prevent transesterification reactions (unless this is deliberate in the case of utilizing lower purity fatty acid esters in combination with glycol hydrophilic components to produce the monoesters as discussed above).

Thus, the present invention provides methods of manufacture. One preferred method involves: dissolving the enhancer component in the hydrophilic component; combining the hydrophobic vehicle and the hydrophilic component with the enhancer component dissolved therein with mixing to form a mixture; optionally heating the hydrophobic vehicle to a temperature sufficient to form a pourable liquid (which for many hydrophobic vehicles this is above its melting point) before or after combining it with the hydrophilic component and enhancer component; adding the antimicrobial lipid component to the mixture; and cooling the mixture before or after adding the antimicrobial lipid component.

The hydrophilic component may or may not be present in the formulations that include a hydrophobic vehicle. Thus, another preferred method of manufacture involves: combining the enhancer component and the hydrophobic vehicle with mixing to form a mixture; optionally heating the hydrophobic vehicle to a temperature sufficient to form a pourable liquid (which for many hydrophobic vehicles is above its melting point) before or after combining it with the enhancer component; adding the antimicrobial lipid component to the mixture with mixing; and cooling the mixture before or after adding the antimicrobial lipid component.

Surprisingly, it has been found that these compositions are significantly less irritating than formulations using completely hydrophilic components. In blind human trials participants were asked to instill 0.5 gram (g) of ointments based on hydrophobic components (e.g., petrolatum) that include an AHA enhancer, surfactant, and 10% hydrophilic component (e.g., glycerin) as well as ointments based on hydrophilic components (e.g., PEG 400) using the same enhancer and surfactant. Surprisingly, the ointments based on the hydrophobic component were preferred by 100% of the participants.

The viscosity of these formulations intended for use on skin or in the anterior nares is preferably relatively high to prevent excessive drainage off the treatment site. In this regard the viscosity is preferably at least 500 Centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test.

Most preferably, the formulations intended for use on skin, anterior nares, or where drainage would be a concern are essentially gelatinous at room temperature, having a significant yield point such that they do not flow readily at temperatures below 35° C. The viscosity is measured using the viscosity test described herein. Certain gelatinous vehicles may also have a characteristic temperature at which they "melt" or begin to dramatically lose viscosity. Preferably this is higher than body temperature also to ensure that excess drainage of the composition of the treatment site does not occur. Therefore, the melting point of the composition is preferably greater than 32° C., more preferably greater than 35° C., and even more preferably greater than 37° C. The melting point is taken as the lowest temperature at which the viscosity becomes dramatically less or is equal to or less than 100,000 cps.

Similarly the viscosity and/or melt temperature can be enhanced by either incorporating a crystalline or semicrystalline hydrophobic carrier such as a higher melting petrolatum, addition of an insoluble filler/thixotrope, or by addition of a polymeric thickener (e.g., a polyethylene wax in a petrolatum vehicle). Polymeric thickeners may be linear, branched, or slightly crosslinked. It is important for comfort that the formulations are relatively soft and that they spread easily to allow easy application, especially over a wound, rash, or infected area or in the anterior nares. A particularly preferred vehicle for use on skin, in the anterior nares, or in other areas where high viscosity is desirable is white petrolatum USP having a melting point greater than 40° C.

(2) Water in Oil Emulsions. Antimicrobial lipid components of this invention can be formulated into water-in-oil emulsions in combination with enhancer(s) and surfactant(s). Particularly preferred compositions comprise at least 35%, preferably at least 40%, more preferably at least 45%, and most preferably at least 50%, by weight oil phase. As used herein the oil phase includes all components which are either not soluble in water or preferentially soluble in the oil(s) present at 23° C. One method of preparing these emulsions is described in Applicants' Assignee's Copending U.S. patent application Ser. No. 09/966,511, filed on Sep. 28, 2001. Generally speaking, the hydrophobic component (oil) is mixed in Container A along with any emulsifier(s) optionally including polymeric emulsifiers and heated to a temperature sufficient to ensure a homogenous composition and subsequent stable emulsion. The temperature is typically raised to at least 60° C., preferably to at least 80° C., and more preferably to 100° C. or more. In a separate Container B, the hydrophilic ingredients are mixed, including one or more of the following: water, hydrophilic component, enhancer(s), surfactant(s), and acids/bases to adjust the pH of the final composition. The contents of container B are heated to a temperature sufficient to ensure a stable final emulsion composition without significantly degrading any of the components, typically to a temperature greater than 40° C., preferably greater than 50° C., and more preferably greater than 60° C. While hot, container B is added to container A using a high shear mixer. The composition may be continuously mixed until cool (e.g., to a temperature of less than 40° C.) or it can be allowed to sit as long as the contents remain uniformly mixed. If the antimicrobial lipid is heat sensitive, it is added with mixing during the cooling down period. If it is not heat sensitive, it may be added to either container A or container B. The viscosity of these compositions may be adjusted by altering the levels of emulsifier; changing the ratio of water to oil phase; selection of the oil phase (e.g., select from an oil (hydrophobic component), which is more or less viscous); incorporation of a polymeric or particulate thickener, etc.

(3) Hydrophilic Vehicle. Antimicrobial lipid components of this invention can be formulated into a hydrophilic component such as that based on the hydrophilic compounds (discussed above) optionally in combination with the enhancer(s) and surfactant(s). Particularly preferred are polyethylene glycols (PEGs), including blends of different molecular weight PEGs, optionally containing one or more glycols. When using a hydrophilic component as the vehicle (i.e., the component used in the greatest amount, which can include one or more hydrophilic compounds), it should be preferably selected to maintain viscosity and melt temperature characteristics similar to those stated above for the anhydrous or nearly anhydrous formulations using a hydrophobic vehicle.

Similarly the viscosity can be enhanced by either incorporating a crystalline or semicrystalline hydrophilic compound such as a PEG of sufficient molecular weight, addition of an insoluble filler/thixotrope, or by addition of a polymeric thickener. Polymeric thickeners may be linear, branched, or slightly crosslinked. It is desirable for comfort that the formulations are relatively soft and that they spread easily to allow easy application, especially in the anterior nares or over a wound, rash, or infected area. For this reason, a particularly preferred vehicle is based on a blend of a liquid or semisolid PEG (PEG 400-1000) with a more crystalline PEG (PEG 1000-2000). Particularly preferred is a blend of PEG 400 with PEG 1450 in a ratio of 4:1.

In certain preferred embodiments of the present invention, the compositions are in the form of an ointment or cream. That is, the compositions are in the form of a relatively viscous state such that they are suitable for application to nasal passageways. Preferably, such compositions have a viscosity of at least 500 Centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Preferred formulations have high viscosity even after application to mammalian tissue at 32-37° C.

(4) Water-based Formulations. Aqueous compositions of the present invention are those in which water is present in the greatest amount, thereby forming the "vehicle." For these systems it is particularly important that a relatively high viscosity be imparted to the composition to ensure that the antimicrobial composition is not rapidly dispersed off the afflicted area. These formulations also adhere well to tissue and thus deliver the antimicrobial to the intended site over a prolonged period even in the presence of perspiration, drainage (e.g., mucosal secretions), or mild lavage. Such a high viscosity can be imparted by a thickener system. The thickener system of the invention is compatible with the antimicrobial lipid composition described above in order to provide suitable antimicrobial efficacy, chemical and physical stability, acceptable cosmetic properties, and appropriate viscosity for retention in the afflicted area.

Preferably, compositions of this invention have a viscosity of at least 500 Centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Preferred formulations have high viscosity even after application to mammalian tissue at 32-37° C. Because certain optional ingredients, such as enhancers, hydrophilic compounds, hydrophobic compounds, and the like, may effect the viscosity (either positively or negatively), the measured viscosity is that of the final composition.

Preferred thickener systems used in the compositions of the present invention are capable of producing viscoelastic compositions that are very stable. By varying the amount and type of thickener, the degree of elasticity can be adjusted from almost a purely viscous composition to a highly elastic and even gel-like composition. If emollients are added, increasing the elasticity and/or yield stress of the system imparts added stability to prevent separation of immiscible emollients. Excessive elasticity, however, is not preferred because an excessively elastic composition usually does not provide a cosmetically appealing product.

Significantly, thickener systems used in the present invention are capable of achieving high viscosities at relatively low total concentrations. The total concentration of the thickener system is preferably less than 8 wt-%, more preferably less than 5 wt-%, and most preferably less than 3 wt-%, based on the total weight of the ready to use composition. Preferably, the total concentration of the thickener system can be as little as 0.5 wt-%, based on the total weight of the composition. For certain embodiments, however, the total concentration of thickener system is greater than 1 wt-%, based on the total weight of the ready to use composition.

The thickener system can include organic polymers or inorganic thixotropes such as silica gel, clays (such as betonite, laponite, hectorite, montmorrillonite and the like), as well as organically modified inorganic particulates materials, and the like. As used herein, an organic polymer is considered part of the thickener system if its presence in the composition results in an increase in the viscosity of the composition. Certain polymers that do not have these characteristics may also be present in the composition but do not contribute significantly to the viscosity of the composition. For purposes of this invention, they are not considered part of the thickener system. For example, certain nonionic polymers such as lower molecular weight polyethylene glycols (e.g., those having a molecular weight of less than 20,000) do not increase the viscosity of the composition significantly. These are considered part of the hydrophilic component, for example, rather than part of the thickener system.

The thickener system can be prepared from one or more nonionic, cationic, anionic, zwitterionic, or associative polymers as long as they are compatible with the antimicrobial lipid and enhancer components of the composition. For example, certain acidic enhancers such as those that include carboxylic acid groups are most effective in their protonated form. This requires that the composition has an acidic pH. For this reason, many anionic thickeners based on neutralized carboxylic acid groups would not be suitable. For example, Carbopol-type thickeners based on polyacrylic acid salts do not typically thicken well at pH values of less than 5 and certainly less than a pH of 4.5. Therefore, at lower pH values (i.e., when acidic enhancers are present) if the aqueous compositions are thickened with anionic polymers, the polymers are preferably based on sulfonic acid, sulfate, phosphonic acid, or phosphate groups. These polymers are able to thicken at much lower pH values due to the lower pKa of these acid groups.

Preferred polymers of this class include ARISTOFLEX HMB (ammonium acryloyldimethyltaurate/beheneth-25 methacrylate crosspolymer) and ARISTOFLEX ASV (ammonium acryloyldimethyltaurate/NVP copolymer) from Clariant Corporation. Other preferred sulfonic acid polymers are those described in U.S. Pat. No. 5,318,955. Preferably, the compositions that include an acidic enhancer component are thickened using cationic or nonionic thickeners since these perform well at low pH. In addition, many of the nonionic and cationic polymers can tolerate higher levels of salts and other additives and still maintain high viscosity.

A preferred group of nonionic polymeric thickeners include modified celluloses, guar, xanthan gum, and other natural polymers such as polysaccharides and proteins, associative polymers based on nonionic ethylenically unsaturated monomers wherein at least one comonomer has at least 16 carbon atoms, and polymers based on ethylenically unsaturated monomers selected from the group consisting of acrylates, acrylamides, vinyl lactams, vinyl acetate and its hydrolyzed derivatives, methyl vinyl ethers, styrene, and acrylonitrile.

A preferred group of cationic polymeric thickeners include cationically modified celluloses, quaternized natural amino-functional polymers, and polymers based on ethylenically unsaturated monomers selected from the group consisting of acrylates, acrylamides, vinyl lactams, vinyl acetates, methyl vinyl ethers, styrene, and acrylonitrile.

Cationic polymers for use in the compositions of this invention can be selected from both permanently charged quaternary polymers (those polymers with quaternary amines such as Polyquaternium 4, 10, 24, 32, and 37, described below) as well as protonated primary, secondary, and tertiary amine functional polymers that have been protonated with a suitable protonic acid. Preferred protonated cationic polymers are based on tertiary amines. The protonated cationic polymers are preferably protonated with suitable acids that will not result in undue skin irritation. These include, for example, (C1-C10)alkylcarboxylic acids optionally substituted by oxygen (e.g., acetic acid, alpha-hydroxy acids such as lactic acid, gluconic acid, benzoic acid, mandelic acid, and the like), (C1-C10)alkylsulfonic acids (e.g., methylsulfonic acid and ethylsulfonic acid), (C1-C10)alkylhydrogensulfates (e.g., methylhydrogensulfate) and mineral acids (e.g., hydrochloric acid, hydrobromic acid, sulfuric acid, phosphoric acid, and the like).

The charge on protonated cationic polymers is pH dependent. For this reason, in order to ensure the polymer is sufficiently protonated, the pH is adjusted appropriately and should be in the range of preferably 2-9.5, more preferably 2-8, and most preferably 2.5-7.5. The pH of preferred compositions that include acidic enhancers should be lower and is typically 2-5, and preferably 2-4. It should be noted that it is not necessary to have all of the amines on a particular polymer protonated. The level of protonation will to a certain extent be pH dependent. With certain polymers in order to obtain optimum thickening with low skin irriation it may be beneficial to only protonate a small percentage of the available amine groups while with other polymers it may be beneficial to protonate substantially all of the amine groups. This will be easily determined by one skilled in the art.

The quaternary, tertiary, secondary, and primary amine functional polymers may be chosen from natural polymers, modified natural polymers, as well as synthetic polymers. These polymers may be soluble or swellable in the aqueous solvent. Furthermore, these polymers may also possess hydrophobic side chains and thus be associative polymers.

Polymers can be classified as soluble, swellable, or associative in the aqueous compositions. Some polymers may fall into one or more of these classes. For example, certain associative polymers can be soluble in the aqeuous system. Whether they are considered soluble, swellable, or associative in the aqueous system, suitable polymers for use in the compositions of the present invention may be film forming or not. Film forming polymers may retain the active antimicrobial component at the afflicted site for longer periods of time. This may be desirable for certain applications. For example, some film forming polymers may produce compositions that could not be easily washed off with water after being applied and dried.

As used herein, a soluble polymer is one that in dilute solution (i.e., 0.01-0.1 wt-% in the desired aqueous solvent system defined as containing water and any other hydrophilic compounds), after heating for a sufficient time to ensure solubilization of any potentially soluble components, has no significant observable particles of greater than 1 micron in particle size, as determined by light scattering measurements using, for example, Malvern Masterisizer E Laser Particle Size Analyzer available from Malvern Co., Boston, Mass.

As used herein, a swellable polymer is one that in dilute solution (i.e., 0.01-0.1 wt-% in the desired aqueous solvent system), after heating for a sufficient time to ensure solubilization of any potentially soluble components, has a significant (i.e., detectable) number of observable particles of greater than 1 micron in particle size, as determined by light scattering measurements using, for example, Malvern Masterisizer E Laser Particle Size Analyzer.

As used herein, an associative polymer is one that has greater than 2 hydrophobic chains per polymer molecule of greater than 16 carbon atoms. Examples of such polymers are as follows.

Soluble Polymers—Cationic Natural Polymer Derivatives. Cationic modified cellulosic polymers are reported in the literature to be soluble in water. Such polymers have been found to be useful in the present invention. The most preferred modified cellulose products are sold under the trade names CELQUAT (National Starch and Chemicals Corp., Bridgewater, N.J.) and UCARE (Amerchol Corporation, Edison, N.J.). CELQUAT is a copolymer of a polyethoxylated cellulose and dimethyldiallyl ammonium chloride and has the Cosmetic, Toiletry and Fragrance Association (CTFA) designation Polyquaternium-4.

An alkyl modified quaternary ammonium salt of hydroxyethyl cellulose and a trimethyl ammonium chloride substituted epoxide can also be used. The polymer conforms to the CTFA designation Polyquaternium 24 and is commercially available as QUATRISOFT LM-200 from Amerchol Corp., Edison, N.J.

A particularly suitable type of cationic polysaccharide polymer that can be used is a cationic guar gum derivative, such as guar hydroxypropyltrimonium chloride (Commercially available from Rhone-Poulenc under the trade designation JAGUAR).

Soluble Polymers—Cationic Synthetic Polymers. Synthetic cationic linear polymers useful in the present invention are preferably quite high in cationic charge density—generally having greater than 10 wt-% cationic monomer, preferably greater than 25 wt-%, and more preferably greater than 50 wt-%. This ensures a good cosmetic feel and may actually improve water solubility. In general, the polymers useful in the present invention have sufficient molecular weight to achieve thickening at generally less than 5 wt-% polymer, but not too high that the lotion/cream/ointment feels slimy and stringy. While the composition of the polymer will dramatically affect the molecular weight at which sufficient thickening will occur, the polymers preferably have a molecular weight of at least 250,000 daltons, and more preferably at least 500,000 daltons. The polymers preferably have a molecular weight of no greater than 3,000,000 daltons, and more preferably no greater than 1,000,000 daltons. The homopolymers are preferably prepared from methacryloyloxyalkyl trialkyl ammonium salt, acryloyloxyalkyl trialkyl ammonium salt, and/or quaternized dialkylaminoalkylacrylamidine salt. Preferably the polymers are copolymers of at least two monomers selected from the group consisting of trialkylaminoalkyl acrylate and methacrylate salts, dialkyldiallyl ammonium salts, acrylamidoalkyltrialkyl salts, methacrylamidoalkyltrialkyl salts, and alkyl imidazolinium salts, N-vinyl pyrrolidinone, N-vinyl caprolactam, methyl vinyl ether, acrylates, methacrylates, styrene, acrylonitrile, and combinations thereof. Typically, for the salts the counterions are preferably $F^-$, $Cl^-$, $Br^-$, and $CH_3(CH_2)_nSO_4^-$ where n=0-4.

A variety of quaternary copolymers of varying quaternization, can be synthesized based on homo or copolymers of amino acrylates with methyl, ethyl, or propyl side chains. These monomers could also be copolymerized with other nonionic monomers including quaternary acrylic homopolymers, such as homopolymers of 2-methacryloxyethyl trimethylammonium chloride and 2-methacryloxyethyl methyl diethyl ammonium bromide; and copolymers of quaternary acrylate monomers with a water-soluble monomers, such as Petrolite Product No. Q-0043, a proprietary copolymer of a linear quaternary acrylate and acrylamide at high molecular weight (4-5 million MW).

Another useful soluble cationic polymer is N,N-dimethylaminopropyl-N-acrylamidine (which is quaternized with diethylsulfate) bound to a block of polyacrylonitrile. This block copolymer is available under the trade designation Hypan QT-100 from Lipo Chemicals Inc., Paterson, N.J. It is quite effective at thickening aqueous systems and has a good cosmetic feel. This polymer as received, however, has an objectionable amine odor. The odor could probably be masked with the proper fragrance, but is preferably removed prior to formulation (e.g., with a solvent cleaning process) so that the formulation can be supplied without fragrance. Preferred compositions are free of fragrances and colorants.

Suitable cationic polymers include, for example, copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370); copolymers of 1-vinyl-2-pyrrolidine and dimethylaminoethyl methacrylate, referred to in the industry (CTFA) as Polyquaternium-11. This material is available commercially from ICI Corp., Wayne, N.J., under the trade designation GAFQUAT; cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively.

Soluble Polymers-Nonionic. A variety of cellulosic ethers are reported in the literature to be soluble in water. Materials in this class that are nonionic and have been shown to be useful include: methylhydroxypropylcellulose, available as BENECEL MP 943 from Aqualon, Wilmington, Del.; hydroxypropylcellulose, available as KLUCEL (LF, GF, MF, HF) from Aqualon; hydroxybutylmethylcellulose (3.5% hydroxybutyl and 30% methoxyl) from Scientific Polymer Products, Ontario, N.Y.; and hydroxyethylcelluloses, available under the trade designation NATROSOL from Aqualon. Xanthan gum, guar, locust bean gum, and other polysaccharides may also be suitable. These polymers may be produced from plant sources or can be produced through microbial cell culture. Polyvinyl alcohol (PVA) also may be suitable. For example, PVA made from polyvinyl acetate which has been hydrolyzed to 87% is highly water soluble at room temperature. Those with higher percent hydrolysis become progressively more crystalline and may need to be heated to get into solution. Protein thickeners such as gelatin and pectin may also be useful.

Amine oxide polymers such as those described in U.S. Pat. No. 6,123,933 and those commercially available under the trade designation DIAFORMER Z-711, Z-712, Z-731, and Z-751 from Clariant Corp. are useful. Additionally, zwitterionic polymers, such as methacryloyl ethyl betaine/acrylate copolymer that are commercially available under the trade designation DIAFORMER Z-400 from Clariant Corp. can also be used. Zwitterionic polymers described in U.S. Pat. No. 6,590,051 may also be useful.

Carboxylic acid functional polymers including naturally occurring carboxylic acid functional polymers such as hyaluronic acid and derivatives of natural polymers such as carboxymethylcellulose, alginic acid and other alginate polymers, Fucogel (a polysaccharide consisting of three mono-saccharides, fucose, galactose, and galacturonic acid), hyaluronic acid, and the like, also may be useful. Synthetic polymers may also be useful, such as those based on carboxylic acid, phosphonic acid, or sulfonic acid functional monomers, including but not limited to, polymers derived from acrylic acid, methacrylic acid, maleic anhydride, itaconic anhydride, sodium AMPS (the sodium salt of 2-acrylamido-2-methylpropane sulfonic acid), sulfopropyl acrylate or methacrylate, sulphomethylated acrylamide, allyl sulphonate, sodium vinyl sulphonate, combinations thereof, or other water-soluble forms of these or other polymerizable carboxylic or sulphonic acids.

Swellable Polymers. Many swellable polymers, which are slightly crosslinked, function as viscosifiers in aqueous solvent systems. In general, these swellable polymers are preferred because they tend to be far less "slimy" going on and once the hands perspire and are exposed to water after treatment. Excessive crosslinking will result in polymers that do not swell sufficiently to increase the viscosity of the composition. In order to ensure adequate swelling, if a chemical crosslinker is used, the concentration of crosslinker is quite low, e.g., less than 1000 parts per million (ppm), and preferably less than 500 ppm, based on the weight of the dry polymer.

A class of crosslinked polymers suitable for use in the compositions of the present invention include acrylamide and at least one other quaternary monomer selected from the group consisting of trialkylaminoalkylacrylate and methacrylate salts, dialkyldiallyl ammonium salts, acrylamidoalkyltrialkyl ammonium salts, methacrylamidoalkyltrialkyl ammonium salts, and monomers that include imidazolinium salts. The counterions are preferably $F^-$, $Cl^-$, $Br^-$, and $CH_3(CH_2)_nSO_4^-$ where n=0-4. Other comonomers may also be added including N-vinyl pyrrolidone, N-vinyl caprolactam, methyl vinyl ether, acrylates, methacrylates, styrene, and the like. A particularly preferred polymer is a poly(2-methacryloxyethyl trimethyl ammonium chloride) polydimethylaminoethyl methacrylate, which conforms to the CTFA designation Polyquaternium 37. Another preferred polymer includes acrylamide and methacryloyloxyethyl trimethyl ammonium chloride, which conforms to the CTFA designation Polyquaternium 32. These are commercially available from Allied Colloids Inc. of Suffolk, Va. as SALCARE SC95, SC96, and SC92.

Other swellable polymers (i.e., slightly crosslinked polymers) can be prepared using ionizing radiation to crosslink. For example, polymers of N-vinyl lactams, such as N-vinyl pyrrolidone, when exposed to gamma radiation increase in molecular weight and may actually crosslink. This crosslinking allows for more efficient thickening (less polymer required to achieve a certain viscosity) and an improved cosmetic feel. Other polymers that when exposed to gamma radiation result in crosslinking, include polymers such as LUVIQUAT HM 552 (copolymers of vinylimidazolium methochloride and vinylpyrrolidone, which conforms to the CTFA designation Polyquaternium-16), and GAFQUAT HS-100 (vinylpyrrolidone/methacrylamidopropyltrimethylammonium chloride copolymer which conforms to the CTFA designation Polyquaternium-28).

Chemical crosslinking using polyunsaturated monomers such as diallyl maleate may also prove useful. Other suitable crosslinkers are multi-ethylenically unsaturated compounds wherein the ethylenic groups are vinyl groups (including substituted vinyl groups, such as isopropenyl groups), allyl groups, and/or methallyl groups, which groups are bonded to nitrogen or oxygen atoms. Vinyl, allyl, and methallyl groups, as used herein, include substituted derivatives. Exemplary compounds include divinyl, diallyl, or dimethallyl esters, ethers, amides, or ureas. Specific examples are disclosed in U.S. Pat. No. 5,225,473 (Duan) and U.S. Pat. No. 4,931,282 (Asmus et al.).

A range of crosslinked polyvinylpyrrolidone (PVP) materials have been prepared via covalent crosslinking with diallyl maleate or by radiation crosslinking of linear PVP powders. Crosslinked PVP prepared under these techniques can produce colloidal particles which are highly swellable in aqueous solutions and thereby produce viscous solutions. The polymers are also nonionic and have excellent compatibility with cationic excipients.

Anionic swellable polymeric thickeners may also be useful. As described above preferred anionic polymers for use with antimicrobial compositions which include carboxylic acid functional enhancers (and are thus formulated at lower pH) are polymers having sulfonic acid, sulfonate, phosphonic acid, or phosphate groups.

Associative Polymers. Associative polymers can be used to thicken the compositions of the present invention as well. Such polymers thicken as a result of hydrophobic or Van de Waals association of hydrophobic side chains. Such associative polymers can form viscous to gelled aqueous solutions despite their relatively low molecular weights. Polymers that are alcoholic soluble can be modified by the addition of a long chain hydrophobic group. A preferred class of such associative polymers are based on nonionic ethylenically unsaturated monomers wherein at least one comonomer has at least 16 carbon atoms.

An example is cetyl hydroxyethylcellulose, available as NATROSOL PLUS from Aqualon, which utilizes an associative mechanism to enhance the viscosity it produces. Grafted side chains of cetyl alkyl groups can associate with neighboring alkyl hydrophobes. These interpolymer associations can dramatically increase the viscosification efficiency of the polymer. Longer chain alklyl, alkenyl, and aralkyl groups may also be suitable. For example, another preferred associative polymer is Arsitoflex HMB, which is ammonium acryloyldimethyltaurate/beheneth-25 methacrylate crosspolymer and is available from Clariant Corp.

(5) Neat Compositions. The compositions of the present invention also may be delivered to the treatment site in a neat form or in a volatile solvent that rapidly evaporates to leave behind a neat composition. Such compositions may be solid, semisolid, or liquid. In the case where the compositions are solid, the antimicrobial lipid and/or the enhancer and/or the surfactant may optionally be microencapsulated to either sustain the delivery or facilitate manufacturing a powder, which is easily delivered. Alternatively, the composition can be micronized into a fine powder without the addition of other components or it may optionally contain fillers and other ingredients that facilitate powder manufacture. Suitable powders include, but are not limited to, calcium carbonate, calcium phosphate, various sugars, starches, cellulose derivatives, gelatin, and polymers such as polyethylene glycols.

When hydrophobic antimicrobial lipids are used, a method for micronizing a hydrophobic agent may be used wherein the hydrophobic agent is dissolved in an effective amount of a first solvent that is free of polymer (such as the method described in U.S. Pat. No. 6,746,635). The hydrophobic agent and the solvent form a mixture having a continuous phase. A second solvent and then an aqueous solution are introduced into the mixture. The introduction of the aqueous solution causes precipitation of the hydrophobic agent and produces a composition of micronized hydrophobic agent having an average particle size of 1 micron or less. The particle size for use in delivery to the nose or other tissue may be significantly larger to direct delivery to the proper site. For example, to deliver the antimicrobial powder to the nose, nasal cavities, and/or throat without passing into the lungs, larger particles may be required.

Bioadhesive polymers optionally may be added to neat compositions as well as the other physical forms. Numerous suitable bioadhesive polymers are discussed in International Publication No. WO 93/21906. Representative bioadhesive polymers of particular interest include bioerodible hydrogels described by H. S. Sawhney et al., in Macromolecules, 26:581-587 (1993), including polyhyaluronic acids, casein, gelatin, glutin, polyanhydrides, polyacrylic acid, alginate, chitosan, poly(methyl methacrylates), poly(ethyl methacrylates), poly butylmethacrylate), poly(isobutylmethacrylate), poly(hexlmethacrylate), poly(isodecl methacrylate), poly (lauryl methacrylate), poly(phenyl methacrylate), poly(methyl acrylate), poly(isopropyl acrylate), poly(isobutyl acrylate), and poly(octadecl acrylate). Preferred polymers are polyacrylic acid (e.g., CARBOMER polymers) and poly (fumaric-co-sebacic)acid. Other bioadhesive and bioerodible polymers are described in U.S. Pat. No. 6,746,635. Particularly preferred are slightly crosslinked polyacrylic acids such as those sold under the CARBOPOL brand by BF Goodrich.

The antimicrobial compositions also may include suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

The neat compositions according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. Those of skill in the art can readily determine the various parameters and conditions for producing aerosols without resort to undue experimentation. Inhaled medications are preferred in some embodiments because of the direct delivery to the lung. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Techniques for preparing aerosol delivery systems are well known to those of skill in the art. Generally, such systems should utilize components which will not significantly impair the biological properties of the agent (see, for example, Sciarra and Cutie, "Aerosols," in Remington's Pharmaceutical Sciences, 18th edition, 1694-1712 (1990)).

The compounds may also be formulated in rectal or vaginal compositions such as suppositories or retention enemas, e.g., containing conventional suppository bases such as cocoa butter or other glycerides.

Viscosity

Certain preferred compositions of the present invention have a viscosity of at least 500 Centipoise (cps) for ease of application topically. More preferably, compositions of the present invention have a viscosity of at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). Lower viscosity compositions can be used, however, in certain applications, such as for the treatment of middle ear infection and chronic sinusitis. For example, afflictions of the middle ear (e.g., otitis media or infection of the middle ear) may be treated with compositions of the present invention having a viscosity lower than 1000 cps more readily by administration through the nose and into the Eustachian tubes. The viscosity is measured by the Viscosity Test described herein. Preferred compositions meet the above viscosity limitations even when warmed to 32° C. Most preferred compositions meet the above viscosity limitations even when warmed to 35° C., or as high as 37° C.

In some embodiments of the present invention, the compositions have a viscosity of at least 20 cps, preferably at least 100 cps, when measured by the Viscosity Test described herein. Higher viscosities are preferred to reduce migration as well as to provide substantivity (resistance to removal by fluids) to ensure long-term antimicrobial activity.

Delivery Methods and Devices

Antimicrobial compositions of the present invention can be provided to a medical professional in a single composite formulation or in multiple parts. For example, a composition can be provided in two parts (e.g., in two separate containers or two separate compartments of the same container), one part containing the antimicrobial lipid component and one part containing the enhancer. Other components of the composition can be combined with either one of the two parts. Alternatively, the other components can be included in a third part.

In other embodiments, a composition can be provided in two parts and the antimicrobial lipid component can be made in situ. For example, a monoglyceride could be formed in-situ from a di- or tri-glyceride in the presence of a lipase such as a mammalian or bacterially derived lipase. This may occur on the tissue or prior to application to the tissue.

Topical treatment regimens according to the practice of this invention include applying a safe and effective amount of the compositions described herein directly to the infected or at-risk skin, wound, or mucous membrane; particularly, the nasal nares and passages that are particularly susceptible to microbial contamination.

Compositions of the present invention can be delivered using a variety of techniques. Typically, the compositions are delivered to the skin and/or mucosal tissue in a manner that allows them to penetrate into the skin and/or mucosal tissue, as opposed to through the tissue into the blood stream. This concentrates the compositions locally at the site in need of treatment. This delivery can be accomplished by spraying, dipping, wiping, dropping, pouring, toweling, inhaling, or the like, onto the area to be treated.

In the methods of the present invention, the compositions may be provided as a formulation suitable for delivery to mammalian tissue (e.g., skin and/or mucosal surfaces). Suitable formulations can include, but are not limited to, creams, gels, foams, ointments, lotions, balms, waxes, salves, solutions, suspensions, dispersions, water in oil or oil in water emulsions, microemulsions, pastes, powders, oils, lozenges, boluses, and sprays, and the like.

The compositions may be sprayed from a pressurized container. The pressure may be supplied by an external means such as squeezing the container, through the use of a mechanical pump, or with the use of a propellant. Suitable propellants include chlorofluorocarbons (CFCs), hydrochlorofluorocarbons (HCFCs), hydrofluorocarbons (HFCs), hydrofluoroethers (HFEs), perfluorinated alkanes, and (C1-C5)alkanes, such as propane and butane, as well as nitrous oxide and dimethyl ether. Preferred propellants are lower alkanes such as propane, butane, isobutene, as well as HCFCs.

If delivered as a foam, the composition may be dispensed from an aerating dispenser such as the F2 Finger Pump Foamer available from Air Spray International Pompano Beach, Fla. Alternatively, the foam may be generated using a suitable propellant such as those described above.

In some embodiments, compositons of the present invention can be formulated into various consumer products, such as deodorants, shampoos, shower gels, detergents, household cleaning products, etc.

For very high viscosity formulations the composition may be delivered in essentially a solid dosage form by placing the composition in or on the tissue to be treated. For example, a small suppository type delivery could be placed into the anterior nares for eradication of Staphylococcus sp.

Various other modes of administration can be used as well known to one of skill in the art depending on the desired location for contact of the antimicrobial compositions of the present invention. For example, afflictions of the middle ear (e.g., otitis media or infection of the middle ear) may be treated with compositions of the present invention by administration through the nose and into the Eustachian tubes or they can be instilled directly into the middle ear through the tympanic membrane. The formulations may traverse the tympanic membrane with the aid of a syringe or do so by diffusion. Penetration enhancers may be used to enhance diffusion across the tympanic membrane.

For application to skin or mucosal tissue, for example, the compositions may be applied directly to the tissue from a collapsible container such as a flexible tube, blow/fill/seal container, pouch, capsule, etc. In this embodiment, the primary container itself is used to dispense the composition directly onto the tissue or it can be used to dispense the composition onto a separate applicator. For example, for delivery to the nose or topical tissue, the composition could be dispensed directly from a tube and spread by a number of means including squeezing the outside of the nose together repeatedly, wiping with the tip of the tube or with a separate device such as a spatula, cotton, rayon, or other natural or synthetic based fiber swab.

Other application devices may also be suitable including applicators with foam tips, brushes, and the like. Importantly, the applicator must be able to deliver the requisite amount of composition to the tissue. Therefore, in most instances applicator devices such as webs and swabs are coated on the applicator web at greater than 50% by weight of the dry web and preferably in excess of 100% by weight of the dry web. (On a swab this would include the weight only of the web and not the applicator stick.)

The collapsible containers may be made in a number of single layer, laminate, or coextruded constructions. Materials of construction may include polyolefins such as low, medium, or high density polyethylene including low and linear low density polyethylene, polypropylene, as well as copolymers of ethylene and/or propylene with other polar or non-polar comonomers; polyamides such as nylons; polyesters such as polyethylene terephalate, polybutyleneterephalate, polyethylenenaphthalate; polyurethanes; polyacrylates; and the like. In some constructions it may be desirable to include a barrier material to prevent evaporation of one or more components of the formulation. Suitable barrier materials include polyesters (e.g., polyethylene terephthalate, polyethylene naphthalate, polybutylene terephalate, and the like), fluorinated layers such as polytetrafluoroethylene (PTFE, e.g., TEFLON), polyamides (e.g., nylon), chlorotrifluoroethylene (ACLAR), polyvinylidene fluoride, as well as copolymers of perflourinated monomers with partially fluorinated monomers such as copolymers of tetrafluoroethylene/hexafluoropropylene/vinylidene fluoride (THV Fluorothermoplastic from Dyneon Company), polyvinylchloride, polyvinylidene chloride (PVDC, e.g., SARAN HB), ethylene vinyl alcohol (EVOH), polyolefins (e.g., polyethylene, high density polyethylene, polypropylene, and combinations thereof). Oriented and biaxially oriented polymers may be particularly preferred.

Particularly preferred barrier constructions include metallic foil barriers such as aluminum foil laminates, HDPE, PET, PETG, PEN laminates of polyester and polyolefin (in particular PET/HDPE or HDPE/PET/HDPE), laminates of PET and EVOH, biaxially oriented nylon, PVDC, Nylon/EVOH/Nylon (OXYSHIELD OUB-R), chlorotrifluoroethylene and laminates thereof, ceramic layer including silicon oxide ($SiO_x$ where x=0.5-2 and preferably 1-2) coated thermoplastics, and ceramic coated PET (CERAMIS available from CCL Container/Tube Division, Oak Ridge, N.J.).

Compositions of the present invention may be applied to a mucosal surface with the use of a delivery device such as cervical caps, diaphragms and solid matrices such as tampons, cotton sponges, cotton swabs, foam sponges, and suppositories.

Accordingly, compositions of the present invention can also be delivered from cloth, sponges, paper products (e.g., paper towels, towellettes, and wipes), tampons, undercast padding, and dental floss, for example.

In some embodiments, an applicator may be used to place the device and/or antimicrobial composition in the proper location, for example, on the mucosal surface of a vagina, nasal cavity, rectum, or the like. Examples of such applicators include, for example, cardboard or plastic tube applicators commonly used for inserting tampons or suppositories.

The compositions of the present invention can be delivered from various substrates for delivery to the tissue. For example, the compositions can be delivered from a wipe or pad which when contacted to tissue will deliver at least a portion of the composition to the tissue. For application to nasal cavities the compositions may be provided by a non-woven swab such as a "Q-tip" brand cotton swab, into a foam tip applicator, and the like. The substrate may be used to deliver the composition essentially instantaneously or may be left in contact with the tissue. For example, a substrate in a tubular form could be delivered to the anterior nares using a suitable applicator and left in the anterior nares. The annular nature of the device is designed to allow delivery of the active while allowing the patient to freely breathe through the nose.

Also, compositions of the present invention can be coated onto medical devices that contact mammalian tissue (e.g., skin, mucous membranes, wounds, etc.). Examples of such devices include catheters such as urinary tract catheters and vascular access catheters.

Antimicrobial compositions of the present invention can be formulated for additional controlled release (beyond that provided by the compositions previously discussed) if desired. For example, the antimicrobial lipid component may be formulated into compatible liposomes, microcapsules, microglobules, microbeads, and/or microspheres such as those made from natural polymers including, but not limited to, polysaccharides, agar, starch and starch derivatives, cellulose and cellulose derivatives, and synthetic polymers such as polyolefins (e.g., polyethylene and polypropylene), polystyrene, polyacrylates, and the like, as well as inorganic materials such as clays and zeolites. The antimicrobial lipid component may also be formulated into multiple emulsions such as oil-in-water-in-oil emulsions or water-in-oil-in-water emulsions where the oil is an organic oil or a silicone base oil. In addition, water soluble or swellable polymers can be combined with the antimicrobial lipid in a soluble or swollen state, dried, and added to the various compositions to further sustain release. If a prolonged release of the antimicrobial lipid is desired it also may be useful to incorporate a hydrophobic component in which the antimicrobial lipid is soluble.

Topical antimicrobial treatment regimens according to the practice of this invention include applying an effective amount of the compositions described herein directly to the infected or at-risk mammalian tissue (particularly, skin or mucous membrane); particularly, the nasal nares and passages that are particularly susceptible to microbial contamination. Compositions of the present invention can be delivered using a variety of techniques. Typically, the compositions are delivered to the mammalian tissue (particularly, the skin and/or mucosal tissue) in a manner that allows them to penetrate into the tissue, as opposed to through the tissue into the blood stream. This concentrates the compositions locally at the site in need thereof. This can be accomplished by spraying, dipping, wiping, dropping, pouring, toweling, or the like, onto the area to be treated.

If a composition of the present invention includes certain poloxamer block copolymers of ethylene oxide and propylene oxide generally having greater than 60 mol-% polyethylene oxide (such as those available under the trade names PLURONIC F127 and F108 from BASF Corp.), as well as certain modified cellulose polymers, and is applied topically, for example, thermally induced gelation can occur. Thus, various components can be selected for use in compositions of the present invention to produce a desired application effect.

The dose and frequency of application will depend on many factors including the condition to be treated, the concentration of antimicrobial lipid and enhancer, the microbe to be killed, etc. Typically, the compositions will be delivered in dosages of at least 10 milligrams per square centimeter (mg/cm$^2$) of tissue, preferably at least 20 mg/cm$^2$ of tissue, more preferably at least 30 mg/cm$^2$ of tissue, and most preferably at least 50 mg/cm$^2$ of tissue, for most applications. Application can be made once, or several (e.g., 2-4) times daily for one or more days. Typically, the composition is applied 1 or 2 times/day for 1-7 days. For example, decolonization of the anterior nares may require a dose of 0.25 gram (g) per nares applied 1-3 times per day for 1-5 days. Treatment of impetigo may require 0.5 g/15 cm$^2$ (33 mg/cm$^2$ of tissue) applied 1-3 times/day for 3-10 days.

Additional Antimicrobial Components and Delivery Systems

The present invention also provides a delivery system for an antimicrobial component (e.g., antimicrobial lipids as well as other antimicrobial agents, particularly antiseptics). Such delivery systems include a hydrophobic component and a hydrophilic component, wherein the composition has a viscosity of at least 500 cps, and further wherein the hydrophobic component forms the greatest portion of the composition by weight. Alternatively, such delivery systems include a hydrophobic component, a hydrophilic component, and a surfactant, wherein the hydrophobic component forms the greatest portion of the composition by weight.

Methods of delivery of antimicrobial components are also provided using such delivery systems (i.e., compositions). Such methods involve applying to a surface a composition that includes a hydrophobic component and a hydrophilic component, herein the composition has a viscosity of at least 500 cps, and further wherein the hydrophobic component forms the greatest portion of the composition by weight. Alternatively, the method can involve applying to a surface a composition that includes a hydrophobic component, a hydrophilic component, and a surfactant, wherein the hydrophobic component forms the greatest portion of the composition by weight.

In such delivery systems, the antimicrobial component can include an antimicrobial lipid component, such as that described herein. Alternatively (or additionally), the antimicrobial component can include other antimicrobial agents, particularly other antiseptics. Examples of suitable antiseptics include, for example, peroxides, (C6-C14)alkyl carboxylic acids and alkyl ester carboxylic acids, antimicrobial natural oils, as described in Applicants' Assignee's U.S. Patent Application Publication No. US 2006/0051385; halogenated phenols, diphenyl ethers, bisphenols (including but not limited to p-chloro m-xylenol (PCMX) and triclosan), and halogenated carbanilides described in Applicants' Assignee's U.S. Pat. No. 8,198,326; digluconate, diacetate, dimethosulfate, and dilactate salts; polymeric quaternary ammonium compounds such as polyhexamethylenebiguanide; silver and various silver complexes; small molecule quaternary ammonium compounds such as benzalkoium chloride and alkyl substituted derivatives; di-long chain alkyl (C8-C18)quaternary ammonium compounds; cetylpyridinium halides and their derivatives; benzethonium chloride and its alkyl substituted derivatives; and octenidine described in Applicants' Assignee's U.S. Pat. No. 9,028,852; and compatible combinations thereof.

Although the detailed description of illustrative embodiments provided herein (particularly with respect to enhancers, surfactants, other additives, and for making such compositions) specifically refer to an antimicrobial lipid component, such description also applies to other antimicrobial agents, particularly antiseptics.

Test Protocols

Antimicrobial Kill Rate Test

Antimicrobial compositions were challenged with test cultures of Methicillin Resistant *Staphyloccus aureus* (MRSA) #MS 16266 and *Staphylococcus aureus* (*S. aureus*), ATCC #25923 (commercially available from American Type Culture Collection, Rockville, Md.), *Escherichia coli* (*E. coli*), ATCC #11229, and *Pseudomonas aeruginosa* (*Pseudomonas* ae.), ATCC #15442.

Bacteria Culture Preparation:

Bacteria were grown in Tryptic Soy Broth (TSB) (commercially available from Difco, Detroit, Mich.) at 35° C. for 18-24 hours (hrs). A 0.3 milliliter (ml) culture suspension was spread on the surface of a Tryptic Soy Agar plate that was incubated at 35° C. for 18-24 hrs. Bacterial cells were harvested from the agar plate with a glass L-rod by adding 3 ml of TSB and were transferred into a snap cap 5 ml polypropylene culture tube. The resulting cell suspension was called the working culture.

Ointment Test Procedure:

A 50 ml centrifuge tube was filled with 10 ml of each ointment antimicrobial composition. The tube was placed in a temperature controlled water bath equipped with stirring capability. The temperature of the composition was adjusted to 40° C.+/−2° C. where most of the compositions became softened and could be easily mixed. Other compositions may require higher or lower temperatures. Importantly, the temperature should not be increased above about 45° C. at which point the bacteria will perish from temperature effects. It should be confirmed that the temperature did not kill the bacteria in the absence of the antimicrobial composition.

Liquid Test Procedure:

A 25 ml Erlenmeyer flask containing a magnetic stirring bar was filled with 20.0 ml of a liquid antimicrobial composition. The flask was placed in a temperature controlled water bath equipped with stirring capability. The magnetic stirrer was turned on and temperature of the composition was adjusted to 23° C.+/−2° C.

Exposure of Bacteria to the Compositions:

At the start of each exposure time, 0.1 ml of Methicillin Resistant *Staphyloccus aureus*, *Staphylococus aureus*, *Escherichia coli*, or *Pseudomonas aeruginosa* working culture was added to the antimicrobial composition. The exposure times were 2 minutes, 5 minutes and 10 minutes. At the end of each exposure time, 1 ml of suspension was transferred to a test tube containing 9 ml Letheen broth (VWR Scientific, Batavia, Ill.) at 23° C. or 40° C. ($10^{-1}$ cell suspension). After vortexing, the neutralized $10^{-1}$ cell suspension was further diluted to $10^{-2}$ by transferring 1 ml into 9 ml Letheen broth tubes. From each of the two dilutions, 0.1 ml volume was plated onto a TSA plate and spread with the L-rod producing $10^{-2}$ and $10^{-3}$ dilutions. The plates were incubated at 35° C.±2° C. for 48 hours (hrs) and colony-forming units (CFU) were counted and recorded. The procedure was repeated using three to five replicate samples of each composition. The diluted bacterial suspensions were plated in duplicate.

Data Analysis:

Microbial kill rate was reported as a $\log_{10}$ reduction which was determined by calculating the difference between the $\log_{10}$ of the initial inoculum count and the $\log_{10}$ of the inoculum count after exposure to compositions or components of the composition for 2-minute ($T_2$), 5-minute ($T_5$), and 10-minute ($T_{10}$) intervals.

The two duplicate plates at the selected dilution level were averaged and the initial inoculum count was calculated using the following formula:

Initial Inoculum Count=$T_0$=Ave. CFU of 3 replicates×1/dilution level×0.005

Where the sample inoculums were diluted (0.1 ml in 10 ml of the compositions, the initial inoculum were reduced by 0.1 ml/10 ml, which equals 0.010).

For the test plates of each organism at each time period, the CFU's on all the $10^{-2}$ and $10^{-3}$ plates were counted. The dilution level that had counts between 25 and 250 was determined. The two duplicate plates at the selected dilution level were averaged and the test plate count at the given time was calculated using the following formula:

$T_2, T_5,$ and $T_{10}$=CFU of 3 replicates×1/dilution level where the plate count of 3 replicates are at 2 minute, 5 minute, and 10 minute intervals, respectively.

For the compositions the log reduction was determined by taking the logarithm to the base 10 of $T_0$, $T_z$, $T_5$, and $T_{10}$ and using the following formulas:

Log reduction at 2 minutes=$\log_{10}T_0-\log_{10}T_2$

Log reduction at 5 minutes=$\log_{10}T_0-\log_{10}T_5$

Log reduction at 10 minutes=$\log_{10}T_0-\log_{10}T_{10}$

The average of the replicates was calculated by averaging the log reductions at each time period.

Aging Study Using Gas Chromatography

Antimicrobial Compositions were prepared and while in a well-mixed, liquid state, were poured into individual vials to solidify. The zero time ($T_0$) vials were refrigerated at 4° C. and the other vials were placed in a LAB LINE Orbital Environmental Incubator and incubated at either 23° C. or 40° C. and 65° C. at 200 RPM. Compositions incubated at 65° C. were in the liquid state. These compositions were incubated with and without shaking to see if agitation contributed to loss of GML. One vial of each composition was removed after 7 days and after 4 weeks. After they were removed, they were shaken until they solidified and refrigerated at 4° C. until assayed.

The internal standard, which was used for all extractions, contained 0.4 mg/ml monodecyl glycerol (GMC10) from Sigma-Aldrich in chloroform and was prepared and stored in a clean glass bottle which was sealed with a TEFLON lined screw cap. At the time of assay, methanol was mixed with the stock standard in the ratio of 2 parts chloroform to 1 part methanol giving a stock internal standard which was 0.267 mg/ml in GMC10.

The stock standard (1.8 mg/ml) was prepared by adding 18 mg of GML from Sigma-Aldrich to a tared 10 ml volumetric flask, recording the exact weight, filling it to the mark with the stock internal standard, and mixing it well. The solution was transferred to a clean glass vial, which was sealed with a TEFLON lined screw cap.

The working standard was diluted using volumetric pipettes, additional stock internal standard, and clean glass vials according to the following scheme.

| Standard level | Standard | Volume of Standard | Volume of Internal Standard | GML (mg/ml) |
|---|---|---|---|---|
| 1 | Stock | 5 | 5 | 0.9 |
| 2 | Standard 1 | 2 | 4 | 0.3 |
| 3 | Stock | 1 | 8 | 0.2 |
| 4 | Standard 3 | 3 | 3 | 0.1 |

The dilutions were stored in clean glass vials and sealed with TEFLON lined screw caps.

All test samples and matrices were allowed to reach room temperature before assay. They were mixed well by stirring with clean glass rods. Using graduated pipettes and clean glass vials which held 7-8 ml, the extractions were performed as follows: Triplicate 50 mg samples of each aged composition were added to tared vials and the exact weights recorded. (For samples that were emulsions with a larger droplet size, larger samples were needed to ensure a uniform sample. In those cases, a larger sample size was obtained and processed proportionately.) To these 5.0 ml of internal standard were added. The samples were mixed until they dissolved or were evenly dispersed and then 1.7 ml of 0.4 weight percent potassium chloride solution was added to each. The vials were capped, vortexed for 1 minute, and then centrifuged at top speed on a clinical centrifuge (IEC) until 2 clear phases resulted (3-5 minutes). The lower phase (organic) was separated from the upper phase (aqueous) by suction using a Pasteur Pipette, which had been inserted through the upper phase. It was transferred to a second vial containing a small amount (approximately 200 milligrams (mg)) of sodium sulfate in order to dry the sample. A portion was then transferred to an auto sampler for GC analysis.

Single extracts of each of the four standards were made in the same manner as the samples except that 50 mg of formulation matrix (formulated without GML, with the difference made up with another component (petrolatum or glycerin for Comparative Example D)) was added to each extraction vial followed by 5.0 ml of each of the working standards. An internal standard blank was also extracted as well as a sample matrix without any internal standard.

The order of analysis was: Internal Standard blank, standards (lowest to highest), solvent blank, samples (in random order), and calibration checks every 16 injections and at the end (level 2 standard). Each sample and standard was injected once.

The Gas Chromatography Conditions were:

| | |
|---|---|
| Instrument | HP 5890 or 6890 |
| Column | 15 meter ZB-5, 0.25 micon (µ) film 0.25 mm ID |
| Carrier | He, 22 pounds per square inch (psi) constant pressure (6890-constant flow 1 millilters per minute (ml/min)) |
| Injection | 2 microliter (µl) split 1:60, injector temp 350° C. |
| Liner | Restek SILTEK deactivated liner with SILTEK deactivated glass wool (Cat. No. 22406-213.5) |
| Program | 110° C. initial, 4° C./min to 210° C., 25° C./min to 350° C., hold 5 minutes (min) |
| Detector | FID at 350° C. |

The triplicate samples of each time point were prepared and analyzed once. The area ratio of GML/internal standard (GMC10) was converted into mg GML/sample using the standard curves, which was then divided by the sample weight (100 mg) and multiplied by 100 to obtain a weight percent of GML in the sample. The weight percent from each of the triplicate samples were then averaged and a standard deviation was obtained.

Good linearity was obtained with correlation coefficient, $R > 0.999$ over the range of analysis. Response factors for the standard calibration checks were less than or equal to 2.6 percent of that standard in the initial curve.

Emergence of Resistance Test

Overnight cultures of each of 30 MRSA isolates and 30 Methicillin Susceptible *Stapyloccus aureus* (MSSA) isolates were grown in Mueller-Hinton broth (MHB) at 35° C. in room air. Bacteria in the broth were concentrated by centrifugation for 15 minutes at 2,200 revloustions per minute (rpm). The spent broth was decanted and replaced with fresh MHB containing 0.5 µl, per mL of each of three antimicrobial compositions (Examples 31(IPA), 32(IPA), and 33(IPA)) or 0.125 µg/mL of mupirocin lithium salt (Sigma Aldrich, Milwaukee, Wis.). The cultures were returned to the incubator for 18 hours. Following incubation, each culture was again centrifuged and the bacterial pellet was divided into two aliquots. One aliquot was resuspended in MHB containing fresh antimicrobial compositions at twice the previous concentrations and returned to the incubator for continued exposure.

The second aliquot was screened for MRSA and MSSA by incubation with 2 mL of MHB containing 4 µg/mL of mupirocin or 1,200 µg/mL of Examples 31(IPA) or 32(IPA) or 33 (IPA). The resistance screens were incubated overnight at 35° C. in room air. After incubation, each screen was subcultured to fresh MHB and incubated for 4 to 6 hours. Minimum inhibitory concentration (MIC) testing was performed on logarithmically growing bacteria recovered from the screen. This procedure was repeated for 8 days. After 8 days of serial exposure, each bacterial pellet was resuspended in bland MHB and incubated overnight. The MIC of each antimicrobial composition or mupirocin was determined as the MIC90 (range) before and daily during serial passage.

Viscosity Test

In the following Examples (except where indicated) viscosity was measured at 23° C. at ambient pressure using a Brookfield LVDV-I+ viscometer equipped with a model D Brookfield heliopath and T spindles B-F. The spindle and speed was chosen for each particular sample such that the viscometer was operating in the middle of its range. All samples were allowed to equilibrate at 23° C. for 24 hours prior to measurement. Preferably the viscosity is taken at the lowest speed possible while staying within 20-80% of the viscometer range and more preferably between 30-70% of the range. In all cases the sample size and container geometry was chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles. The following table outlines preferred spindles for various sample viscosities.

| Sample Viscosity | T Spindle to Use |
|---|---|
| 1,000-100,000 | B |
| 1,000-200,000 | C |
| 5,000-500,000 | D |

| Sample Viscosity | T Spindle to Use |
|---|---|
| 10,000-1,250,000 | E |
| 500,000-3,000,000 | F |

The viscosity of each sample was taken as the highest relatively stable reading achieved on the first path the spindle traversed using the heliopath adapter.

EXAMPLES

Objects and advantages of this invention are further illustrated by the following examples, but the particular materials and amounts thereof recited in these examples, as well as other conditions and details, should not be construed to unduly limit this invention.

GLOSSARY of COMPONENTS

| Acronym | Trade Name | Description | Source/Address |
|---|---|---|---|
| GML | LAURICIDIN | Glycerol mono-laurate | MedChem Laboratories, Inc./Galena, IL |
| | PURAC HIPURE 88 | Lactic Acid (88%) | Purac America/Lincolnshire, IL |
| | | Mandelic Acid | Sigma-Aldrich/St. Louis, MO |
| | | Benzoic acid | Mallinckrodt Baker Inc./Paris, KY |
| | | Salicylic acid | Mallinckrodt Baker Inc. |
| | | $C_{10}H_{23}$ glycerin ether | (Preparation described in Example 18) |
| | | Propylene glycol monocaprate | Uniquema/Wilmington, DE |
| | CRODAPHOS SG | PPG-5 ceteth-10 phosphate | Croda Inc./Parsipanny, NJ |
| DOSS, 100% | COMPLEMIX | Dioctylsulfo-succinate, sodium salt (Docusate, sodium) | Cytec Industries/West Paterson, NJ |
| DOSS, 70% | AEROSOL GPG | Dioctylsulfo-succinate, sodium salt, 70% in ethanol/water | Cytec Industries |
| | POLYSTEP B12 | Sodium laureth-4 sulfate | Stepan Company/Northfield, IL |
| | MACKAM 50-SB | Lauramidopropyl-hydroxy sultaine | McIntyre Group Ltd./University Park, IL |
| | HOSTAPUR SAS 93G | Sodium C14-C17 Sec alkyl sulfonate, 93% solids | Clariant Corp./Charlotte, NC |
| | HOSTAPUR SAS 60 | Sodium C14-C17 Sec alkyl sulfonate, 60% solids | Clariant Corp |
| LMDO | AMMONYX LMDO | Lauramidopropyldi-methylamine oxide | Stepan Company |
| | HYDROLITE 5 | 1,2 pentane diol | Dragoco Inc./Totowa, NJ |
| PEG-400 | CARBOWAX 400 | Polyethylene glycol, MW = 400 | Union Carbide |
| DMI | ARLASOLVE DMI | dimethylisosorbide | Uniqema |
| | MAX LG650 | Glycerin initiated polypropylene glycol, equivalent wt = 89 | Lyondell Chemical Worldwide Inc./Houston, TX |
| | DOWANOL TPnB | Tripropyleneglycol | Sigma Aldrich |
| | | Glycerin USP | Mallinkrodt Baker Inc. |
| Pet | Snow White PET USP | White Petrolatum | Penreco |
| | | White beeswax | Acros |
| | PRISORINE 2021 | Isopropyl isostearate | Unichem |
| | FINSOLV TN | $C_{12}$-$C_{15}$ benzoate ester | Finetex |
| IPM | | Isopropyl myristate | Cognis Corp./Houston, TX |
| | CRODAMOL GTCC | Glycerol tricaprylate/caprate | Croda Inc. |
| | FILIPPOBENO Olive Oil | Olive oil, 100% Olive Oil | Imported by Salov North America Corp./Hackensack, NJ |
| | CETIOL OE | Dioctylether | Cognis Corp. |
| | | Mineral oil, USP | Paddock Laboratories Inc./Minneapolis, MN |
| BHA | | Butylated hydroxy-anisole | Eastman Chemical/Kingsport, TN |
| EDTA $(Na)_2$ | | Sodium salt of ethylene diamine tetra-acetic acid | W. R. Grace/Nashua, NH |
| | | Methyl paraben | Nipa/Wilmington, DE |
| | | Propyl paraben | Nipa/Wilmington, DE |
| | | Glycolic acid | Sigma-Aldrich |
| | PLURONIC P-65 | Poloxamer/block copolymer of propylene oxide and ethylene oxide | BASF Corp./Parsippany, NJ |
| | ARISTOFLEX HMB | Ammonium acryloyldimethltaurate/beheneth 25 meth-acrylate crosspolymer | Clariant Corp. |
| | SALCARE SC92 | Copolymer of acrylamide and trimethylaminoethyl-methacrylate chloride salt | Ciba Specialty Chemicals Corp./High Point, NC |
| | NATROSOL PLUS TYPE | Cetyl hydroxyethyl cellulose | Hercules, Aqualon Division/Wilmington, DE |

Examples 1-2 and Comparative Example A

Antimicrobial compositions were prepared using the components shown in Table 1a. White petrolatum was heated in a beaker to at least approximately 82° C. In another beaker, glycerin and DOSS were heated until the DOSS was dissolved and this solution was allowed to cool to approximately 82° C. Next, the contents of the first beaker were mixed with the contents of the second beaker with a mixing propeller. Mixing was continued until the mixture cooled to 71° C. at which point the GML was added and mixing continued as the mixture continued to cool. When the mixture had cooled to about 54° C., the lactic acid was added and mixing continued until the composition was about to congeal. Just before the composition congealed at approximately 43° C., the composition was removed from the mixer and poured into ointment jars.

TABLE 1a

| Example No. | GML | Lactic Acid (88%) | DOSS (100%) | Glycerin | White Petrolatum |
|---|---|---|---|---|---|
| 1 | 3.02 | 1.11 | 0.97 | 9.82 | 85.08 |
| 2 | 3.01 | 1.13 | 0.00 | 10.00 | 85.86 |
| Comparative A | 0.00 | 0.00 | 0.99 | 10.07 | 88.94 |

The compositions of Examples 1-2 and Comparative Example A were evaluated using the Antimicrobial Kill Rate Test and the results are shown in Table 1b.

TABLE 1b

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 1 | 3.02 | 3.84 | 6.47 | 3.59 | 5.25 | 5.29 |
| 2 | <3.02 | 3.02 | 3.14 | 2.88 | 3.54 | 3.16 |
| Comparative A | 2.15 | 2.50 | 2.73 | 2.42 | 2.42 | 2.82 |

The results indicate that the full formulation of Example 1 had good kill against both MRSA (Gram positive) and *E. coli* (Gram negative) organisms. The log reduction was in excess of 3.5 logs after 5 minutes and 5 logs after 10 minutes. Elimination of the surfactant from the formulation (Example 2) resulted in a significant reduction in antimicrobial efficacy. Elimination of the antimicrobial lipid and enhancer resulted in poor kill rate—less than 3 log reduction after 10 min (Comparative Example A).

Examples 3-7

Antimicrobial compositions were prepared as described in Examples 1-2 using the components shown in Table 2a. Mandelic acid was ground into a fine powder using a mortar and pestle and added to the glycerin and DOSS and heated to about 88° C. for Examples 3 and 4 or added directly to the hot, molten petrolatum at about 82° C. for Examples 5 and 6.

TABLE 2a

| Example No. | GML | Mandelic Acid | DOSS (100%) | Glycerin | White Petrolatum |
|---|---|---|---|---|---|
| 3 | 3.00 | 1.00 | 1.00 | 10.00 | 85.00 |
| 4 | 3.03 | 0.92 | 0.00 | 10.11 | 85.94 |
| 5 | 3.00 | 1.00 | 1.00 | 0.00 | 95.00 |
| 6 | 3.00 | 1.00 | 0.00 | 0.00 | 96.00 |
| 7 | 2.97 | 0.90 | 0.00 | 0.96 | 95.17 |

The compositions of Examples 3-7 were evaluated using the Antimicrobial Kill Rate Test and the results are shown in Table 2b and 2c.

TABLE 2b

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 3 | 3.6 | 5.7 | 5.9 | 4.0 | 5.6 | 6.1 |
| 4 | 2.8 | 3.9 | 4.3 | 5.7 | 5.6 | 6.0 |
| 5 | 5.0 | 5.8 | 5.4 | 5.4 | 5.8 | 6.3 |
| 6 | 2.4 | 2.6 | 3.6 | 3.2 | 3.3 | 3.7 |
| 7 | 2.3 | 3.1 | 4.1 | 4.0 | 3.9 | 4.7 |

TABLE 2c

| Example No. | *Pseudomonas ae.* (log reduction) | | |
|---|---|---|---|
| | After 2 minutes | After 5 minutes | After 10 minutes |
| 3 | 4.4 | 6.4 | 6.5 |
| 4 | 3.3 | 4.2 | 5.1 |
| 5 | 4.0 | 4.6 | 5.7 |
| 6 | 2.9 | 2.9 | 3.2 |
| 7 | 2.9 | 3.6 | 3.9 |

Example 3 contained a hydrophilic component (glycerin) and surfactant (DOSS) in addition to the antimicrobial lipid (GML) and enhancer (mandelic acid). This sample had the best antimicrobial activity overall, achieving greater than 5.9 log reduction against all three organisms at 10 minutes. Example 4 contained no surfactant (no DOSS), which led to a decrease in activity over Example 3. Example 5 which contained no hydrophilic component had decreased activity over Example 3 but the effect was not as great as elimination of the surfactant. Example 6 containing no hydrophilic component or surfactant showed relatively poor antimicrobial activity. Addition of only 1% hydrophilic component (Example 7) showed an improvement in antimicrobial activity.

Example 8

An antimicrobial composition was prepared using the components listed in Table 3a. GML, isopropyl isostearate, beeswax and FINSOLV TN were combined in a beaker, heated and stirred with a propeller mixer until a clear solution was obtained. Stirring was continued while cooling the solution to about 48° C. when the lactic acid was added. Stirring and cooling continued until the temperature was 43° C. when the composition was removed from the mixer and poured into the ointment jar.

TABLE 3a

| Example No. | GML | Lactic acid (88%) | White Beeswax | Isopropyl isostearate | FINSOLV TN |
|---|---|---|---|---|---|
| 8 | 10.00 | 1.00 | 20.00 | 29.00 | 40.00 |

The composition of Example 8 was evaluated using the Antimicrobial Kill Rate Test and the results are shown in Table 3b and 3c.

TABLE 3b

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 8 | >6.3 | >6.3 | >6.3 | 7.3 | 7.3 | 7.3 |

TABLE 3c

| Example No. | Pseudomonas ae. (log reduction) | | |
|---|---|---|---|
| | After 2 minutes | After 5 minutes | After 10 minutes |
| 8 | 8.0 | 8.0 | 8.0 |

The results indicated that the antimicrobial lipid plus enhancer in a non-petrolatum-based ointment had an exceptional kill rate of MRSA, E. coli, and Pseudomonas ae.

Examples 9-16

Antimicrobial Compositions were prepared as described in Examples 1-2 using the components shown in Table 4a. The surfactants were added like DOSS in Example 1.

TABLE 4a

| Example No. | Components (weight percent) | | | | | | |
|---|---|---|---|---|---|---|---|
| | GML | Lactic acid | Glycerin | Surfactant | | Component | |
| | | | | Type | Amt. | Type | Amt. |
| 9 | 3.00 | 1.00 | 10.00 | CRODAFOS SG | 2.00 | Pet | 84.00 |
| 10 | 3.00 | 1.00 | 10.00 | DOSS (100%) | 2.00 | Pet | 84.00 |
| 11 | 3.00 | 1.00 | 10.00 | POLYSTEP B12 | 2.00 | Pet | 84.00 |
| 12 | 3.00 | 1.00 | 10.00 | MACKAM 50-SB | 2.00 | Pet | 84.00 |
| 13 | 3.00 | 1.00 | 10.00 | HOSTAPUR SAS 93G | 2.00 | Pet | 84.00 |
| 14 | 3.00 | 1.00 | 10.00 | LMDO | 2.00 | Pet | 84.00 |
| 15 | 3.00 | 1.00 | 10.00 | DOSS (100%) | 2.00 | PEG | 84.00 |
| 16 | 3.00 | 1.00 | 10.00 | HOSTAPUR SAS 60 | 2.00 | Pet | 84.00 |

The compositions of Examples 9-16 were evaluated using the Antimicrobial Kill Rate Test and the results are shown in Table 4b.

TABLE 4b

| Example No. | MRSA (log reduction) | | | E. coli (log reduction) | | |
|---|---|---|---|---|---|---|
| | After 2 minutes | After 5 minutes | After 10 minutes | After 2 minutes | After 5 minutes | After 10 minutes |
| 9 | 6.41 | 6.17 | 6.41 | 5.29 | 5.56 | 2.65 |
| 10 | 3.33 | 3.38 | 6.17 | 5.85 | 5.54 | 6.14 |
| 11 | 5.74 | 6.41 | 5.88 | 3.49 | 4.34 | 6.11 |
| 12 | 4.18 | 5.05 | 5.90 | 2.63 | 2.80 | 4.47 |
| 13 | 5.73 | 6.11 | 6.11 | 6.03 | 6.23 | 6.23 |
| 14 | 3.45 | 5.16 | 5.78 | 2.69 | 3.40 | 4.05 |
| 15 | 6.11 | 6.11 | 6.11 | 6.23 | 6.23 | 6.23 |
| 16 | 5.73 | 5.02 | 6.22 | 6.07 | 6.17 | 6.17 |

The results indicated that Examples 9, 13, 15, and 16 had exceptional kill rates (>5 logs) after only 2 minutes against both MRSA and E. coli. The surfactants in these examples were anionic (sulfate, sulfonate, and phosphate). Example 11 also had very a good kill rate; however, the ethoxylation on this surfactant may have contributed to the lower efficacy shown against E. coli at the 2-minute and 5-minute time intervals. Example 10 contained DOSS, which had an exceptional kill rate (>6 logs) against both MRSA and E. coli after 10 minutes of exposure. Examples 12 and 14 contained zwitterionic and amine oxide surfactants, respectively, and the kill rate, while still good, was not as good as that of the anionic surfactants.

Example 17

The preparation of the $C_{10}H_{23}$ Glycerin Ether was a two step process.

First isopropylidene glycerol was prepared by adding 100 grams (g) glycerol, 400 ml acetone, 0.65 g p-toluenesulfonic acid, and 50 g of 3 A molecular sieves to a 1-liter NALGENE bottle with a cap. Rolling the bottle on a roller for 24 hours mixed the contents of the bottle. Next 0.95 g potassium carbonate ($K_2CO_3$) was added to the contents. The mixture was filtered, passed through an activated alumina column, concentrated on a rotary evaporator, and distilled using a water aspirator to pull a vacuum (boiling point (bp) approximately 100° C.). The final product was then used to prepare glycerol ether.

Second a 1-liter round-bottomed flask was purged with nitrogen and 500 ml xylene, 42 g isopropylidene glycerol, and 53.5 g potassium hydroxide (KOH) were added to the flask. The reaction flask was fitted with an overhead stirrer and a Dean-Stark trap. The contents were heated at reflux for approximately 15 hrs with azeotropic removal of $H_2O$. While continuing to heat at reflux, 61.4 g decyl bromide in 100 ml xylene was added dropwise to the reaction. After the addition was completed, the reaction was heated an additional 24 hrs at reflux. The contents were cooled, transferred to a separatory funnel, washed with deionized water 5 times using 100 ml of water each time, dried over magnesium sulfate ($MgSO_4$), filtered and concentrated on a rotarevaporator. The final product was distilled at reduced pressure (boiling point (bp) was approximately 136° C. at 0.5 millimeter (mm) Hg).

An antimicrobial composition was prepared using the components in Table 5a. The white petrolatum was heated to approximately 93° C. and the DOSS and the glyceryl ether were added to it while stirring using a mixing propeller. The mixture was stirred while being held at 93° C. until a clear solution was formed. The mixture was allowed to start cooling with continuous stirring. When the mixture reached approximately 65° C. the glycerin was added and the cooling and stirring continued. When the mixture reached approximately 49° C. the lactic acid was added and cooling and stirring continued until the composition was about to congeal (approximately 38° C.) and then it was poured into an ointment jar.

TABLE 5a

| Example No. | Components (weight percent) | | | | |
|---|---|---|---|---|---|
| | 88% Lactic Acid | $C_{10}H_{23}$ glycerin ether | 100% DOSS | Glycerin | White petrolatum |
| 17 | 1.13 | 1.46 | 1.02 | 10.07 | 88.94 |

The compositions of Example 17 were evaluated using the Antimicrobial Kill Rate Test and the results are shown in Table 5b.

TABLE 5b

| Example No. | MRSA (log reduction) | | | E. coli (log reduction) | | |
|---|---|---|---|---|---|---|
| | After 2 minutes | After 5 minutes | After 10 minutes | After 2 minutes | After 5 minutes | After 10 minutes |
| 17 | 3.16 | 3.70 | 4.51 | 4.68 | 5.88 | 5.47 |

The results indicated that over 3 log reductions after 2 minutes of exposure and over 4.5 log reductions after 10 minutes of exposure occurred for both MRSA and *E. coil* using an antimicrobial glycerin ether in combination with a enhancer (alpha-hydroxy acid).

Example 18

An antimicrobial composition was prepared using the components in Table 6a as described for Examples 1 and 2 but propylene glycol monocaprate was substituted for GML.

TABLE 6a

| | Components (weight percent) | | | | |
|---|---|---|---|---|---|
| Example No. | 88% Lactic Acid | Propylene glycol monocaprate | 100% DOSS | Glycerin | White petrolatum |
| 18 | 1.12 | 3.01 | 1.00 | 9.92 | 84.95 |

The compositions of Example 18 were evaluated using the Antimicrobial Kill Rate Test and the results are shown in Table 6b.

TABLE 6b

| | MRSA (log reduction) | | | *E. coli* (log reduction) | | |
|---|---|---|---|---|---|---|
| Example No. | After 2 minutes | After 5 minutes | After 10 minutes | After 2 minutes | After 5 minutes | After 10 minutes |
| 18 | 6.54 | 6.54 | 6.54 | 5.64 | 5.88 | 5.88 |

The results indicated that the antimicrobial composition containing propylene glycol monocaprate and an enhancer (lactic acid, an alpha-hydroxy acid) achieved an exceptional kill rate against MRSA (over 6 log reduction in 2 minutes) as well as an exceptional kill rate against *E. coli* (over 5.5 log reduction in 2 minutes).

Examples 19-24

Antimicrobial compositions were prepared as described for Examples 1-2 using the components in Table 7a. However, hydrophilic components were substituted for the glycerin.

TABLE 7a

| | Components (weight percent) | | | | | |
|---|---|---|---|---|---|---|
| Example No. | GML | 88% Lactic Acid | 100% DOSS | Hydrophilic component Type | Amt. | White petrolatum |
| 19 | 3.02 | 1.10 | 0.97 | HYDROLITE 5 | 9.64 | 85.28 |
| 20 | 3.00 | 1.13 | 1.00 | PEG 400 | 9.97 | 84.90 |
| 21 | 3.01 | 1.15 | 1.00 | DMI | 9.95 | 84.90 |
| 22 | 3.01 | 1.12 | 0.98 | NIAX LG650 | 9.85 | 85.04 |
| 23 | 3.00 | 1.13 | 1.00 | DOWANOL TPnB | 10.05 | 84.82 |
| 24 | 1.45 | 1.13 | 0.98 | Glycerin | 9.89 | 86.55 |

The compositions of Examples 19 and 21-24 were evaluated using the Antimicrobial Kill Rate Test and the results are shown in Table 7b.

TABLE 7b

| | MRSA (log reduction) | | | *E. coli* (log reduction) | | |
|---|---|---|---|---|---|---|
| Example No. | After 2 minutes | After 5 minutes | After 10 minutes | After 2 minutes | After 5 minutes | After 10 minutes |
| 19 | >4.78 | >4.78 | >4.78 | 4.65 | 4.65 | >4.65 |
| 21 | 3.10 | >4.78 | >4.78 | 2.07 | 3.67 | 4.42 |
| 22 | 3.1 | 4.18 | 4.69 | 2.07 | 3.67 | 4.42 |
| 23 | 4.78 | >4.78 | >4.78 | >4.65 | >4.65 | >4.65 |
| 24 | 4.04 | 5.57 | 5.49 | 3.87 | 3.67 | 5.79 |

The results indicated that good kill rates were achieved against both MRSA and *E. coli* (>4 log reduction at 10 minutes) with a wide variety of hydrophilic components. The best results appear to be in antimicrobial compositions containing small molecule glycols (Examples 19 and 24) as well as with the tripropyleneglycolmonobutyl ether (Example 23).

Examples 25-30

Antimicrobial compositions were prepared using the method described for Examples 1-2 and the components in Table 8a. The hydrophobic components were heated in a beaker to at least approximately 82° C. instead of the white petrolatum and the hydrophilic components were substituted for the glycerin. In Example 30 salicylic acid was substituted for lactic acid.

TABLE 8a

| | Components (weight percent) | | | | | | |
|---|---|---|---|---|---|---|---|
| Example No. | GML | 88% Lactic Acid | 100% DOSS | Hydrophilic Component Type | Amt. | Hydrophobic Component Type | Amt. |
| 25 | 3.01 | 1.11 | 0.99 | Glycerin | 9.89 | CRODAMOL GTCC | 84.99 |
| 26 | 3.01 | 1.11 | 0.97 | Glycerin | 9.69 | Olive Oil | 85.22 |
| 27 | 3.01 | 1.12 | 0.98 | Glycerin | 9.80 | CETIOL OE | 85.10 |
| 28 | 3.01 | 1.11 | 0.98 | DMI | 9.83 | CRODAMOL GTCC | 85.08 |
| 29 | 3.01 | 1.12 | 0.99 | Glycerin | 9.83 | Mineral oil | 85.06 |
| 30 | 3.00 | 0.25[1] | 1.00 | DMI | 9.97 | CRODAMOL GTCC | 85.77 |

[1] The enhancer used was salicylic acid.

The composition of Example 28 was evaluated using the Antimicrobial Kill Rate Test and the results are shown in Table 8b.

TABLE 8b

| Example No. | MRSA (log reduction) | | | E. coli (log reduction) | | |
|---|---|---|---|---|---|---|
| | After 2 minutes | After 5 minutes | After 10 minutes | After 2 minutes | After 5 minutes | After 10 minutes |
| 28 | 6.45 | >6.45 | >6.45 | 4.62 | 5.88 | >5.88 |

Example 28 had an exceptional kill rate against MRSA as well as *E. coli*. The use of the DMI improved the composition's stability over that of Example 25, which tended to split into distinct phases upon standing.

Examples 31-33 and 31(IPA)-33(IPA)

Antimicrobial Compositions were prepared using the components shown in Table 9a. White petrolatum and DOSS were placed in a beaker and heated until a solution was formed at about 104° C. While mixing with an overhead air mixer (Model No. 1AM-NCC-12, Gast, Benton Harbor, Mich.) glycerin and the acid (enhancer) were added. Next, the composition was cooled to 66° C. and the GML was added while holding the temperature between 60° C. and 66° C. When all of the components were in solution, it was cooled to about 46° C., removed from the mixer, and poured into an ointment jar.

TABLE 9a

| Example No. | Components (weight percent) | | | | | |
|---|---|---|---|---|---|---|
| | Enhancer | | | DOSS | | White |
| | GML | Type | Amt. | (100%) | Glycerin | Petrolatum |
| 31 | 3.00 | 88% Lactic Acid | 1.00 | 1.00 | 10.00 | 85.00 |
| 32 | 3.00 | Mandelic Acid | 1.00 | 1.00 | 10.00 | 84.99 |
| 33 | 3.00 | Benzoic Acid | 0.50 | 1.00 | 10.00 | 85.49 |

The compositions of Examples 31 and 33 were evaluated using the Antimicrobial Kill Rate Test and the results are shown in Table 9b.

TABLE 9b

| Example No. | MRSA (log reduction) | | | E. coli (log reduction) | | |
|---|---|---|---|---|---|---|
| | After 2 minutes | After 5 minutes | After 10 minutes | After 2 minutes | After 5 minutes | After 10 minutes |
| 31 | 2.70 | 3.16 | 5.53 | 1.11 | 1.41 | 3.41 |
| 33 | 4.59 | 4.54 | >4.62 | 5.25 | >5.32 | >5.32 |

Compositions 31-33 were instilled twice a day for two days in the nose of one of the inventors without any indication of irritation. No odor or taste was detected.

Isopropyl alcohol (IPA) was substituted for petrolatum and glycerin in the compositions from Examples 31 and 32. The amounts of each component are shown in Table 9c.

TABLE 9c

| Example No. | Components (weight percent) | | | | |
|---|---|---|---|---|---|
| | Enhancer | | | DOSS | Isopropyl |
| | GML | Type | Amt. | (100%) | alcohol |
| 31(IPA) | 3.00 | 88% Lactic Acid | 1.00 | 1.00 | 95.00 |
| 32(IPA) | 3.00 | Mandelic Acid | 1.00 | 1.00 | 95.00 |
| 33(IPA) | 3.00 | Benzoic Acid | 0.50 | 1.00 | 96.50 |

The compositions were prepared by mixng the ingredients until the components were fully dissolved.

The IPA modified antimicrobial compositions were tested using the Emergence of Resistance Test. The results are shown at baseline ($T_0$), after eight days ($T_8$) and the ratio of $T_0$ to $T_8$ in Table 9d.

TABLE 9d

| Example Number | MRSA | | | MSSA | | |
|---|---|---|---|---|---|---|
| | Initial ($T_0$) | Final ($T_8$) | $T_0/T_8$ | Initial ($T_0$) | Final ($T_8$) | $T_0/T_8$ |
| Mupirocin | 0.25 | 64 | 256 | 0.25 | 128 | 512 |
| 31(IPA) | 60 | 240 | 4 | 60 | 60 | 1 |
| 32(IPA) | 120 | 60 | 0.5 | 60 | 60 | 1 |
| 33(IPA) | 60 | 60 | 1 | 60 | 60 | 1 |

The results indicate that the MIC to mupirocin increased dramatically while the MIC of the compositions of the present invention increased less than 4 fold and some did not increase at all. This shows that there was significant resistance was generated to mupirocin but not to the compositions of the present invention.

In-vivo efficacy was demonstrated against a clinical isolate of MRSA using a murine model based on K, Cante-Kiser J, Lee J. Development and characterization of *Staphylococcus aureus* nasal colonization model in mice. 1999 Infect and Immunity 67(10) 5001-5006. Prior to evaluation of the active compositions the lowest number of *S. aureus* required to establish nasal colonization in 70% of mice detectable 5 days after challenge and persisting at least 10 days after challenge was determined. This was using an innoculum of $10^8$ cfu/nare. Mice (239 described as 25 g to 30 g Hsd:ICR) were challenged intranasally with $10^8$ MRSA #561(a clinical isolate of methicillin resistant *staphylococcus* obtained from Mayo Clinic, Rochester, Minn.) and arbitrarily assigned to one of five treatment regimens: mupirocin ointment, bland ointment, antimicrobial compositions of Examples 31, 32, and 33. The bland ointment consisted of petrolatum (89%), glycerin (10%) and DOSS (1%). Mice received either no treatment (none) or treatment with 10 μL per nare of warmed (42° C.) ointment (one of five) to each nare, three times daily for two days Three days after treatment, both anterior nares were swabbed and cultured for MRSA. Colonies appearing to be *S. aureus* were confirmed with a latex agglutination test. *S. aureus* was detected in 160 colonization cultures from 239 mice challenged. These mice continued to be studied. The results of the treatments are listed in Table 9e as the number of animals with no MRSA detected after treatment (successful), the percent of the animals treated successfully, the number of animals with MRSA (failure), and the percent of animals whose treatment failed.

TABLE 9e

| Example Number | Number of Mice without MRSA | Percent Treated Successfully | Number of Mice with MRSA | Percent Whose Treatment Failed |
|---|---|---|---|---|
| None | 1 | 10 | 9 | 90 |
| Bland Ointment | 12 | 32 | 26 | 68 |
| Mupirocin | 19 | 50 | 19 | 50 |
| 31 | 18 | 46 | 21 | 54 |
| 32 | 24 | 71 | 10 | 29 |
| 33 | 33 | 89 | 7 | 17 |

The results of MRSA nasal decolonization indicated that the antimicrobial composition of Example 33 was more active than mupirocin and that the antimicrobial compositions of Examples 31 and 32 were as active as mupirocin as measured by eradication of MRSA from the anterior nasopharynx.

Using the Fisher's exact test. Results of treatment with mupirocin, Ex 31, Ex. 32 and Ex. 33 were significantly ($P<0.05$) different than was no treatment. Treatment with Ex. 33 or Ex. 32 was significantly ($P<0.05$) more active than treatment with bland ointment. Treatment with Ex. 33 was significantly ($P<0.002$) more active than mupirocin. Treatment with Ex. 31 ($P=0.46$) was not significantly different than treatment with mupirocin. Treatment with Ex. 32 showed a trend toward being more effective than treatment with mupirocin ($P=0.06$).

Example 34

Example 34 was prepared using the components given in Table 10a. White petrolatum and GML were heated in a beaker to at least approximately 93° C. In another beaker, glycerin, DOSS, and lactic acid were heated until the DOSS was dissolved at approximately 143° C. This solution was mixed with a mixing propeller and allowed to cool to approximately 59° C. Next, the contents of the second beaker were mixed with the contents of the first beaker with a mixing propeller. Mixing and cooling continued until the composition was about to congeal at approximately 46° C.

Just before the composition congealed it was removed from the mixer and poured into ointment jars.

TABLE 10a

| | Components (weight percent) | | | | |
|---|---|---|---|---|---|
| Example No. | GML | 88% Lactic Acid | DOSS (100%) | Glycerin | White Petrolatum |
| 34 | 3.00 | 1.00 | 1.00 | 10.00 | 85.00 |

The composition appeared very similar to that of Example 31 using this alternative process.

Examples 35-37

Antimicrobial Compositions were prepared using the components shown in Table 11a. PEG 400 and PEG 1450 were melted together in one beaker at about 82° C. In a second beaker, the glycerin was heated to about 60° C. and the GML was dissolved in the heated glycerin. The enhancers and surfactants were added to the first beaker of melted PEGs and mixed with a propeller mixer while keeping the temperature at about 82° C. After the surfactants and enhancers were dissolved in the PEG component, the solution was mixed and cooled to about 63° C. Then the contents of the second beaker, glycerin and GML were added with constant mixing. The compositions were cooled with continual mixing to just above the congealing point (about 38° C.) and poured into ointment jars.

DRAWING TABLE 11a

| | | Components (weight percent) | | | | | | |
|---|---|---|---|---|---|---|---|---|
| Ex. | | Enhancer | | | Surfactant | | | |
| No. | GML | Type | Amt. | Glycerin | Type | Amt. | PEG 400 | PEG 1450 |
| 35 | 3.00 | 88% Lactic Acid | 1.00 | 20.00 | DOSS USP (50%) | 2.00 | 59.00 | 15.00 |
| 36 | 3.00 | Mandelic Acid | 1.00 | 10.00 | Pluronic P65 | 5.00 | 60.00 | 21.00 |
| 37 | 3.00 | Mandelic Acid | 1.00 | 20.00 | DOSS USP (50%) | 2.00 | 59.00 | 15.00 |

The compositions of Examples 35-37 were evaluated using the Antimicrobial Kill Rate Test and the results are shown in Table 11b.

TABLE 11b

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 35 | >5.11 | >5.11 | >5.11 | 5.20 | 5.25 | >5.36 |
| 36 | >6.14 | >6.14 | >6.14 | >6.57 | >6.57 | >6.57 |
| 37 | >6.14 | >6.14 | >6.14 | 6.29 | 6.39 | 6.48 |

The antimicrobial kill rate of these compositions was excellent against all three organisms indicating broad spectrum kill. The antimicrobial kill rate was greater than 5 log reduction at 2, 5, and 10 minutes.

Examples 38-41

Antimicrobial Compositions were prepared using the components shown in Table 12a. The white petrolatum was melted in a beaker on a hot plate with gentle stirring with a propeller mixer while heating from about 88° C. to 93° C. In a second beaker the enhancers were dissolved or suspended in the glycerin at about 77° C. The DOSS was added to the hot petrolatum (88° C. to 93° C.) in the first beaker and mixed until a clear solution was obtained. The contents of the second beaker (glycerin-enhancer mixture) were added to the first beaker and the composition cooled with constant stirring. When the composition had cooled to about 71° C. the GML was added with constant stirring. The compositions were cooled with continual mixing to just above the congealing point (about 43° C.) and poured into ointment jars.

TABLE 12a

| | Components (weight percent) | | | | |
|---|---|---|---|---|---|
| Example | Enhancer | | | DOSS | White Petrolatum |
| No. | GML | Type | Amt. | Glycerin | (100%) | USP |
| 38 | 3.00 | Salicylic Acid | 0.20 | 10.00 | 1.00 | 85.80 |
| 39 | 3.00 | BHA<br>EDTA (Na)$_2$ | 0.10<br>0.10 | 10.00 | 1.00 | 85.80 |
| 40 | 3.00 | BHA<br>EDTA (Na)$_2$<br>Methyl paraben<br>Propyl paraben | 0.10<br>0.10<br>0.10<br>0.01 | 10.00 | 0.00 | 86.69 |
| 41 | 3.00 | Benzoic acid | 0.50 | 10.00 | 1.00 | 85.50 |

The compositions of Examples 38-41 were evaluated using the Antimicrobial Kill Rate Test and the results are shown in Table 12b and 12c.

TABLE 12b

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 38 | 3.50 | 6.26 | 6.88 | 3.20 | 6.74 | 6.74 |
| 39 | 3.55 | 4.13 | 6.45 | 3.20 | 3.98 | 4.13 |
| 40 | 3.33 | 4.79 | 5.84 | 4.66 | 6.33 | 6.74 |
| 41 | 4.49 | 4.54 | 4.62 | 5.25 | 5.32 | 5.32 |

TABLE 12c

| Example | Pseudomonas ae. (log reduction) | | |
|---|---|---|---|
| No. | After 2 minutes | After 5 minutes | After 10 minutes |
| 38 | 6.54 | 6.54 | 6.54 |
| 39 | 3.35 | 6.05 | 6.20 |
| 40 | 3.39 | 6.08 | 6.20 |
| 41 | 5.89 | 6.41 | 6.37 |

The results indicated that at least a 4 log reduction kill rate at 5 minutes was achieved using the compositions of Examples 38-41. This indicated a rapid broad spectrum activity.

Examples 42-43, Comparative Examples B-E, Examples 31-32, and Examples 38-49 Aging Study Using Gas Chromatography Aging studies were done for some of the antimicrobial compositions. Gas chromatography (GC) was used to determine what components were being lost and what components might be used to prevent that loss.

Additional antimicrobial compositions with different enhancers and without enhancers were prepared as described for Examples 38-41 using the components in Table 13a.

TABLE 13a

| | Components (weight percent) | | | | | |
|---|---|---|---|---|---|---|
| Example | | Enhancer | | DOSS | | White |
| No. | GML | Type | Amt | (100%) | Glycerin | Petrolatum |
| 42 | 3.00 | Benzoic Acid | 0.20 | 1.00 | 10.00 | 85.80 |
| 43 | 3.00 | Glycolic Acid | 1.00 | 1.00 | 10.00 | 85.00 |
| Comparative B | 3.00 | None | 0.00 | 0.00 | 0.00 | 97.00 |
| Comparative C | 3.00 | None | 0.00 | 0.00 | 10.00 | 87.00 |
| Comparative D | 3.00 | None | 0.00 | 1.00 | 10.00 | 86.00 |
| Comparative E | 30.00 | None | 0.00 | 0.00 | 70.00 | 0.00 |

The compositions of Examples 31-32, 38-40, and 42-43, and Comparative Examples B-E were evaluated using the Aging Study with GC as described in the Test Protocols and the results are shown in Table 13b, 13c, 13d and 13e.

Example 31 contains lactic acid and Example 32 contains mandelic acid. The results in Table 13b and Table 13c indicate the difference in aging of the two compositions at 23° C. for 9 months and at 40° C. for 4 weeks.

TABLE 13b

| | GML in grams remaining after aging at 40° C. for: (weeks) | | | | |
|---|---|---|---|---|---|
| Example No. | Initial | 2 | 3 | 4 | Percent retention after 4 weeks |
| 31 | 3.06 | 2.90 | 2.97 | 2.96 | 97 |
| 32 | 3.04 | 2.78 | 2.82 | 2.80 | 92 |

TABLE 13c

| | GML in grams remaining after aging at 23° C. for (months) | | | |
|---|---|---|---|---|
| Example No. | Initial | 5 | 9 | Percent retention after 9 months |
| 31 | 3.06 | 3.01 | 3.09 | 103 |
| 32 | 3.04 | 2.99 | 3.01 | 100 |

The results in Table 13d indicate the quantitative results of GML loss after aging at the indicated temperatures for 7 days. The compositions that were incubated at 65° C. were in the liquid state so they were phase split and incubated with and without shaking to see if agitation itself contributed further to the GML loss.

TABLE 13d

| | GML in grams remaining after aging 7 days at: | | | | |
|---|---|---|---|---|---|
| Example No. | 10° C. static | 23° C. static | 40° C. static | 65° C. static | 65° shaken |
| Comparative B | 3.03 ± 0.04 | 2.96 ± 0.01 | 3.04 ± 0.03 | 2.94 ± 0.05 | 2.97 ± 0.02 |
| Comparative C | 3.05 ± 0.05 | 3.03 ± 0.02 | 3.14 ± 0.03 | 3.22 ± 0.12 | 3.20 ± 0.04 |
| Comparative D | 3.00 ± 0.10 | 3.05 ± 0.04 | 3.14 ± 0.03 | 3.12 ± 0.19 | 3.20 ± 0.02 |
| 31 | 3.21 ± 0.05 | 3.08 ± 0.01 | 3.02 ± 0.01 | 2.73 ± 0.01 | 2.70 ± 0.01 |
| 32 | 3.17 ± 0.02 | 3.03 ± 0.02 | 2.91 ± 0.03 | 2.39 ± 0.01 | 2.54 ± 0.05 |
| Comparative E | Not done | Not done | 30.33 ± 0.13 | 29.38 ± 0.23 | 29.98 ± 0.12 |

The results in Table 13e indicate the quantitative results of GML loss after aging at the 40° C. for 28 days. The compositions contain a variety of enhancers: lactic acid (Example 31), salicylic acid (Example 38), BHA and EDTA (Example 39), methyl and propyl paraben (Example 40), benzoic acid (Example 42), and glycolic acid (Example 43).

TABLE 13e

| Example No. | GML in grams remaining after 4 weeks at: | | |
|---|---|---|---|
| | Initial | 40° C. | Percent retention |
| 31 | 3.03 ± 0.01 | 2.85 ± 0.02 | 94 |
| 38 | 2.85 ± 0.07 | 2.64 ± 0.07 | 93 |
| 39 | 2.97 ± 0.02 | 3.00 ± 0.02 | 101 |
| 40 | 3.03 ± 0.01 | 2.85 ± 0.02 | 94 |
| 42 | 3.11 ± 0.01 | 2.91 ± 0.01 | 94 |
| 43 | 2.94 ± 0.01 | 2.70 ± 0.01 | 92 |

The examples in Table 13e may all have acceptable aging in that after 4 weeks at 40° C. they had >90% retention of GML. Examples 39, 31, 40, and 42, showed the best aging.

Subject Acceptability First Panel Evaluation

A panel of 10 normal healthy volunteers of either gender over 18 years of age evaluated a component composition without active antimicrobial lipid to determine acceptability and to develop evaluation methodology for future evaluations.

The compositions evaluated are shown in Table 14.

TABLE 14

| | Components (weight percent) | | | | | |
|---|---|---|---|---|---|---|
| Composition | Lactic Acid USP | Glycerin USP | Docuate sodium USP (50%) | White petrolatum USP | PEG 400 NF | PEG 3350 NF |
| W | 1.00 | 10.00 | 2.00 | 87.00 | 0.00 | 0.00 |
| X | 1.00 | 20.00 | 2.00 | 0.00 | 59.00 | 18.00 |

Test Procedure

A dose was 0.5 ml of Composition W or X applied using a preloaded 1 cm$^{-3}$ plastic syringe. The volunteers applied the first dose after viewing a demonstration of the technique. The volunteers applied a second and third dose during Day 1.

One-half of the volunteers (5) were dosed with Composition W and one-half of the volunteers were dosed with Composition X on Day 1 and given a Rhinoscopic Examination of Nares before and after application on Day 1 and after 24 hours on Day 2. On Day 8 those volunteers dosed with Composition W on Day 1 received Composition X and those dosed with Composition X on Day received Composition W. They were given a Rhinoscopic Examination of Nares before and after application on Day 8 and after 24 hours on Day 9.

Volunteers completed a questionnaire on Day 1 and on Day 9.

Results:

All 10 volunteers successfully completed both periods of the study. Descriptive analysis was provided for each categorical variable in the study.

Composition W was preferred by 10/10 of the volunteers. Five of ten volunteers could not complete all three application of Composition X. They cited stinging, burning and runny noses as primary reasons. Composition X caused more rhinorrhea than Composition W. Volunteers using Composition X felt they could use the ointment for a shorter period of time than with Composition W. Composition W could be felt to remain in the nasal vestibule longer (mean 218 minutes) than Composition X (mean 145 minutes).

Subject Acceptability Second Panel Evaluation

A second panel evaluation was done to determine acceptability of essentially anhydrous ointments based hydrophobic vehicles containing lactic acid or mandelic acid. The criteria for the panel were the same as for the first panel. The compositions evaluated are given in Table 15.

TABLE 15

| | Components (weight percent) | | | | |
|---|---|---|---|---|---|
| Composition | Lactic Acid USP | Mandelic Acid | DOSS USP (50%) | Glycerin USP | White petrolatum USP |
| Y | 1.00 | 0.00 | 2.00 | 10.00 | 87.00 |
| Z | 0.00 | 1.00 | 2.00 | 10.00 | 87.00 |

The test procedure was the same as that used for the first panel except a cotton swab was used to apply the composition rather than a tube.

Results:

Both ointments were acceptable with minimal, if any, side effects. The preference for the two ointments was fairly equally divided. Four of ten volunteers expressed a slight preference for the mandelic acid composition, three of ten volunteers expressed a slight preference for the lactic acid composition, and three of ten volunteers noticed no difference between the compositions.

Each volunteer applied 0.5 ml of composition; however, approximately 0.1 gram was routinely left on the swab. Therefore the dose was about 0.2 ml per nare. The time that the ointments remained in the volunteers' noses varied between volunteers, but there were indications that the ointment remained in place up to 24 hours. Two volunteers reported that the ointment appeared to accumulate from application to application.

The feel of the ointment in the nose and smell were the most noticed characteristics of both ointments, but the characteristics were all in the acceptable range.

Examples 44-47

Aqueous antimicrobial compositions were prepared using the components listed in Table 16a. Water or glycerin (Example 44), GML, mandelic acid, and PLURONIC P-65 were mixed and heated together to 70° C. The mixture was sheared on a Silverson Homogenizer for 1 minute to emulsify the components. A polymer was added to the warm solution for Examples 45-47. The composition was shaken, sealed in glass jars, and the jars were placed on a roller to mix and cool.

TABLE 16a

| | | | Components (weight percent) | | | |
|---|---|---|---|---|---|---|
| Ex. No. | GML | Mandelic acid | 70% DOSS | Polymer Type | Amt. | POLOXAMER | Water or glycerin[1] |
| 44 | 3.00 | 1.00 | 1.43 | None | 0.00 | 0.00 | 94.57[1] |
| 45 | 1.00 | 1.00 | 2.86 | ARISTOFLEX HMB | 1.50 | 10.00 | 83.64 |
| 46 | 0.94 | 0.94 | 2.70 | SALCARE SC92 | 8.50 | 9.43 | 77.49 |
| 47 | 1.00 | 1.00 | 2.83 | NATROSOL Plus Type | 2.08 | 9.89 | 83.24 |

[1]Example 44 contains glycerin not water

The pH of Examples 44-47 was determined using a pH meter (Denver Instrument, Model 225 from VWR Scientific) and a gel filled, epoxy, combination pH probe (VWR Scientific) and the results are shown in Table 16b. The Brookfield viscosity was determined as described above using the Helipath spindles and speed of rotation in rotations per minute (rpm) indicated with the results shown in Table 16b.

TABLE 16b

| Example No. | pH | Viscosity (cps) | Helipath spindle | Speed (rpm) |
|---|---|---|---|---|
| 44 | ND[1] | 46000 | E | 1.5 |
| 45 | 2.3 | 66000 | D | 1.0 |
| 46 | 2.7 | >1.35 Million | F | 0.5 |
| 47 | 2.6 | 2000 | B | 12.0 |

[1]ND means not done.

The compositions of Examples 44-47 were evaluated using the Antimicrobial Kill Rate Test and the results are shown in Table 16c and 16d.

TABLE 16c

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 44 | >6.17 | >6.17 | >6.17 | >5.93 | >5.93 | >5.93 |
| 45 | >6.17 | >6.17 | >6.17 | >5.93 | >5.93 | >5.93 |
| 46 | >5.94 | >5.94 | >5.94 | 5.83 | >6.10 | 5.87 |
| 47 | >6.17 | >6.17 | >6.17 | 5.88 | >5.93 | >5.93 |

TABLE 16d

| Example No. | Pseudomonas ae. (log reduction) | | |
|---|---|---|---|
| | After 2 minutes | After 5 minutes | After 10 minutes |
| 44 | >6.06 | >6.06 | >6.06 |
| 45 | 4.86 | 6.55 | 6.31 |
| 46 | >6.01 | >6.01 | >6.01 |
| 47 | 5.98 | >6.06 | >6.06 |

The antimicrobial kill rate of these compositions was excellent against all three organisms indicating broad spectrum kill. The antimicrobial kill rate was greater than 4 log reduction at 2 minutes and greater than a 5 log reduction at 5 and 10 minutes for all three bacteria. In fact, for many time points complete kill was achieved (as indicated by a ">" sign).

Examples 48-76

Additional antimicrobial compositions were prepared using the components shown in Table 17, plus 0.5% weight by weight (w/w) benzoic acid and the remaining percentage w/w amount petrolatum. The petrolatum, glycerin, and DOSS were heated in an oven to 77° C. until completely melted. They were then removed from the heat and mixed using a Silverson lab homogenizer for 60 seconds at 75% speed. After the contents cooled to 60° C. the benzoic acid was added and this was sheared with the Silverson homogenizer for 60 seconds at 75% speed Immediately thereafter the glycerol monolaurate (Lauricidin) was added and homogenized for 60 seconds at 75% speed. Mixing the composition was continued using an overhead propeller mixer until it was cool. The contents were sealed in a glass mixing jar. Each sample was tested for antimicrobial activity in duplicate according to the Antimicrobial Filter Assay Test against both MRSA and MSSA (one strain each).

The samples made were set up as a Central Composite Design of Experiments (DOE). Initially the components were varied over the following ranges: Glycerin 5-25 wt-%; DOSS 0.5-2 wt-%; and GML 2-6 wt-%.

Additional compositions were added to this original design and these are included in Table 17. Samples were made in run order as indicated in Table 17.

The results of the DOE were analyzed using Design Expert 6.0.3 (Stat-Ease Inc., Minneapolis, Minn.). Analysis of the reduced model using variance indicates that for killing MSSA a linear model having the concentration of glycerin and DOSS as significant variables is an excellent fit having a "p value" of less than 0.0003. The final equations are shown below:

Final Equation in Terms of Coded Factors:

MSSA Filter Assay Kill=+2.76+0.66*A(glycerin)+
1.76*B(DOSS)+0.51*C(GML)

Final Equation in Terms of Actual Factors:

MSSA Filter Assay Kill=−2.188+0.0663*Glycerin+
2.353*DOSS+0.254*GML

Analysis of the reduced model using variance indicates that for killing MRSA a linear model having the concentration of glycerin and DOSS as significant variables is an excellent fit having a "p value" of less than 0.0001. The final equations are shown below:

Final Equation in Terms of Coded Factors:

MRSA Filter Assay Kill=+3.32+1.37*A(glcyerin)+
1.58*B(DOSS)−0.10*C(GML)

Final Equation in Terms of Actual Factors:

MRSA Filter Assay Kill=−1.16+0.137*Glycerin+
2.106*DOSS−0.052330*GML

The equations and statistical results indicate that increasing the concentration of hydrophilic component (glycerin) and the surfactant (DOSS) improve the antimicrobial efficacy in compositions comprising a hydrophobic vehicle.

Antimicrobial Filter Assay Efficacy Test

This method tries to mimic the actual use conditions for many topical antiseptics. In most cases a topical antiseptic is applied to the area and allowed to remain in contact and kill any microorganisms present in an essentially static state. In this assay, a composition was spread onto a film to form a uniform coating 10-mil (250-μm) thick. A membrane filter with bacteria on the surface was directly contacted onto the surface of the composition. After a defined period of time (usually 2 hours), the inoculated disk was placed in a neutralizing broth, and at least a portion of this was diluted and plated to enumerate the surviving bacteria. For less viscous compositions, a compatible thickening agent should be incorporated to achieve a viscosity of at least 20,000 cps and preferably at least 50,000 cps.

The Neutralizing Solution (NS) preparation was a modification of the Standard Sampling Solution (P. Williamson et al., "A New Method for the Quantitative Investigation of Cutaneous Bacteria," *J. Invest. Derm.*, 45, 498-503 (1965)). The following components in the listed amounts were combined and heated on high with stirring until lecithin was completely dissolved and the solution became white. The solution was then allowed to cool, the pH adjusted to 7.9±0.1 (when required), and then autoclaved for 20 minutes. The solution was swirled immediately after sterilization.

| | |
|---|---|
| 0.04% monobasic potassium phosphate ($KH_2PO_4$) | 0.4 g |
| 1.01% dibasic sodium phosphate ($Na_2HPO_4$) | 10.1 g |
| 0.1% Triton X-100 | 1.0 g |
| 0.3% Lecithin | 3.0 g |
| 3.0% Tween 80. | 30.0 g |
| $dH_2O$ | to 1 L |

The phosphate buffered water (PBW) was prepared according to Butterfield's Phosphate Buffer, *Journal of the Association of Official Analytical Chemists*, 22, 625 (1939). Briefly, a 0.25M stock solution was prepared by dissolving 34 grams potassium dihydrogen phosphate in 500 mL deionized water. The pH was adjusted to 7.2 with 10N sodium hydroxide and the volume diluted to exactly 1 liter. This was filter sterilized and dispensed into sterile bottles that were stored at 4° C. until use. The working solution of PBW was prepared by adding 1.25 mL stock solution to 1 liter deionized water and autoclaved for 20 minutes.

An initial experiment was conducted to confirm that the Neutralizing Solution (NS) was effective at neutralizing the antiseptic while not damaging the microorganisms. In general, to confirm neutralization, 100 μL (approximately $10^4$ CFU/mL) of inoculum (target final organism concentration of 10-100 CFU/mL) was added to warmed (35° C.±2° C.) 20 mL Neutralizing Solution and vortexed (Toxicity Control). In addition, a 23-mm sample disk with ointment was dropped into the NS and the tube vortexed vigorously (Test Sample). Duplicate samples of one (1) mL aliquots were pour plated at two time points: (1) immediately (<1 minute) in tryptic soy agar (TSA), and (2) after 1 hour at ambient temperature. Plates were incubated at 35° C.±2° C. for up to 48 hours. Colonies were counted and CFU/mL calculated. The data was converted to $\log_{10}$ CFU/mL.

The Numbers Control consisted of 100 μL of inoculum added to 20 mL PBW (phosphate buffered water) to yield an organism concentration of 10-100 CFU/mL.

Neutralizer Effectiveness: If the $\log_{10}$ CFU/mL of the test sample was not more than 0.3 log less than the $\log_{10}$ CFU/mL of the corresponding Numbers Control, the neutralization was considered effective.

Neutralizer Toxicity: If the Toxicity Control (TC) was not more than 0.3 log less than the $\log_{10}$ CFU/mL of the corresponding Numbers Control sample, the neutralizing solution was considered non-toxic.

Test Organisms and Inoculum Preparation

The test organisms for this assay were methicillin resistant *Staphylococcus aureus* (MRSA), ATCC 33953 and *Staphylococcus aureus* (MSSA), ATCC 27217. The initial suspension was prepared by suspending bacterial colonies from overnight growth plates in phosphate-buffered water (PBW). A 0.5 McFarland turbidity standard was used to obtain a cell density of approximately $1.5 \times 10^8$ CFU/mL.

Initial and final counts were taken of the inoculum suspenstion were taken at the beginning and end of the test period to confirm these were within 1.0 log/ml for a valid test.

Test Materials

Examples were spread at room temperature to a uniform thickness of 0.010 inch (250 μm) using a laboratory hand held knife coater (slotted knife) onto a 100 μm thick biaxially oriented clean and 70% v/v isopropyl alcohol (IPA) disinfected polyesterterephthalate (PET) film. These coated samples were placed in sterile Petri dishes and sealed with Parafilm to prevent evaporation and preserve cleanliness. Bubbles in the formulation were minimized as much as possible. Test samples were then cut from the PET coated films using a 70% v/v isopropyl alcohol (IPA) disinfected 23 mm die. The sample disks were stored in sterile Petri dishes on thin layers of sterile gauze or other similar support until testing. The disks were warmed to 36° C. prior to testing antimicrobial activity.

Measurement of Antimicrobial Activity:

Using aseptic technique, a 0.22 μm filter (Millipore (Billerica, Mass.) white GSWP, 25 mm (nitrocellulose cat. No GSWP02500) was inserted into a glass filter holder with fritted glass support. The filter holder was placed over an Erlenmeyer filter flask, which was connected to a vacuum pump. While a vacuum was pulled, 2 mL of the inoculum were slowly dropped onto the filter and rinsed slowly with approximately 5 mL of PBW, resulting in approximately 8 logs bacteria ($10^8$) on the surface of the filter.

After the vacuum was released, the filter was removed from the filter holder with a 70% IPA-disinfected forceps and placed bacteria-side down on top of a warmed ointment disk. The filter was gently pressed in place with the forceps. Approximately 1 mL of sterile water was added to the Petri dish to prevent desiccation. The samples were incubated for 2 hours at 35° C.±2° C. All samples were tested in duplicate.

Control samples were prepared to enumerate the level of bacteria captured on the filters. The filters containing bacteria were placed over disinfected PET film disks (no ointment). All other procedures were the same as the test samples.

At the end of the exposure time (time bacteria are in contact with the composition) the inoculated disk was dropped into 20 mL warm (35° C.±2° C.) NS. The tubes were shaken by hand until the filter separated from the ointment, then vortexed vigorously for 2 minutes to suspend any surviving bacteria on a VWR Scientific Vortex Genie 2. Serial dilutions were prepared in PBW and plated in duplicate with TSA. Plates were incubated at 35° C.±2° C. for up to 48 hours.

Colonies were counted and raw data was recorded. Duplicate plates were averaged and multiplied by the dilution factor to arrive at CFU/mL. The average CFU/sample was calculated by multiplication of CFU/mL by the total volume (20 mL) and then converted to $\log_{10}$ CFU/mL. Counts of less than 1 CFU/sample were treated as 1 CFU/sample such that the log transformation was zero. Log reductions were calculated by subtracting the $\log_{10}$ bacterial recovery of the test materials from the averaged $\log_{10}$ bacterial recovery of the control.

The compositions of the present invention were analyzed for their ability to kill MRSA at 2 hours. The data is shown in Table 17.

Preferred compositions achieved, after 2 hours of contact with the MRSA laddened filter paper, at least 1.5 log reduction, more preferably at least a 2 log reduction, and most preferably at least a 3 log reduction. Particularly preferred compositions of the present invention achieved at least a 4 log reduction after 2 hours of contact. Most preferred formulations achieved these log reduction values for both test organisms (MRSA and MSSA).

The results shown in Table 17 indicate that as both the hydrophilic component (glycerin) and the surfactant (DOSS) increase in concentration so does the antimicrobial efficacy, when the antimicrobial composition is formulated in a hydrophobic vehicle.

Killing Microbes on Tissue

Many of the compositions of the present invention are intended to kill microorganisms on mammalian tissue such as skin and mucosal tissue. The extent of kill can be determined in the following manner. Subjects are identified who are naturally colonized with the microorganism of interest. This is preferred over methods where the tissue is artificially colonized with non-resident flora. For example, subjects may be identified who are colonized with *Staphylococcus aureus* (SA) in the anterior nares by swabbing the anterior nares and culturing the swab. This is normally repeated at least one additional time to ensure the subject is a "chronic carrier," i.e., one who carries the organism all or most of the time. A swab may also be taken several days prior to treatment to increase the probability that the subject is, in fact, a carrier. The subject is then treated with the indicated composition in a dose and at a frequency stated. The anterior nares once again are swabbed to determine if the bacteria has been reduced or eradicated (decolonized). Preferred formulations eradicate the SA in less than 72 hours, more preferably in less than 48 hours, and most

TABLE 17

| Ex. # | Run Order | Factor 1 Glycerin wt. % | Factor 2 DOSS wt. % | Factor 3 GML wt. % | Response 1 Max Emulsion size (micron) | Response 2 MSSA | Response 3 MRSA |
|---|---|---|---|---|---|---|---|
| 48 | 1 | 25.0 | 1.25 | 2.0 | 163 | 3.35 | 5.77 |
| 49 | 2 | 15.0 | 0.50 | 6.0 | 45 | 0.78 | 1.17 |
| 50 | 3 | 25.0 | 2.00 | 4.0 | 90 | 6.68 | 6.31 |
| 51 | 4 | 5.0 | 1.25 | 2.0 | 50 | 0.76 | 1.71 |
| 52 | 5 | 15.0 | 1.25 | 4.0 | 85 | 3.38 | 3.37 |
| 53 | 6 | 25.0 | 0.50 | 4.0 | 80 | 1.21 | 2.35 |
| 54 | 7 | 5.0 | 1.25 | 6.0 | 15 | 1.03 | 1.39 |
| 55 | 8 | 15.0 | 1.25 | 4.0 | 95 | 3.41 | 2.88 |
| 56 | 9 | 25.0 | 1.25 | 6.0 | 119 | 5.33 | 4.41 |
| 57 | 10 | 15.0 | 1.25 | 4.0 | 95 | 2.52 | 2.35 |
| 58 | 11 | 15.0 | 2.00 | 6.0 | 55 | 4.82 | 4.89 |
| 59 | 12 | 5.0 | 0.50 | 4.0 | 50 | 0.5 | 0.3 |
| 60 | 13 | 15.0 | 1.25 | 4.0 | 97 | 6.04 | 6.64 |
| 61 | 14 | 15.0 | 0.50 | 2.0 | 101 | 1.42 | 1.7 |
| 62 | 15 | 15.0 | 1.25 | 4.0 | 68 | 4.39 | 4.18 |
| 63 | 16 | 15.0 | 2.00 | 2.0 | 73 | 5.2 | 5.07 |
| 64 | 17 | 5.0 | 2.00 | 4.0 | 81 | 3.68 | 3.08 |
| 65 | 18 | 10.0 | 1.00 | 3.0 | 40 | 2.76 | 1.92 |
| 66 | 19 | 30.0 | 1.75 | 2.5 | NT | 4.75 | 7.76 |
| 67 | 20 | 30.0 | 1.25 | 2.0 | NT | 2.85 | 6.22 |
| 68 | 21 | 30.0 | 2.00 | 4.0 | NT | 6.76 | 6.76 |
| 69 | 22 | 30.0 | 0.50 | 4.0 | NT | 1.45 | 2.36 |
| 70 | 23 | 30.0 | 1.25 | 6.0 | NT | 3.66 | 6.93 |
| 71 | 24 | 23.5 | 2.00 | 2.5 | NT | 1.32 | 3.87 |
| 72 | 25 | 23.5 | 1.50 | 3.0 | NT | 1.71 | 3.73 |
| 73 | 26 | 15.0 | 1.25 | 4.0 | NT | 1.94 | 3.41 |
| 74 | 27 | 20.0 | 1.25 | 4.0 | NT | 1.92 | 2.96 |
| 75 | 28 | 10.0 | 1.25 | 4.0 | NT | 1.74 | 2.5 |
| 76 | 29 | 10.0 | 1.00 | 3.0 | NT | 1.08 | 4.02 |

NT = not tested preferably in 24 hours or less. On skin the procedure is similar except that a control site distinct from the treatment site may be selected on the treatment day. In this case, a log reduction may be determined. The procedure on skin is described in Federal Register, 21 CFR Parts 333 and 369, Tentative Final Monograph for Healthcare Antiseptic Drug Products; Proposed Rule, 1994 (scrub cup method). When performing this method on skin the antiseptic compositions are generally allowed to remain in contact with the skin for at least 6 hours under a suitable dressing such as that available under the trade designation TEGADERM from 3M Company, St. Paul, Minn., to check for antimicrobial activity. Preferred formulations show at least 1 log reduction and preferably at least 1.5 log reduction in 6 hours on a dry skin site (e.g., the abdomen).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An antimicrobial composition comprising:
   an effective amount of an antimicrobial lipid component comprising a (C8-C12)saturated fatty acid ester of a polyhydric alcohol, a (C12-C22)unsaturated fatty acid ester of a polyhydric alcohol, a (C8-C12)saturated fatty ether of a polyhydric alcohol, a (C12-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters comprise monoesters and the ethers comprise monoethers, and for sucrose the esters comprise monoesters, diesters, or combinations thereof, and the ethers comprise monoethers, diethers, or combinations thereof; wherein for monoesters, monoethers, or alkoxylated derivatives thereof, there is no more than 15 wt-% of a diester, diether, triester, triether, or alkoxylated derivatives thereof present, based on the total weight of the antimicrobial lipid components present in the composition;
   an effective amount of an enhancer component comprising an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof;
   a surfactant; and
   a hydrophilic component other than water, wherein the hydrophilic component other than water forms the greatest portion of the composition by weight;
   and wherein the composition contains less than 10 wt-% water when ready to use.

2. The antimicrobial composition of claim 1, wherein the antimicrobial lipid is present in an amount of at least 0.5 wt-% and no greater than 20 wt-%.

3. The antimicrobial composition of claim 1, wherein the C8-C12 saturated fatty acid ester of a polyhydric alcohol in the antimicrobial lipid is a C8-C12 alkyl monoesters of glycerin and propylene glycol, and the C8-C12 saturated fatty acid ether of a polyhydric alcohol is C8-C12 alkyl monoethers of glycerin and propylene glycol.

4. The antimicrobial composition of claim 1, wherein the antimicrobial lipid component comprises glycerol monolaurate, glycerol monocaprate, glycerol monocaprylate, propylene glycol monolaurate, propylene glycol monocaprate, propylene glycol monocaprylate, or combinations thereof.

5. The antimicrobial composition of claim 1, wherein the enhancer component is present in an amount of 0.4 wt-% to 20 wt-%.

6. The antimicrobial composition of claim 5, wherein the total concentration of the enhancer component relative to the total amount of the antimicrobial lipid component is within a range of 5:1 and 1:10, on a weight basis.

7. The antimicrobial composition of claim 1, wherein the surfactant is present in an amount of at least 0.1 wt-% and no greater than 10 wt-%.

8. The antimicrobial composition of claim 7, wherein the surfactant is present in an amount of 0.1 wt-% to 2 wt-%, and wherein the ratio of the total concentration of the surfactant to the total concentration of antimicrobial lipid component is within a range of 2:1 to 1:3, on a weight basis.

9. The antimicrobial composition of claim 1, wherein the surfactant comprises a sulfonate, a sulfate, a phosphonate, a phosphate, a poloxamer, a cationic surfactant, or mixtures thereof.

10. The antimicrobial composition of claim 1, wherein the hydrophilic component includes a polyhydric alcohol, a lower alcohol ether, a short chain ester, and combinations thereof, and wherein the hydrophilic component is soluble in water in an amount of at least 20 wt-% at 23° C.

11. The antimicrobial composition of claim 1, further comprising a hydrophobic component.

12. The antimicrobial composition of claim 11, wherein the hydrophobic component is an organic compound that is liquid, gelatinous, semisolid, or solid at 23° C. and has a solubility in water of less than 5 wt-% at 23° C.

13. The antimicrobial composition of claim 1, wherein the hydrophilic component is selected from glycerol, propylene glycol, dipropylene glycol, tripropylene glycol, polypropylene glycol, polyethylene glycol, diethylene glycol, pentaerythritol, trimethylolpropane, trimethylolethane, trimethylolbutane, sorbitol, mannitol, xylitol, pantothenol, ethylene glycol adducts of polyhydric alcohol, propylene oxide adducts of polyhydric alcohol, 1,3-butanediol, dipropylene glycol, diglycerine, polyglycerine, erythritol, sorbitan, sugars, sugar alcohols, or combinations thereof.

14. The antimicrobial composition of claim 1, wherein the hydrophilic component has a solubility in water of at least 20 wt-% at 23° C.

15. The antimicrobial composition of claim 1, wherein the viscosity of the composition is at least 500 cps.

16. The antimicrobial composition of claim 1, wherein the viscosity of the composition is at least 1,000 cps.

17. The antimicrobial composition of claim 1, wherein the viscosity of the composition is at least 10,000 cps.

18. An antimicrobial composition comprising:
    an effective amount of an antimicrobial lipid component having a solubility in water of at least 100 µg/100 g deionized water and at most 1 g/100 g deionized water;
    an effective amount of an enhancer component that includes an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof;
a surfactant distinct from the antimicrobial lipid component; and
a hydrophilic component other than water, wherein the hydrophilic component other than water forms the greatest portion of the composition by weight;
and wherein the composition contains less than 10 wt-% water when ready to use.

* * * * *

UNITED STATES PATENT AND TRADEMARK OFFICE
CERTIFICATE OF CORRECTION

PATENT NO.        : 10,471,036 B2
APPLICATION NO.   : 13/942122
DATED             : November 12, 2019
INVENTOR(S)       : Scholz et al.

It is certified that error appears in the above-identified patent and that said Letters Patent is hereby corrected as shown below:

On the Title Page

In item (56) the References Cited under "Other Publications" on page 4:

Column 1, Line 8, delete "Perservatives" and insert -- Preservatives --

Column 1, Line 11, delete "Philidelphia" and insert -- Philadelphia --

Column 1, Line 23, delete "bacteiuria" and insert -- bacteriuria --

Column 1, Line 24, delete "sudy"," and insert -- study", --

Column 1, Line 35, delete "Antimicrobil" and insert -- Antimicrobial --

Column 2, Line 7, delete "Staphylococus aureas" and insert -- Staphylococcus aureus --

Column 2, Line 10, delete "Salmoneallae" and insert -- Salmonella --

In item (56) the References Cited under "Other Publications" on page 5:

Column 1, Line 14, delete "aureua" and insert -- aureus --

Column 1, Line 24, delete "Syndrom" and insert -- Syndrome --

Column 1, Line 24-25, delete "Staphylococal" and insert -- Staphylococcal --

Column 1, Line 39, delete "Antibiotic-Auaceptibke" and insert -- antibiotic-susceptible --

Column 1, Line 55, delete ""Aersols,"" and insert -- "Aerosols," --

Signed and Sealed this
First Day of September, 2020

Andrei Iancu
*Director of the United States Patent and Trademark Office*

CERTIFICATE OF CORRECTION (continued)
U.S. Pat. No. 10,471,036 B2

Column 2, Line 2, delete "Microorganisma" and insert -- Microorganisms --

Column 2, Line 9, delete "Bacteris"," and insert -- Bacteria", --

Column 2, Line 14, delete "Antibotic" and insert -- Antibiotic --

Column 2, Line 15, delete "Pseudomonos" and insert -- Pseudomonas --

Column 2, Line 39, delete "Lipase-Catalzed" and insert -- Lipase-Catalyzed --

Column 2, Line 43, delete "Conrtibute" and insert -- Contribute --

In the Specification

Column 2, Line 39, delete "siniusitis." and insert -- sinusitis. --

Column 3, Line 21, delete "nasopharangyl" and insert -- nasopharyngeal --

Column 11, Line 44, delete "Pseudamonas" and insert -- Pseudomonas --

Column 14, Line 66, delete "nasoparangyl" and insert -- nasopharyngeal --

Column 15, Line 41, delete "deconolonized" and insert -- decolonized --

Column 15, Line 57, delete "afflications)." and insert -- affiliations). --

Column 16, Line 55, delete "nasopharangyl" and insert -- nasopharyngeal --

Column 16, Line 60, delete "Esherichia" and insert -- Escherichia --

Column 16, Line 67, delete "auerginosa," and insert -- aeruginosa, --

Column 17, Line 14, delete "faciitis;" and insert -- fasciitis; --

Column 18, Line 32, delete "an" and insert -- and --

Column 21, Line 6, delete "incorporatedinto" and insert -- incorporated into --

Column 21, Line 32, delete "nonioinic" and insert -- nonionic --

Column 22, Line 11, delete "ankenyl" and insert -- alkenyl --

Column 28, Line 30, delete "enterochlin," and insert -- enterochelin, --

Column 29, Line 55, delete "iosbutanol," and insert -- isobutanol, --

CERTIFICATE OF CORRECTION (continued)
U.S. Pat. No. 10,471,036 B2

Column 31, Line 5, delete "lipds" and insert -- lipids --

Column 32, Line 2, delete "aralklyl" and insert -- aralkyl --

Column 32, Line 28, delete "Sultanates" and insert -- Sulfonates --

Column 33, Line 32, delete "Parsipanny," and insert -- Parsippany, --

Column 34, Line 58, delete "antmicrobial" and insert -- Antimicrobial --

Column 36, Line 36, delete "suc" and insert -- such --

Column 37, Line 35, delete "isoparafins" and insert -- isoparaffins --

Column 37, Line 39, delete "isoparafins," and insert -- isoparaffins, --

Column 38, Line 17, delete "anti-imflammatory" and insert -- anti-inflammatory --

Column 38, Line 58, delete "chlorbutanol," and insert -- chlorobutanol, --

Column 38, Line 58, delete "iodopropylnyl" and insert -- iodopropynyl --

Column 43, Line 43, delete "betonite," and insert -- bentonite, --

Column 43, Line 43, delete "montmorrillonite" and insert -- montmorillonite --

Column 44, Line 66, delete "irriation" and insert -- irritation --

Column 45, Line 14, delete "aqeuous" and insert -- aqueous --

Column 46, Line 67 and Column 47, Line 1, delete "dimethyldiallyammonium" and insert -- dimethyldiallylammonium --

Column 49, Line 9, delete "Arsitoflex" and insert -- Aristoflex --

Column 49, Line 55, delete "poly(hexlmethacrylate)," and insert -- poly(hexylmethacrylate), --

Column 51, Line 52, delete "compositons" and insert -- compositions --

Column 52, Line 37, delete "terephalate," and insert -- terephthalate, --

Column 52, Lines 37-38, delete "polybuteneterephalate," and insert -- polybutyleneterephthalate, --

Column 52, Line 47, delete "perflourinated" and insert -- perfluorinated --

Column 56, Line 37, delete "$T_z$," and insert -- $T_2$, --

CERTIFICATE OF CORRECTION (continued)
U.S. Pat. No. 10,471,036 B2

Column 56, Line 61, delete "(GMC10)" and insert -- (GMC$_{10}$) --

Column 56, Line 67, delete "GMC10." and insert -- GMC$_{10}$. --

Column 57, Line 59, delete "micon" and insert -- micron --

Column 57, Line 61, delete "millilters" and insert -- milliliters --

Column 58, Line 3, delete "(GMC10)" and insert -- (GMC$_{10}$) --

Column 58, Line 18, delete "revolustions" and insert -- revolutions --

Column 58, Line 41, delete "MIC90" and insert -- MIC$_{90}$ --

Column 59, Line 66, delete "Mallinkrodt" and insert -- Mallinckrodt --

Column 62, Line 39, delete "isosterate," and insert -- isostearate, --

Column 64, Lines 29-30, delete "rotarevaporator" and insert -- rotary evaporator --

Column 68, Line 13, delete "mixng" and insert -- mixing --

Column 73, Line 47, delete "Docuate" and insert -- Docusate --

Column 78, Line 39-40, delete "suspenstion" and insert -- suspension --